(12) United States Patent
Tanzi et al.

(10) Patent No.: US 9,937,231 B2
(45) Date of Patent: Apr. 10, 2018

(54) METHODS AND AGENTS FOR TREATING ALZHEIMER'S DISEASE

(71) Applicant: THE GENERAL HOSPITAL CORPORATION, Boston, MA (US)

(72) Inventors: Rudolph Emile Tanzi, Cohasset, MA (US); Ana Griciuc, Somerville, MA (US)

(73) Assignee: THE GENERAL HOSPITAL CORPORATION, Boston, MA (US)

(*) Notice: Subject to any disclaimer, the term of this patent is extended or adjusted under 35 U.S.C. 154(b) by 66 days.

(21) Appl. No.: 14/780,242

(22) PCT Filed: Mar. 27, 2014

(86) PCT No.: PCT/US2014/032028
§ 371 (c)(1),
(2) Date: Sep. 25, 2015

(87) PCT Pub. No.: WO2014/160871
PCT Pub. Date: Oct. 2, 2014

(65) Prior Publication Data
US 2016/0038566 A1 Feb. 11, 2016

Related U.S. Application Data

(60) Provisional application No. 61/805,735, filed on Mar. 27, 2013.

(51) Int. Cl.
| | | |
|---|---|---|
| *A61K 38/17* | (2006.01) | |
| *A61K 31/7004* | (2006.01) | |
| *C07K 14/705* | (2006.01) | |
| *C07K 14/47* | (2006.01) | |
| *C07K 16/28* | (2006.01) | |

(52) U.S. Cl.
CPC ........ *A61K 38/178* (2013.01); *A61K 31/7004* (2013.01); *C07K 14/4711* (2013.01); *C07K 14/7056* (2013.01); *C07K 16/2851* (2013.01); *A01K 2217/05* (2013.01); *A01K 2217/075* (2013.01); *A01K 2217/15* (2013.01); *A01K 2227/105* (2013.01); *A01K 2267/0312* (2013.01)

(58) Field of Classification Search
None
See application file for complete search history.

(56) References Cited

U.S. PATENT DOCUMENTS

| 2003/0040604 A1 | 2/2003 | Anderson et al. | |
| 2004/0176309 A1 | 9/2004 | Kelm et al. | |
| 2012/0003306 A1* | 1/2012 | Sung .................. | A61K 9/19 424/452 |
| 2012/0076727 A1* | 3/2012 | McBride .......... | A61K 47/48746 424/1.53 |
| 2012/0263698 A1* | 10/2012 | Barber .................. | A61K 31/05 424/94.1 |

FOREIGN PATENT DOCUMENTS

WO 2010/105298 A1 9/2010

OTHER PUBLICATIONS

Manoharan 2016 "The role of reacitve oxygen species in the pathogenesis of alzheimer's disease, parkinson's disease, and huntington's disease: a mini review" Oxidative medicine cell longevity p. 1-15.*
Griciuc et al., "Alzheimer's Disease Risk Gene CD33 Inhibits Microglial Uptake of Amyloid Beta", Neuron 78:631-643 (2013).
Estus et al. Protective Allele of CD33 GWAS SNP Decreases Inclusion of Exon Encoding Ligand Binding Domain; Are CD33 Antagonists AD Therapeutics? 11th International Conference on Alzheimer's and Parkinson's Disease; Mar. 7, 2013; abstract, para 4.
Malik et al. CD33 Alzheimer's Risk-Altering Polymorphism, CD33 Expression, and Exon 2 Splicing; The Journal Neuroscience; of 33(33):13320-13325; p. 13321, col. 2, para 4 (2013).
NCBI 'myeloid cell sruface antigen CD33 isoform 2 precursor [*Homo sapiens*]; Accession NP_001076087'; Jul. 31, 2011 [online]. [Retrieved on Jul. 26, 2014]. Retrieved from the internet <URL http:www.ncbi.nih.gov/protein/130980072?sat=14&satkey=9121557>); p. 3, sequence listing for Seq. No. 8, p. 2.
Perez-Olivia et al. Epitope Mapping, Expression and Post-transitional Modifications of Two Isoforms of CD33 (CD33M and CD33m) on lymphoid and myeloid human cells; Glycobiology 21:757-770 (2011) abstract; Fig. 1.
Yankner et al. Mechanisms of Neuronal Degeneration Review in Alzheimer's Disease Neuron, 16(5):921-932; p. 922, col. 2, para 2. (1996).
Aguzzi et al., "Microglia: Scapegoat, Saboteur, or Something Else?", Science 339:156-161 (2013).
Bell et al., "Transport pathways for clearance of human Alzheimer's amyloid beta-peptide and apolipoproteins E and J in the mouse central nervous system", J. Cereb. Blood Flow Metab. 27:909-918 (2007).
Bertram et al., "Genome-wide Association Analysis Reveals Putative Alzheimer's Disease Susceptibility Loci in Addition to APOE", Am. J. Hum. Genet. 83:623-632 (2008).
Bertram et al., "The Genetics of Alzheimer Disease: Back to the Future", Neuron 68:270-281 (2010).
Brinkman-Van Der Linden et al., "CD33/Siglec-3 Binding Specificity, Expression Pattern, and Consequences of Gene Deletion in Mice", Mol. Cell. Biol. 23(12):4199-4206 (2003).
Crocker et al., "Siglecs and their roles in the immune system", Nat. Rev. Immunol. 7:255-266 (2007).

(Continued)

*Primary Examiner* — Adam Weidner
(74) *Attorney, Agent, or Firm* — Nixon Peabody LLP; David S. Resnick

(57) ABSTRACT

The present disclosure provides compositions and methods useful for treating or preventing diseases or disorders where beta amyloid accumulation or aggregation contributes to the pathology or symptomology of the disease, for example Alzheimer's disease.

18 Claims, 13 Drawing Sheets

(56) References Cited

OTHER PUBLICATIONS

Crocker et al., "CD33-related siglecs as potential modulators of inflammatory responses", Ann. N.Y. Acad. Sci. 1253:102-111 (2012).

Frank et al., "TREM2 is Upregulated in Amyloid Plaque-Associated Microglia in Aged APP23 Transgenic Mice", GLIA 56:1438-1447 (2008).

Grathwohl et al., "Formation and maintenance of Alzheimer's disease beta-amyloid plaques in the absence of microglia", Nat. Neurosci. 12(11):1361-1363 (2009).

Guerreiro et al., "TREM2 Variants in Alzheimer's Disease", N. Engl. J. Med. 368(2):117-127 (2013).

Harold et al., "Genome-wide association study identifies variants at CLU and PICALM associated with Alzheimer's disease, and shows evidence for additional susceptibility genes", Nat. Genet. 41(10):1088-1093 (2009).

Hollingworth et al., "Common variants at ABCA7, MS4A6A/MS4A4E, EPHA1, CD33 and CD2AP are associated with Alzheimer's disease", Nat. Genet. 43(5):429-435 (2011).

Hoyer et al.,"CD33 Detection by Immunohistochemistry in Paraffin-Embedded Tissues: A New Antibody Shows Excellent Specificity and Sensitivity for Cells of Myelomonocytic Lineage", Am. J. Clin. Pathol. 129:316-323 (2008).

Hsieh et al., "A role for TREM2 ligands in the phagocytosis of apoptotic neuronal cells by microglia", J. Neurochem. 109:1144-1156 (2009).

Jandus et al., "Targeting Siglecs—A novel pharmacological strategy for immuno- and glycotherapy", Biochem. Pharmacol. 82:323-332 (2011).

Jankowsky et al., "Mutant presenilins specifically elevate the levels of the 42 residue beta-amyloid peptide in vivo: evidence for augmentation of a 42-specific gamma secretase", Human Mol. Genet. 13(2):159-170 (2004).

Jiang et al., "ApoE Promotes the Proteolytic Degradation of Abeta", Neuron 58:681-693 (2008).

Jonsson et al., "Variant of TREM2 Associated with the Risk of Alzheimer's Disease", N. Engl. J. Med. 368(2):107-116 (2013).

Jurcic, "What Happened to Anti-CD33 Therapy for Acute Myeloid Leukemia?", Curr. Hematol. Malig. Rep. 7:65-73 (2012).

Karch et al., Expression of Novel Alzheimer's Disease Risk Genes in Control and Alzheimer's Disease Brains, PloS One 7:e50976 (2012).

Klesney-Tait et al., "The TREM receptor family and signal integration", Nat. Immunol. 7(12):1266-1273 (2006).

Lambert et al., "Genome-wide association study identifies variants at CLU and CR1 associated with Alzheimer's disease", Nat. Genet. 41(10):1094-1099 (2009).

Liu et al., "Apolipoprotein E and Alzheimer disease: risk, mechanisms and therapy", Nat. Rev. Neural. 9(2):106-118 (2013).

Mandrekar et al., "Microglia Mediate the Clearance of Soluble Abeta through Fluid Phase Macropinocytosis", J. Neurosci. 29(13):4252-4262 (2009).

Melchior et al., "Dual induction of TREM2 and tolerance-related transcript, Tmem176b, in amyloid transgenic mice: implications for vaccine-based therapies for Alzheimer's disease", ASN Neuro. 2(3):e00037 (2010).

Naj et al., "Common variants in MS4A4/M54A6E, CD2uAP, CD33, and EPHA1 are associated with late-onset Alzheimer's disease", Nat. Genet. 43(5):436-441 (2011).

O'Reilly et al., "Siglecs as targets for therapy in immune-cell-mediated disease", Trends Pharmacol. Sci. 30(5):240-248 (2009).

Paulson et al., "Siglecs as sensors of self in innate and adaptive immune responses", Ann N.Y. Acad. Sci. 1253(1):37-48 (2012).

Pillai et al., "Siglecs and Immune Regulation", Annu. Rev. Immunol. 30:357-392 (2012).

Prinz et al., "Heterogeneity of CNS myeloid cells and their roles in neurodegeneration", Nat. Neurosci. 14(10):1227-1235 (2011).

Ricart, "Antibody-Drug Conjugates of Calicheamicin Derivative: Gemtuzumab Ozogamicin and Inotuzumab Ozogamicin", Clin. Cancer Res. 17(20):6417-6427 (2011).

Rollins-Raval et al., "The value of immunohistochemistry for CD14, CD123, CD33, myeloperoxidase and CD68R in the diagnosis of acute and chronic myelomonocytic leukaemias" Histopathol. 60:933-942 (2012).

Selkoe, "Preventing Alzheimer's Disease", Science 337:1488-1492 (2012).

Seshadri et al., "Genome-wide Analysis of Genetic Loci Associated With Alzheimer Disease", JAMA 303 (18):1832-1840 (2010).

Tanzi et al., "Twenty Years of the Alzheimer's Disease Amyloid Hypothesis: A Genetic Perspective", Cell 120:545-555 (2005).

Tanzi, "A Brief History of Alzheimer's Disease Gene Discovery," Journal of Alzheimer's Disease 33:S5-S13 (2013).

Von Gunten et al., "Basic and Clinical Immunology of Siglecs", Ann. N.Y. Acad. Sci. 1143:61-82 (2008).

Yang et al., "p75NTR Regulates Abeta Deposition by Increasing Abeta Production But Inhibiting Abeta Aggregation with Its Extracellular Domain", J. Neurosci. 31(6):2292-2304 (2011).

\* cited by examiner

A
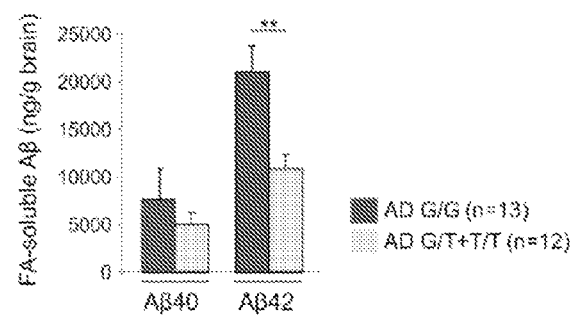
B
| rs3865444 T vs. G p-value | CTRL (n=15) | AD (n=25) | All (n=40) |
|---|---|---|---|
| TBS-soluble Aβ40 | 0.35 | 0.04 | 0.02 |
| TBS-soluble Aβ42 | 0.83 | 0.06 | 0.05 |
| FA-soluble Aβ40 | 0.05 | 0.22 | 0.10 |
| FA-soluble Aβ42 | 0.29 | 0.007 | 0.03 |
C 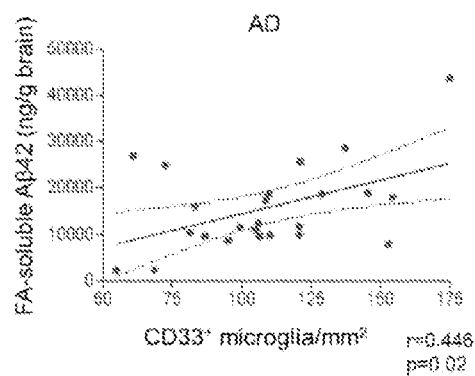
D 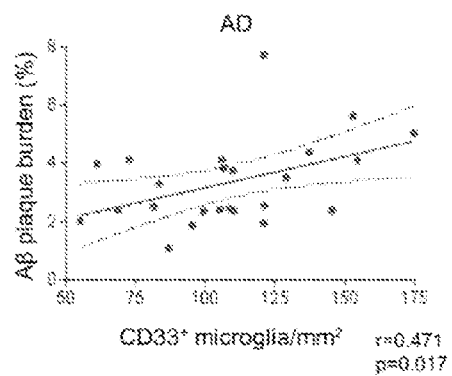
FIGS. 3A-3D

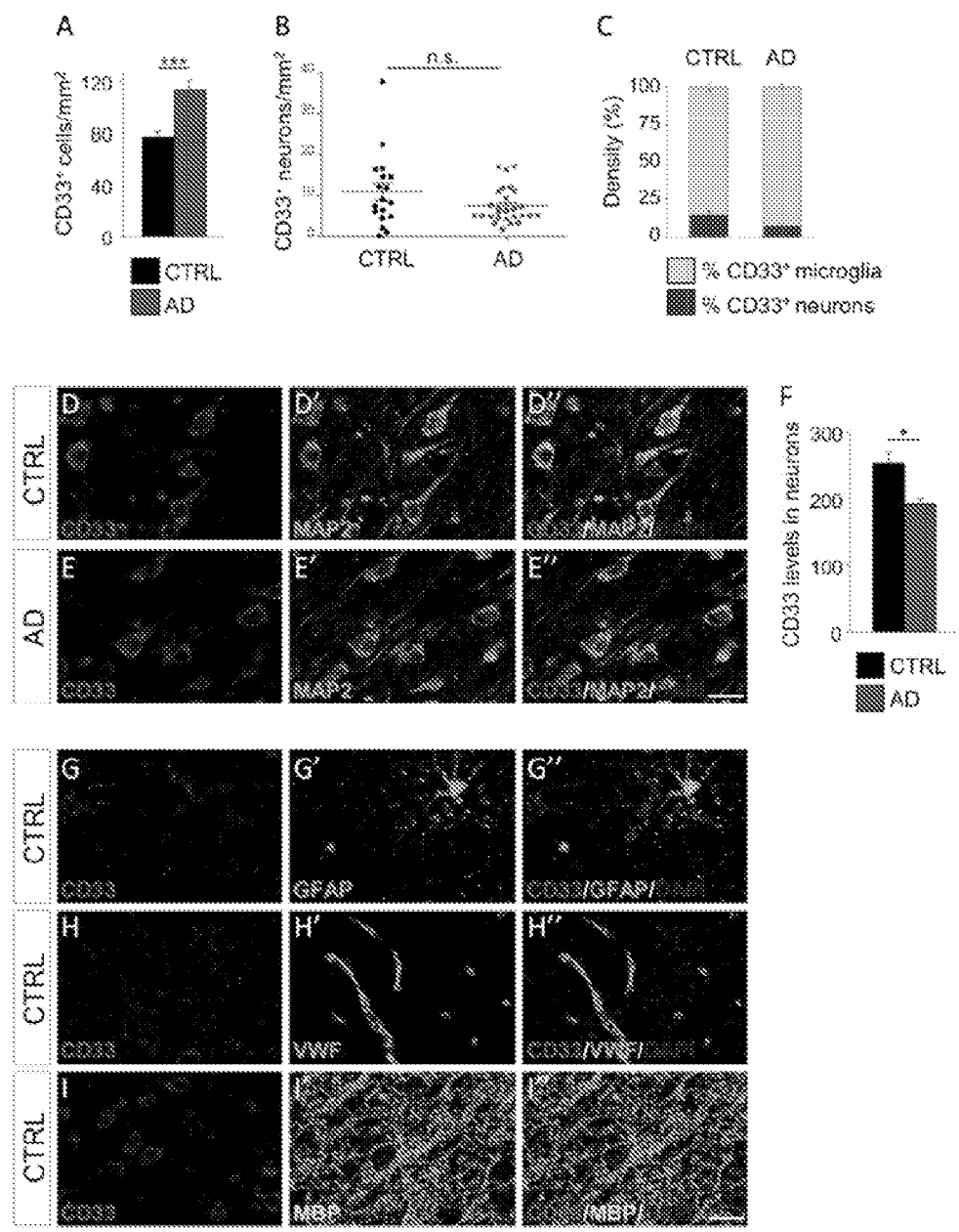
FIGS. 9A-9I"

○ GLYCOSYLATION SITE          ▓▓▓ TRANSMEMBRANE REGION

```
  1 MLWPLPLFLL CAGSLAQDLE FQLVAPESVT VEEGLCVHVP CSVFYPSIKL  50
 51 TLGPVTGSWL RKGVSLHEDS PVATSDPRQL VQKATQGRFQ LLGDPQKHDC 100
101 SLFIRDAQKN DTGMYFFRVV REPFVRYSYK KSQLSHVTSL SRTPDIIIIP 150
151 GTLEAGYPSN LTCSVPWACE QGTPPTFSWM QVERTIQLNS TALTSLSSRE 200
201 TEDSSVLFFT VTVERTIQLN VTRKSGQMRE LVLVAVGEAT 250
251 VKLLILGLCL VFLIVMFCRR KETKLSVHMG CENPIKRQEA IFSYNHCLSP 300
301 TASDAVTPGC SIHRLISRTP RCTAILRIQD PYRRTHLRNR AVSTLRFPWI 350
351 SWEGSLRSTQ RSKCTKLCSP VKNLCPHWLP VDNSCIPLIP EWVMLLCVSL 400
401 TLS 403
```

FIG. 11A

METHODS AND AGENTS FOR TREATING ALZHEIMER'S DISEASE

CROSS REFERENCE TO RELATED APPLICATIONS

This application is a 35 U.S.C. § 371 National Phase Entry Application of International Application No. PCT/US2014/032028, filed Mar. 27, 2014, which designates the U.S., and which claims benefit under 35 U.S.C. § 119(e) of the U.S. Provisional Application No. 61/805,735, filed Mar. 27, 2013, the content of both of which is incorporated herein by reference in their entirety.

SEQUENCE LISTING

The sequence listing of the present application has been submitted electronically via EFS-Web as an ASCII formatted sequence listing with a file name "030258-077501-PCT_SL", creation date of Sep. 25, 2015 and a size of 19,500 bytes. The sequence listing submitted via EFS-Web is part of the specification and is herein incorporated by reference in its entirety.

TECHNICAL FIELD

The present disclosure relates generally to methods and compositions for decreasing, inhibiting or reducing beta amyloid accumulation. The present disclosure also provides methods and compositions for treatment and/or prevention of neurodegenerative diseases and disorders.

BACKGROUND

Alzheimer's disease (AD) is the most prevalent neurodegenerative disease and the leading cause of dementia among the elderly. The mechanisms underlying the onset and progression of neurodegeneration and cognitive decline are incompletely understood. A major breakthrough in our understanding of AD was the identification of gene mutations associated with rare familial AD (FAD) cases. Autosomal dominant mutations in the amyloid beta (A4) precursor protein (APP) and presenilin 1 and 2 (PSEN1/2) genes greatly accelerate the rate of cognitive decline leading to early-onset dementia (Bertram et al., 2010; Tanzi, 2012). The vast majority of AD cases, however, are late-onset forms (LOAD), which lack an obvious Mendelian inheritance pattern. LOAD has a strong genetic component and is likely caused by a combination of multiple risk alleles, each with modest and partially penetrant effects, and environmental factors (Bertram et al., 2010). Although apolipoprotein E ε4 (APOE ε4) remained for a long time the only confirmed genetic risk factor for LOAD, it accounts for only 10-20% of the LOAD risk, suggesting the existence of additional risk factors (Liu et al., 2013). Recently, genome-wide association studies (GWAS) performed on extended cohorts (thousands of individuals) led to the identification of additional confirmed genetic risk factors for AD: CD33 (Bertram et al., 2008; Hollingworth et al., 2011; Naj et al., 2011), CLU, BIN1, PICALM, CR1, CD2AP, EPHA1, ABCA7, MS4A4A/MS4A6E (Harold et al., 2009; Hollingworth et al., 2011; Lambert et al., 2009; Naj et al., 2011; Seshadri et al., 2010) and TREM2 (Guerreiro et al., 2013; Jonsson et al., 2013). Understanding the molecular and cellular activities of these novel genes, as well as their functional interactions, should greatly advance our understanding of AD.

The deposition of amyloid beta (Aβ)-containing plaques is a pathological hallmark of both FAD and LOAD. Aβ results from the amyloidogenic processing of APP, which is cleaved by the sequential action of β-secretase/BACE1 and γ-secretase/Presenilin (Querfurth and LaFerla, 2010). In FAD, both APP and PSEN1/2 mutations lead to enhanced amyloidogenic processing of APP and enhanced production of the toxic Aβ42 species (Querfurth and LaFerla, 2010). Less is known about the mechanisms of Aβ formation, self-assembly and clearance in LOAD. Interestingly, several genes linked to LOAD have been shown to impact Aβ generation, aggregation, or clearance (Bertram et al., 2010), suggesting that Aβ dysregulation is a central pathogenic mechanism in LOAD. A widely accepted model of AD pathogenesis is the "amyloid hypothesis" whereby increased production and self-assembly of Aβ toxic species initiates a series of progressive changes that ultimately lead to neurodegeneration (Hardy and Selkoe, 2002; Hardy and Higgins, 1992; Tanzi and Bertram, 2005). In this hypothesis, persistent Aβ proteotoxic stress triggers the hyperphosphorylation and aggregation of the microtubule associated protein tau leading to neurofibrillary tangles, another pathological hallmark of AD (Tanzi and Bertram, 2005). Therefore, a better understanding of the mechanisms that regulate the generation and deposition, as well as clearance, of Aβ might improve the therapeutic approaches in AD.

Two single nucleotide polymorphisms (SNPs) in the CD33, rs3826656 (Bertram et al., 2008) and rs3865444 (Hollingworth et al., 2011; Naj et al., 2011), have been associated with LOAD. The 67 kDa type 1 transmembrane protein CD33 (Siglec-3) is a member of the sialic acid-binding immunoglobulin-like lectins (Siglecs) and is expressed in immune and hematopoietic cells. The Siglecs recognize sialic acid residues of glycoproteins and glycolipids, have one or more immunoreceptor tyrosine-based inhibition motifs (ITIMs) and mediate cell-cell interactions that inhibit or restrict immune responses (Crocker et al., 2012; Pillai et al., 2012). CD33 activity has been implicated in several processes such as: adhesion processes in immune or malignant cells, endocytosis, inhibition of cytokine release by monocytes and immune cell growth (Crocker et al., 2007; von Gunten and Bochner, 2008). To date, no functions have been described for CD33 in the brain.

SUMMARY

The present disclosure is based on inventors' discovery that CD33 protein inhibits uptake and clearance of beta amyloid in microglial cells. Inventors have shown that brain levels of insoluble Aβ-42 as well as amyloid plaque burden are markedly reduced in CD33$^{-/-}$ mice. Inventors have also demonstrated that CD33 inactivation mitigates Aβ pathology. Accordingly, in one aspect, the present disclosure relates generally to methods decreasing beta amyloid ("Aβ") accumulation by inhibition of CD33, for example inhibition of expression and/or activity of CD33 protein. The methods disclosed herein can be used for decreasing, inhibiting or reducing beta amyloid accumulation in a subject, for example in brain of the subject, in need thereof. In some embodiments, the beta amyloid is Aβ-42.

In some embodiments, the methods as disclosed herein comprise administering to a subject in need of decreasing, inhibiting or reducing beta amyloid accumulation, an effective amount of an agent that inhibits or reduces the expression or activity of CD33 protein.

In some other embodiments, the methods as disclosed herein comprise administering to a subject in need of decreasing, inhibiting or reducing beta amyloid accumulation, a CD33 protein or polypeptide that lacks sialic acid binding domain or a nucleic acid encoding such CD33 protein. A CD33 protein lacking the sialic acid binding domain is also referred to as a non-sialic CD33 protein or polypeptide. In some embodiments, the nucleic acid encoding the non-sialic CD33 protein is a modified RNA. In some embodiments, the nucleic acid encoding the non-sialic CD33 protein is a vector, e.g., an expression vector.

Without wishing to be bound by a theory, decreasing, inhibiting or reducing beta amyloid accumulation in a subject can be useful for treatment and/or prevention of diseases or disorders where beta amyloid accumulation or aggregation contributes to the pathology or symptomology of the disease. Thus, the disclosure also provides methods or treatment and/or prevention of diseases or disorders where beta amyloid accumulation or aggregation contributes to the pathology or symptomology of the disease. In some embodiments, the disclosure also provides methods or treatment and/or prevention of neuro-inflammatory diseases and disorders by inhibition CD33, for example inhibition of expression and/or activity of CD33 protein. It is not intended that the present invention to be limited to any particular stage of the disease (e.g. early or advanced).

In some embodiments, the methods as disclosed herein comprise administering to a subject in need of treatment and/or prevention of a disease or disorder where beta amyloid accumulation or aggregation contributes to the pathology or symptomology of the disease (e.g., a neuro-inflammatory disease), an effective amount of an agent that inhibits or reduces the expression or activity of CD33 protein.

In some embodiments, the methods as disclosed herein comprise administering to a subject in need of treatment and/or prevention of a disease or disorder where beta amyloid accumulation or aggregation contributes to the pathology or symptomology of the disease (e.g., a neuro-inflammatory disease), a CD33 protein that lacks sialic acid binding domain or a nucleic acid encoding such a CD33 protein.

In some embodiments, where beta amyloid accumulation or aggregation contributes to the pathology or symptomology of the disease results in a decline in cognitive function, for example Alzheimer's Disease, the method of treatment and/or prevention of the disease using the methods as disclosed herein can further comprise assessing the cognitive function of the subject after administration. In some embodiments, the method can comprise assessing presence of Aβ-42, for example, in the CSF.

In some embodiments, the methods disclosed herein can further comprise administering to the subject additional therapeutic agents, for example but not limited to therapeutic agents used in the treatment of neurodegenerative disorders. For example, where the neurodegenerative disorder is, for example, Alzheimer's Disease, the subject can be further administered therapeutic agents for the treatment of Alzheimer's Disease, for example but are not limited to ARICEPT or donepezil, COGNEX or tacrine, EXELON or rivastigmine, REMINYL or galantamine, anti-amyloid vaccine, Aβ-lowering therapies, mental exercise or stimulation.

In some embodiments, the methods as disclosed herein are applicable to subjects, for example mammalian subjects. In some embodiments, the subject is a human.

Without limitation, the agents that inhibits the expression or activity of the CD33 protein can be selected from the group consisting of small or large organic or inorganic molecules, nucleic acids, nucleic acid analogs and derivatives, peptides, peptidomimetics, proteins, antibodies and antigen binding fragments thereof, monosaccharides, disaccharides, trisaccharides, oligosaccharides, polysaccharides, lipids, glycosaminoglycans, an extract made from biological materials, and any combinations thereof.

In some embodiments, the agent is a nucleic acid. A nucleic acid agent can be selected from, for example, siRNA, shRNA, miRNA, anti-microRNA, antisense RNA or oligonucleotide, aptamer, ribozyme, and any combinations thereof. When the agent is a nucleic acid, the agent itself can be administered to the subject or a vector expressing/encoding the agent can be administered to the subject. In some embodiments, the vector expressing/encoding the agent is an Adeno-associated virus (AAV) vector.

In some embodiment, the agent is a small molecule, for example, but not limited to, a small molecule reversible or irreversible inhibitor of CD33 protein.

In some embodiments, the agent is an antibody. Antibody can be a polyclonal or monoclonal antibody. Further, the antibody can be a chimeric antibody. In some embodiments, the antibody is a humanized antibody.

BRIEF DESCRIPTION OF THE DRAWINGS

(FIG. 1A) Quantitative RT-PCR analysis of CD33 expression in the frontal cortex reveals increased CD33 mRNA levels in AD relative to control subjects; CD33 mRNA levels have been normalized to GAPDH or β-Actin mRNA. (FIG. 1B) Western blotting detection of CD33 in the frontal cortex reveals a marked upregulation in AD cases relative to age-matched controls. A less pronounced increased expression is also seen for Iba1. GAPDH served as loading control. (FIG. 1C) The CD33/GAPDH and CD33/Iba1 protein ratios are increased in AD patients relative to age-matched controls. (FIG. 1D) The levels of CD33 protein are decreased in carriers of the protective minor (T) allele of the CD33 SNP rs3865444. Bar graph showing CD33 protein levels in individuals from the indicated groups (CTRL or AD) and genotypes (G/G versus G/T or T/T). For (FIGS. 1A-1D): *$p<0.05$, $p<0.01$ and *$p<0.001$, student's t-test. Data are represented as mean±SEM. (FIG. 1E) Analysis based on general linear regression model reveals that the protective minor (T) allele of rs3865444 is associated with decreased CD33 protein, but not mRNA levels in both controls and AD cases ($p<0.05$ was considered statistically significant). See also FIG. 8 and Table 1.

(FIGS. 2A-2A'', FIGS. 2C-2C'') Fluorescent immunolabeling reveals co-localization between CD33 (visualized as red) and the microglial marker Iba1 (visualized as green) in the frontal cortex of CTRL (FIGS. 2A-2A'') and AD (FIGS. 2C-2C'') subjects. (FIGS. 2B and 2D) CD33 labeling using diaminobenzidine reveals numerous microglial cells that are positive for CD33. (FIG. 2E) Stereology-based quantification reveals increased numbers of CD33-positive microglial cells in the frontal cortex of AD cases (n=28) relative to controls (n=18), ***$p<0.001$, student's t-test. (FIG. 2F) CD33 protein levels normalized to Iba1 protein levels positively correlate with the numbers of CD33-immunoreactive microglia in the AD cases (n=25; r=0.525; p=0.007, Pearson's correlation test). (FIGS. 2G, 2H) CD33 protein levels correlate with the levels of the microglial marker Iba1, both in controls (n=15; r=0.543; p=0.03, Pearson's correlation test) and AD cases (n=25; r=0.582; p=0.002, Pearson's correlation test). (FIGS. 2I-2K) Carriers of the protective minor (T) allele of rs386544 exhibit decreased numbers of CD33-positive microglia. Shown are representative pictures from the frontal cortex of a (FIG. 2I) G/G carrier, (FIG. 2J) G/T carrier and (FIG. 2K) T/T AD carrier, stained for CD33. (FIG. 2L) Stereology-based quantifications reveal reduced numbers of CD33-positive microglia in carriers of two protective (T) alleles of rs3865444 (**$p<0.01$ T/T carriers versus G/G carriers, one-way Kruskal-Wallis ANOVA, Dunn's test). Data are represented as mean±SEM. Scale bars represent 25 µm. (FIG. 2M) The protective (T) allele of rs3865444 is associated with decreased numbers of CD33-immunoreactive microglia in both controls and AD cases (general linear regression model, $p<0.05$ was considered statistically significant). See also FIG. 9.

FIGS. 3A-3D show that CD33 microglial expression positively correlates with formic acid-soluble Aβ42 levels and amyloid plaque burden in AD. (FIG. 3A) Formic acid (FA)-soluble Aβ42 levels are decreased in carriers of the rs3865444 minor (T) allele. ELISA analysis of Aβ40 and Aβ42 in FA-soluble fractions isolated from the frontal cortex of AD cases of the indicated genotypes (**$p<0.01$, student's t-test). Data are represented as mean±SEM. (FIG. 3B) The protective rs3865444 (T) allele is associated with decreased levels of both FA-soluble Aβ42 and TBS-soluble Aβ40 in AD cases (n=25 AD cases, n=15 controls, general linear regression model, $p<0.05$ was considered statistically significant). (FIG. 3C) The numbers of CD33-immunoreactive microglia positively correlate with the FA-soluble Aβ42 levels in AD cases (n=25; r=0.446; p=0.02, Spearman's correlation test). (FIG. 3D) The numbers of CD33-positive microglia positively correlate with amyloid plaque burden in AD brain (n=25; r=0.471; p=0.017; Spearman's correlation test). See also FIG. 10.

(FIGS. 4A-4A', FIGS. 4B-4B''') Primary microglial cell cultures were incubated with fluorescently labeled Aβ42 for 3 hours and then subjected to immunofluorescent labeling for CD33 (FIG. 4A, FIG. 4B) and Iba1 (FIG. 4A', FIG. 4B'''). Microglial cultures derived from CD33$^{-/-}$ mice, at postnatal day 1, exhibited a markedly increased Aβ42 uptake (compare FIG. 4A' and FIG. 4B'). Scale bar represents 25 µM. (FIG. 4C) Quantification of Aβ42 average signal intensity in individual cells reveals a strong increase in Aβ42 signal in CD33$^{-/-}$ cells relative to WT cells (at least 30 cells were scored per genotype, $p<0.01$, student's t-test). (FIGS. 4D, 4E) Microglial cell cultures were treated with unlabeled Aβ42 and incubated for 3 hours. After incubation, cells were either collected for ELISA analysis (t=0) or washed and incubated for an additional 3 hours in Aβ-free medium, followed by ELISA analysis (t=3 hrs). (FIG. 4D) CD33-/- microglia exhibit increased Aβ42 uptake levels relative to WT microglia (t=0) (results were derived from 4 independent experiments; *$p<0.001$, student's t-test). (FIG. 4E) Similar rates of Aβ42 degradation in CD33$^{-/-}$ and WT microglial cells incubated in the absence of Aβ42 for an additional 3 hours (the percentage of remaining Aβ42 was the ratio of Aβ42 remaining at t=3 hours to the total amount of Aβ42 internalized at t=0). Data are represented as mean±SEM. See also FIG. 11.

(FIGS. 5A-D''') BV2 microglial cells were incubated with fluorescently labeled Aβ42 for 3 hours and then subjected to immunofluorescent labeling for CD33 (FIGS. 5A-5D) and Iba1 (FIGS. 5A'''-5D'''). Overexpression of WT-CD33 decreases the amount of internalized Aβ42 (compare FIG. 5A' and FIG. 5B'). Expression of a ubiquitylation-defective CD33 variant (K7R-CD33) further decreases the amount of internalized Aβ42 (compare FIG. 5B' and FIG. 5C'). A CD33 variant lacking the sialic acid-binding V-type immunoglobulin-like extracellular domain (ΔV-Ig-CD33) no longer inhibits Aβ42 uptake (compare FIG. 5B', FIG. 5C' with FIG. 5D'). Scale bar represents 25 µM. (FIG. 5E) Quantification of Aβ42 signal intensity in individual cells transfected with the indicated constructs or with an empty vector; at least 30 cells were scored per condition (*$p<0.05$, $p<0.01$, *$p<0.001$, one-way ANOVA, Tukey's test). The series from left to right represents empty vector, GFP, CD33$^{WT}$, CD33$^{K7R}$, CD33$^{\Delta V-Ig}$. (FIG. 5F, FIG. 5G) BV2 cells were treated with unlabeled Aβ42 and incubated for 3 hours. The series from left to right represents empty vector, GFP, CD33$^{WT}$, CD33$^{K7R}$, cD33$^{\Delta V-Ig}$. After incubation, cells were either collected for ELISA analysis (t=0) or washed and incubated for an additional 3 hours in Aβ-free medium, followed by ELISA analysis (t=3 hours). (FIG. 5F) WT-CD33 inhibits microglial uptake of Aβ42. ELISA quantifications of Aβ42 levels in BV2 cells transfected with the indicated constructs or with empty vector (results were obtained from 4 independent experiments; *$p<0.05$, **$p<0.01$, one-way ANOVA, Tukey's test). (FIG. 5G) CD33 overexpression does not affect the rate of Aβ42 degradation by BV2 cells (the percentage of remaining Aβ42 was the ratio of Aβ42 remaining at t=3 hours to the total amount of Aβ42 internalized at t=0). Both empty vector and a GFP-expressing vector served as controls. Data are represented as mean±SEM.

(FIG. 6A) Western blotting analysis of cortical extracts reveals increased levels of APP and APP C-terminal fragments (CTFs) in four month-old APP/PS1 mice in comparison to controls. However, APP and APP-CTFs levels are similar in APP/PS1 and APP/PS1/CD33$^{-/-}$ mice. β-Actin served as loading control. (FIG. 6B) Quantification of APP, α-CTF and β-CTF levels in APP/PS1 and APP/PS1/CD33-/- mice (n=9 male mice were analyzed per group). (FIGS. 6C-6F) ELISA analysis of Aβ40 (FIG. 6C, FIG. 6E) and Aβ42 (FIG. 6D, FIG. 6F) in TBS-soluble (FIG. 6C, FIG. 6D) or formic acid (FA)-soluble (FIG. 6E, FIG. 6F) fractions isolated from the cortex of four month-old male mice of the indicated genotypes. APP/PS1 mice exhibit increased levels of Aβ40 and Aβ42 relative to WT and CD33$^{-/-}$ mice, as expected. No differences in Aβ40 levels and TBS-soluble Aβ42 levels were seen in APP/PS1 and APP/PS1/CD33$^{-/-}$ mice. However, the FA-soluble Aβ42 levels were markedly decreased in APP/PS1/CD33$^{-/-}$ relative to APP/PS1 mice (n=9-12 mice were analyzed per group, *$p<0.05$, one-way Kruskal-Wallis ANOVA, Dunn's test). Data are represented as mean±SEM. For FIGS. 6C-6F, the series from left to right represents WT, CD33$^{-/-}$, APP/PS1, APP/PS1/CD33$^{-/-}$, APP/PS1/CD33$^{-/-}$. See also FIG. 12.

(FIGS. 7A-7D) Photomicrographs of selected cortical (FIG. 7A, FIG. 7B) and hippocampal (FIG. 7C, FIG. 7D) fields from 6-7 month-old APP/PS1 (FIG. 7A, FIG. 7C) and APP/PS1/CD33$^{-/-}$ brains (FIG. 7D, FIG. 7E) were stained with the anti-Aβ antibody 3D6 to reveal Aβ plaques. The Aβ plaque burden is decreased in APP/PS1/CD33$^{-/-}$ brains relative to APP/PS1 brains (compare FIG. 7B with FIG. 7A and FIG. 7D with FIG. 7C). (FIG. 7E, FIG. 7F) Quantification of amyloid plaque burden in the cortex (FIG. 7E) and hippocampus (FIG. 7F) of 6-7 month-old APP/PS1 and APP/PS1/CD33-/- brains (n=9-11 male mice were analyzed per group, *p<0.05, **p<0.01, student's t-test). Data are represented as mean±SEM. Scale bar is 50 μm.

(FIG. 8A) Schematic diagram of the transcribed CD33 RNA (CD33 pre-mRNA; upper) and CD33 mRNA (lower). The sets of primers (Forward F1 and reverse R1 targeting exons 3-4; forward F2 and reverse R2 targeting exons 4-5) used for quantitative RT-PCR are shown by the arrows. (FIG. 8B) Results of qRT-PCR using the indicated sets of primers. mRNA was isolated from frozen cortical extracts obtained from AD cases (n=25) and age-matched controls (n=15) of the indicated genotypes. Each series represents CTRL G/G, CTRL G/T+T/T, AD G/G, AD G/T+T/T from left to right. (FIG. 8C) CD33 protein levels are decreased in carriers of the rs3865444 minor (T) allele. Western blotting was used to quantify CD33 protein levels in AD cases (n=25) and age-matched controls (n=15) of the indicated genotypes. CD33 expression was normalized to GAPDH or to the microglial marker Iba1 (*p<0.05, student's t-test). Data are represented as mean±SEM. Each series represents CTRL G/G, CTRL G/T, CTRL T/T, AD G/G, AD G/T, AD T/T from left to right.

FIGS. 9A-9I''' show CD33 expression pattern in the human brain. (FIG. 9A) Stereology-based quantifications of the number of CD33-positive cells in the frontal cortex of AD cases (n=28) and age-matched controls (n=18) (***p<0.001, student's t-test). (FIG. 9B) Stereology-based quantifications of the number of CD33-positive neurons in the frontal cortex of AD cases (n=28) and age-matched controls (n=18) (p=n.s., Mann-Whitney U test). (FIG. 9C) Distribution of CD33-positive cells in AD cases and age-matched controls. Most CD33 cells are microglial, and only a minor fraction corresponds to neurons. (FIGS. 9D-9D'', FIGS. 9E-9E'') Fluorescent immunolabeling reveals co-localization between CD33 (visualized as red) and the neuronal marker MAP2 (visualized as green) in controls (FIGS. 9D-9D'') as well as AD cases (FIGS. 9E-9E''). (FIG. 9F) Quantification of CD33 levels within MAP2-positive neurons (*p<0.05, student's t-test). Data are represented as mean±SEM. (FIGS. 9G-9I) CD33 is not expressed in astrocytes, endothelial cells or oligodendrocytes in the aged human brain. Immunolabeling for CD33 (visualized as red; FIGS. 9G-9I) and astrocytic (GFAP; visualized as green; FIG. 9G'), endothelial (von Willebrand factor [VWF]; visualized as green; FIG. 9H'), or oligodendrocytic (myelin basic protein [MBP]; visualized as green; FIG. 9I') markers reveals no co-localization between CD33 signal and these markers. Scale bar is 25 μm.

(FIGS. 10A-10C) Frontal cortices from AD cases were immunolabeled for CD33 (visualized as red; FIGS. 10A', 10B', and 10C'), the microglial marker Iba1 (visualized as white; FIGS. 10A', 10B''', and 10C''') and stained with Thioflavin S (visualized as green; FIGS. 10A, 10B, and 10C) to detect amyloid plaques. CD33 exhibited a prominent microglial localization that was broadly distributed throughout the frontal cortex. In addition, an increased density of CD33-positive microglia was noted around amyloid plaques (white circles; FIG. 10A'', FIG. 10B''). (FIGS. 10C-10C''') Higher-magnification views of the selected Aβ plaque (white arrow in FIG. 10B''). Scale bar is 25 μm in FIG. 10A''' and FIG. 10B''' and 5 μm in FIG. 10C'''.

FIGS. 11A-11C shows mCD33-specific polyclonal antibody. (FIG. 11A) Shown is a schematic representation of the mouse CD33 (mCD33) protein, highlighting the location of the immunizing peptide (shaded area in the first line; residues 18-32). The amino acid sequence is SEQ ID NO 1. (FIG. 11B) The rabbit polyclonal antibody raised against this CD33 peptide was tested on protein extracts derived from HEK293 cells transfected with either an empty vector or a vector encoding full-length mouse CD33. GAPDH served as loading control. (FIG. 11C) Western blotting using the anti-CD33 rabbit polyclonal antibody and cortical lysates reveals CD33 expression in WT mice and absence of CD33 expression in CD33$^{-/-}$ mice. GAPDH served as loading control.

(FIG. 12I) Quantification of Iba1-positive microglial cell numbers reveals similar microglia numbers in the hippocampus and cortex in mice of the indicated genotypes (n=5-6 male mice/genotype, 4 month-old). (FIG. 12J) Western blotting using a Iba1 antibody also reveals no changes in Iba1 protein levels in the cortex of mice of the indicated genotypes. (FIG. 12K) Quantifications of Iba1 protein levels, using normalization to β-Actin (n=6 male mice/genotype, 4 month-old). (FIG. 12T) Quantification of GFAP-positive astrocyte numbers reveals similar astrogliosis in the cortex of WT and CD33$^{-/-}$ mice and more astrogliosis in APP/PS1 and APP/PS1/CD33$^{-/-}$ mice; however, the extent of astrogliosis was similar in the cortex of APP/PS1 and APP/PS1/CD33$^{-/-}$ mice (n=5-6 male mice/genotype, 4 month-old). (FIG. 12U) Quantification of the GFAP-immunoreactive cell numbers in the hippocampus reveals a similar degree of astrogliosis in the hippocampus in all groups (n=5-6 male mice/genotype, one-way Kruskal-Wallis ANOVA, Dunn's test). Data are represented as mean±SEM. Scale bar is 25 μm.

DETAILED DESCRIPTION

Figures 1A, 1B, 1C, 1D, 1E:
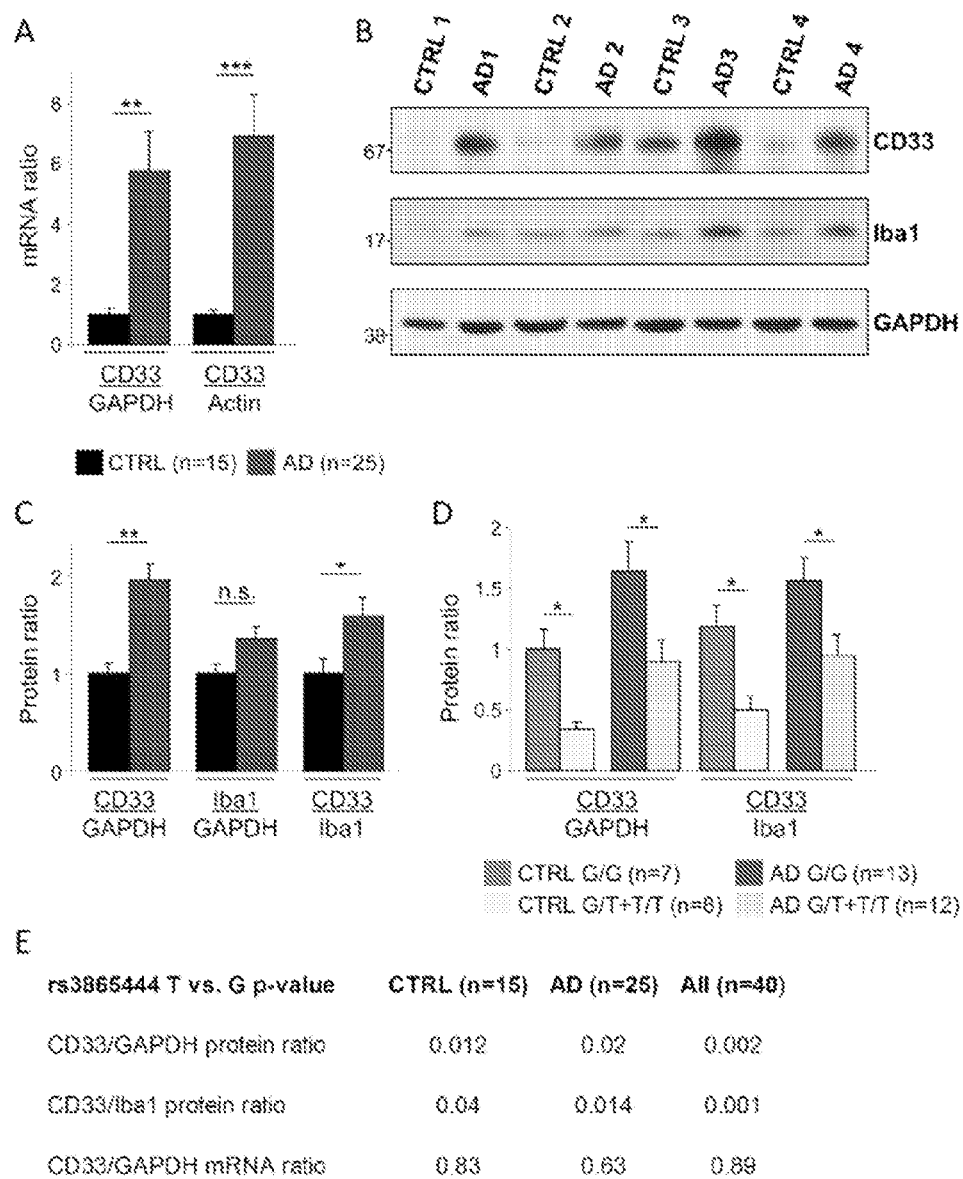
FIGS. 1A-1E show increased CD33 expression in AD.

In part, this invention is based on the inventors' discovery that CD33 protein inhibits uptake and clearance of beta amyloid in microglial cells and brain levels of insoluble Aβ-42 as well as amyloid plaque burden are markedly reduced in CD33$^{-/-}$ mice. In particular, decreasing, inhibiting, or reducing the expression or activity of CD33 protein led to reduction of amyloid, for example beta-amyloid (or Aβ-42) accumulation. As the work disclosed herein shows, CD33 inactivation can mitigate Aβ pathology.

Therefore, the inventors have discovered that inactivation of CD33, e.g., with CD33, inhibitors can be used in the treatment and/or prevention of neuro-inflammatory disease and disorders. As used herein, the term "neuro-inflammatory disease" refers to an inflammatory disease or disorder in the central nervous system (CNS, brain, and spinal cord), and includes, but is not limited to, neurodegenerative diseases and disorders.

CD33 is a transmembrane, immunoglobulin-like lectin that normally has a sialic acid-binding domain. CD33 is also known as SIGLEC3, and it encodes a cell-surface receptor on cells of monocytic or myeloid lineage, and regulates the innate immune system (Bertram et al., Am. J. Hum. Gnet. 2008, 83, 623-632). The amino acid sequence for CD33 is known in the art and is provided below for reference: mpllllpll wagalamdpn fwlqvqesvt vqeglcvlvp ctffhpipyy dknspvhgyw fregaiisrd spvatnkldq evqeetqgrf rllgdpsrnn cslsivdarr rdngsyffrm ergstkysyk spqlsvhvtd lthrpkilip gtlepghskn ltcsyswace qgtppifswl saaptslgpr tthssvliit prpqdhgtnl tcqvkfagag vttertiqln vtyvpqnptt gifpgdgsgk qetragvvhg aiggagvtal lalcicliff ivkthrrkaa rtavgrndth pttg-saspkh gkksklhgpt etsscsgaap tvemdeelhy aslnfhgmnp skdt-steyse vrtq (SEQ ID NO: 2)

As used herein, the term "neurodegenerative disease" refers to a varied assortment of central nervous system disorders characterized by gradual and progressive loss of neural tissue and/or neural tissue function. A neurodegenerative disease is a class of neurological disorder or disease, and where the neurological disease is characterized by a gradual and progressive loss of neural tissue, and/or altered neurological function, typically reduced neurological function as a result of a gradual and progressive loss of neural tissue. Examples of neurodegenerative diseases include for example, but are not limited to, Alzheimer's disease (AD), Parkinson's disease (PD), Huntington's Disease, Amyotrophic Lateral Sclerosis (ALS, also termed Lou Gehrig's disease) and Multiple Sclerosis (MS), polyglutamine expansion disorders (e.g., HD, dentatorubropallidoluysian atrophy, Kennedy's disease (also referred to as spinobulbar muscular atrophy), spinocerebellar ataxia (e.g., type 1, type 2, type 3 (also referred to as Machado-Joseph disease), type 6, type 7, and type 17)), other trinucleotide repeat expansion disorders (e.g., fragile X syndrome, fragile XE mental retardation, Friedreich's ataxia, myotonic dystrophy, spinocerebellar ataxia type 8, and spinocerebellar ataxia type 12), Alexander disease, Alper's disease, ataxia telangiectasia, Batten disease (also referred to as Spielmeyer-Vogt-Sjogren-Batten disease), Canavan disease, Cockayne syndrome, corticobasal degeneration, Creutzfeldt-Jakob disease, ischemia stroke, Krabbe disease, Lewy body dementia, multiple system atrophy, Pelizaeus-Merzbacher disease, Pick's disease, primary lateral sclerosis, Refsum's disease, Sandhoff disease, Schilder's disease, spinal cord injury, spinal muscular atrophy (SMA), SteeleRichardson-Olszewski disease, Tabes dorsalis, and the like. In some embodiments, the neurodegenerative disease is Alzheimer's disease.

The expression or activity of CD33 can be reduced by inhibition of the expression of CD33 protein or by inhibiting activity of CD33. The expression of CD33 can be inhibited by "gene silencing" methods commonly known by persons of ordinary skill in the art. The reduction in activity can be due to affecting one or more characteristics of CD33 including decreasing its catalytic activity or by inhibition a co-factor of CD33 or by binding to CD33 with a degree of avidity that is such that the outcome is that beta amyloid uptake is increased in cells expressing the CD33, such microglial cells. In particular, inhibition of CD33 can be determined using an assay for measuring beta amyloid uptake in cells expressing CD33, for example, but not limited to, by using the CD33 uptake assay as disclosed herein. In some embodiments, activity of CD33 is sialic acid binding. Thus, the methods disclosed herein decrease, inhibit, or reduce binding of sialic acid to CD33.

The term "agent" refers to any entity which is normally not present or not present at the levels being administered in the cell. Agent can be selected from a group comprising: chemicals; small molecules; nucleic acid sequences; nucleic acid analogues; proteins; peptides; aptamers; antibodies; or fragments thereof. A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA) etc. Such nucleic acid sequences include, for example, but are not limited to, nucleic acid sequence encoding proteins, for example that act as transcriptional repressors, antisense molecules, ribozymes, small inhibitory nucleic acid sequences, for example but are not limited to RNAi, shRNAi, siRNA, micro RNAi (mRNAi), antisense oligonucleotides etc. A protein and/or peptide or fragment thereof can be any protein of interest, for example, but are not limited to: mutated proteins; therapeutic proteins and truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Alternatively, the agent can be intracellular within the cell as a result of introduction of a nucleic acid sequence into the cell and its transcription resulting in the production of the nucleic acid and/or protein inhibitor of CD33 within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

In some embodiments, the agent can cross the blood-brain barrier or can be formulated to cross the blood-brain barrier.

In some embodiments, the agent that inhibits the expression or activity of CD33 is a nucleic acid, also referred to as a nucleic acid agent herein. In the context of this disclosure, the term "nucleic acid" refers to a polymer or oligomer of nucleotide or nucleoside monomers consisting of naturally occurring bases, sugars and intersugar linkages. The term "nucleic acid" or "oligonucleotide" or "polynucleotide" are used interchangeably herein and can mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof.

Without limitation, the nucleic acid agent can be single-stranded or double-stranded. A single-stranded nucleic acid agent can have double-stranded regions and a double-stranded nucleic acid agent can have single-stranded regions. The nucleic acid can be of any desired length. In particular embodiments, nucleic acid can range from about 10 to 100 nucleotides in length. In various related embodiments, nucleic acid agents, single-stranded, double-stranded, and triple-stranded, can range in length from about 10 to about 50 nucleotides, from about 20 to about 50 nucleotides, from about 15 to about 30 nucleotides, from about 20 to about 30 nucleotides in length. In some embodiments, nucleic acid agent is from about 9 to about 39 nucleotides in length. In some other embodiments, nucleic acid agent is at least 30 nucleotides in length.

The nucleic acid agent can comprise any nucleic acid or oligonucleotide modification described herein and below. In certain instances, it can be desirable to modify one or both strands of a double-stranded nucleic acid agent. In some cases, the two strands will include different modifications. In other instances, multiple different modifications can be included on each of the strands. The various modifications on a given strand can differ from each other, and can also differ from the various modifications on other strands. For example, one strand can have a modification, e.g., a modification described herein, and a different strand can have a different modification, e.g., a different modification described herein. In other cases, one strand can have two or more different modifications, and the another strand can include a modification that differs from the at least two modifications on the first strand.

Single-stranded and double-stranded nucleic acid agents that are effective in inducing RNA interference are referred to as siRNA, RNAi agent, iRNA agent, or RNAi inhibitor herein. As used herein, the term "iRNA agent" refers to a nucleic acid agent which can mediate the targeted cleavage of an RNA transcript via an RNA-induced silencing complex (RISC) pathway.

As used herein, "target sequence" refers to a contiguous portion of the nucleotide sequence of an mRNA molecule formed during the transcription of a CD33 gene, including messenger (mRNA) that is a product of RNA processing of a primary transcription product. The target portion of the sequence will be at least long enough to serve as a substrate for iRNA-directed cleavage or binding of antisense RNA/oligonucleotide at or near that portion. For example, the target sequence will generally be from 9-36 nucleotides in length, e.g., 15-30 nucleotides in length, including all subranges therebetween. As non-limiting examples, the target sequence can be from 15-30 nucleotides, 15-26 nucleotides, 15-23 nucleotides, 15-22 nucleotides, 15-21 nucleotides, 15-20 nucleotides, 15-19 nucleotides, 15-18 nucleotides, 15-17 nucleotides, 18-30 nucleotides, 18-26 nucleotides, 18-23 nucleotides, 18-22 nucleotides, 18-21 nucleotides, 18-20 nucleotides, 19-30 nucleotides, 19-26 nucleotides, 19-23 nucleotides, 19-22 nucleotides, 19-21 nucleotides, 19-20 nucleotides, 20-30 nucleotides, 20-26 nucleotides, 20-25 nucleotides, 20-24 nucleotides, 20-23 nucleotides, 20-22 nucleotides, 20-21 nucleotides, 21-30 nucleotides, 21-26 nucleotides, 21-25 nucleotides, 21-24 nucleotides, 21-23 nucleotides, or 21-22 nucleotides.

While a target sequence is generally 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Further, the target sequence can start at any desired nucleotide position of the given target RNA.

CD33 mRNA sequences are known in the art. For example, human CD33 mRNA sequence can be accessed from NCBI Refseq collection by NCBI Reference Sequences: NM_001082618.1 (SEQ ID NO: 3); NM_001772.3 (SEQ ID NO: 4); NM_001177608.1 (SEQ ID NO: 5); XM_005259434.1 (SEQ ID NO: 6); and XM_005259433.1 (SEQ ID NO: 7). Without limitations, the target sequence can be a portion of any one of the above noted human CD33 mRNA sequences. In some embodiments, the nucleic acid agent comprises a nucleotide substantially complementary to 15-30 nucleotides, 15-26 nucleotides, 15-23 nucleotides, 15-22 nucleotides, 15-21 nucleotides, 15-20 nucleotides, 15-19 nucleotides, 15-18 nucleotides, 15-17 nucleotides, 18-30 nucleotides, 18-26 nucleotides, 18-23 nucleotides, 18-22 nucleotides, 18-21 nucleotides, 18-20 nucleotides, 19-30 nucleotides, 19-26 nucleotides, 19-23 nucleotides, 19-22 nucleotides, 19-21 nucleotides, 19-20 nucleotides, 20-30 nucleotides, 20-26 nucleotides, 20-25 nucleotides, 20-24 nucleotides, 20-23 nucleotides, 20-22 nucleotides, 20-21 nucleotides, 21-30 nucleotides, 21-26 nucleotides, 21-25 nucleotides, 21-24 nucleotides, 21-23 nucleotides, or 21-22 nucleotides contiguous nucleotides of one of the above-noted human CD33 mRNA sequences.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing. Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within a double-stranded nucleic acid include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs (bp), while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or 100% complementarity means that all the contiguous residues of a nucleic acid sequence will hydrogen bond with the same number of contiguous residues in a second nucleic acid sequence. Less than perfect complementarity refers to the situation in which some, but not all, nucleoside units of two strands can hydrogen bond with each other. "Substantial complementarity" refers to polynucleotide strands exhibiting 90% or greater complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 5 nucleotides.

"Complementary" sequences, as used herein, can also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" an mRNA refers to a polynucleotide that is substantially complementary to a contiguous portion of the mRNA of interest (e.g., an mRNA encoding CD33). For example, a polynucleotide is complementary to at least a part of a CD33 mRNA if the sequence is substantially complementary to a non-interrupted portion of an mRNA encoding CD33.

The term "double-stranded RNA" or "dsRNA," as used herein refers to an iRNA agent that includes an RNA molecule or complex of molecules having a hybridized duplex region that comprises having "sense" and "antisense" orientations with respect to a target RNA. The duplex region can be of any length that permits specific degradation of a desired target RNA through a RISC pathway, but will typically range from 9 to 36 base pairs (bp) in length, e.g., 15-30 bp in length. Considering a duplex between 9 and 36 bp the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 and any sub-range therein between, including, but not limited to 15-30 bp, 15-26 bp, 15-23 bp, 15-22 bp, 15-21 bp, 15-20 bp, 15-19 bp, 15-18 bp, 15-17 bp, 18-30 bp, 18-26 bp, 18-23 bp, 18-22 bp, 18-21 bp, 18-20 bp, 19-30 bp, 19-26 bp, 19-23 bp, 19-22 bp, 19-21 bp, 19-20 bp, 20-30 bp, 20-26 bp, 20-25 bp, 20-24 bp, 20-23 bp, 20-22 bp, 20-21 bp, 21-30 bp, 21-26 bp, 21-25 bp, 21-24 bp, 21-23 bp, or 21-22 bp. dsRNAs generated in the cell by processing with Dicer and similar enzymes are generally in the range of 19-22 bp in length. One strand of the duplex region of a dsDNA comprises a sequence that is substantially complementary to a region of a target RNA. The two strands forming the duplex structure can be from a single RNA molecule having at least one self-complementary region, or can be formed from two or more separate RNA molecules. Where the duplex region is formed from two strands of a single molecule, the molecule can have a duplex region separated by a single stranded chain of nucleotides (herein referred to as a "hairpin loop") between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by means other than a hairpin loop, the connecting structure is referred to as a "linker." The term "siRNA" is also used herein to refer to a dsRNA as described above.

In one aspect, an RNA interference agent includes a single stranded RNA that interacts with a target RNA sequence to direct the cleavage of the target RNA. Without wishing to be bound by theory, long double stranded RNA introduced into plants and invertebrate cells is broken down into siRNA by a Type III endonuclease known as Dicer (Sharp et al., Genes Dev. 2001, 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleaves the target to induce silencing (Elbashir, et al., (2001) Genes Dev. 15:188). Thus, in one aspect the invention relates to a single stranded RNA that promotes the formation of a RISC complex to effect silencing of the target gene.

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5' end, 3' end or both ends of either an antisense or sense strand of a dsRNA.

In one embodiment, the antisense strand of a dsRNA has a 1-10 nucleotide overhang at the 3' end and/or the 5' end. In one embodiment, the sense strand of a dsRNA has a 1-10 nucleotide overhang at the 3' end and/or the 5' end. In another embodiment, one or more of the nucleotides in the overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double-stranded over its entire length.

The term "antisense strand" or "guide strand" refers to the strand of an iRNA, e.g., a dsRNA, which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5' and/or 3' terminus.

The term "sense strand" or "passenger strand" as used herein, refers to the strand of an iRNA that includes a region that is substantially complementary to a region of the antisense strand as that term is defined herein.

The double stranded RNAs can also include double-stranded oligonucleotide wherein the two strands are linked together. The two strands can be linked to each other at both ends, or at one end only. By linking at one end is meant that 5'-end of first strand is linked to the 3'-end of the second strand or 3'-end of first strand is linked to 5'-end of the second strand. When the two strands are linked to each other at both ends, 5'-end of first strand is linked to 3'-end of second strand and 3'-end of first strand is linked to 5'-end of second strand. The two strands can be linked together by an oligonucleotide linker including, but not limited to, $(N)_n$: wherein N is independently a modified or unmodified nucleotide and n is 3-23. In some embodiments, n is 3-10. In some embodiments, the oligonucleotide linker is $(dT)_4$ or $(U)_4$.

Hairpin and dumbbell type RNAi agents will have a duplex region equal to or less than 200, 100, or 50 nucleotides in length. In some embodiments, ranges for the duplex region are 15-30, 17 to 23, 19 to 23, and 19 to 21 nucleotides pairs in length. In some embodiments, the hairpin oligonucleotides can mimic the natural precursors of microRNAs. The hairpin RNAi agents can have a single strand overhang or terminal unpaired region, in some embodiments at the 3', and in some embodiments on the antisense side of the hairpin. In some embodiments, the overhangs are 1-4, more generally 2-3 nucleotides in length. The two strands making up the hairpin structure can be arranged in any orientation. For example, the 3'-end of the antisense strand can be linked to the 5'-end of the sense strand, or the 5'-end of the antisense strand can be linked to the 3'-end of the sense strand. The hairpin oligonucleotides are also referred to as "shRNA" herein.

In some embodiments, the agent that inhibits the expression or activity of CD33 is an antisense oligonucleotide. One of skill in the art is well aware that single-stranded oligonucleotides can hybridize to a complementary target sequence and prevent access of the translation machinery to the target RNA transcript, thereby preventing protein synthesis. The single-stranded oligonucleotide can also hybridize to a complementary RNA and the RNA target can be subsequently cleaved by an enzyme such as RNase H and thus preventing translation of target RNA. Alternatively, or in addition to, the single-stranded oligonucleotide can modulate the expression of a target sequence via RISC mediated cleavage of the target sequence, i.e., the single-stranded oligonucleotide acts as a single-stranded RNAi agent. A "single-stranded RNAi agent" as used herein, is an RNAi agent which is made up of a single molecule. A single-stranded RNAi agent can include a duplexed region, formed by intra-strand pairing, e.g., it can be, or include, a hairpin or pan-handle structure.

In some embodiments, the agent that inhibits the expression or activity of CD33 is a microRNA. MicroRNAs (miRNAs or mirs) are a highly conserved class of small RNA molecules that are transcribed from DNA in the genomes of plants and animals, but are not translated into protein. Pre-microRNAs are processed into miRNAs. Processed microRNAs are single stranded ~17-25 nucleotide (nt) RNA molecules that become incorporated into the RNA-induced silencing complex (RISC) and have been identified as key regulators of development, cell proliferation, apoptosis and differentiation. They are believed to play a role in regulation of gene expression by binding to the 3'-untranslated region of specific mRNAs. RISC mediates down-regulation of gene expression through translational inhibition, transcript cleavage, or both. RISC is also implicated in transcriptional silencing in the nucleus of a wide range of eukaryotes.

The number of miRNA sequences identified to date is large and growing, illustrative examples of which can be found, for example, in: "miRBase: microRNA sequences, targets and gene nomenclature" Griffiths-Jones S, Grocock R J, van Dongen S, Bateman A, Enright A J. NAR, 2006, 34, Database Issue, D140-D144; "The microRNA Registry" Griffiths-Jones S. NAR, 2004, 32, Database Issue, D109-D111; and also on the worldwide web at http://microrna.dot.sanger.dot.ac.dot.uk/sequences/.

MiRNA mimics represent oligonucleotides that can be used to imitate the gene modulating activity of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression. miRNA mimics can be designed as mature molecules (e.g. single stranded) or mimic precursors (e.g., pri- or pre-miRNAs). In one design, miRNA mimics are double stranded molecules (e.g., with a duplex region of between about 16 and about 31 nucleotides in length) and contain one or more sequences that have identity with the mature strand of a given miRNA. Double-stranded miRNA mimics have designs similar to as described above for double-stranded oligonucleotides.

In some embodiments, the agent that inhibits the expression or activity of CD33 is a ribozyme. Ribozymes are oligonucleotides having specific catalytic domains that possess endonuclease activity (Kim and Cech, Proc Natl Acad Sci USA. 1987 December; 84(24):8788-92; Forster and Symons, Cell. 1987 Apr. 24; 49(2):211-20). At least six basic varieties of naturally-occurring enzymatic RNAs are known presently. In general, enzymatic nucleic acids act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Methods of producing a ribozyme targeted to any target sequence are known in the art. Ribozymes can be designed as described in Int. Pat. Appl. Publ. No. WO 93/23569 and Int. Pat. Appl. Publ. No. WO 94/02595, each specifically incorporated herein by reference, and synthesized to be tested in vitro and in vivo, as described therein.

Because transcription factors recognize their relatively short binding sequences, even in the absence of surrounding genomic DNA, short oligonucleotides bearing the consensus binding sequence of a specific transcription factor can be used as tools for manipulating gene expression in living cells. This strategy involves the intracellular delivery of such "decoy oligonucleotides", which are then recognized and bound by the target factor. Occupation of the transcription factor's DNA-binding site by the decoy renders the transcription factor incapable of subsequently binding to the promoter regions of target genes. Decoys can be used as therapeutic agents, either to inhibit the expression of genes that are activated by a transcription factor, or to up-regulate genes that are suppressed by the binding of a transcription factor. Examples of the utilization of decoy oligonucleotides can be found in Mann et al., J. Clin. Invest., 2000, 106: 1071-1075, which is expressly incorporated by reference herein, in its entirety.

The terms "antimir" "microRNA inhibitor" or "miR inhibitor" are synonymous and refer to oligonucleotides that interfere with the activity of specific miRNAs Inhibitors can adopt a variety of configurations including single stranded, double stranded (RNA/RNA or RNA/DNA duplexes), and hairpin designs, in general, microRNA inhibitors comprise one or more sequences or portions of sequences that are complementary or partially complementary with the mature strand (or strands) of the miRNA to be targeted, in addition, the miRNA inhibitor can also comprise additional sequences located 5' and 3' to the sequence that is the reverse complement of the mature miRNA. The additional sequences can be the reverse complements of the sequences that are adjacent to the mature miRNA in the pri-miRNA from which the mature miRNA is derived, or the additional sequences can be arbitrary sequences (having a mixture of A, G, C, U, or dT). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. MicroRNA inhibitors, when double stranded, can include mismatches between nucleotides on opposite strands.

MicroRNA inhibitors, including hairpin miRNA inhibitors, are described in detail in Vermeulen et al., "Double-Stranded Regions Are Essential Design Components Of Potent Inhibitors of RISC Function," RNA 13: 723-730 (2007) and in WO2007/095387 and WO 2008/036825 each of which is incorporated herein by reference in its entirety. A person of ordinary skill in the art can select a sequence from the database for a desired miRNA and design an inhibitor useful for the methods disclosed herein.

Unmodified oligonucleotides can be less than optimal in some applications, e.g., unmodified oligonucleotides can be prone to degradation by e.g., cellular nucleases. However, chemical modifications to one or more of the subunits of oligonucleotide can confer improved properties, e.g., can render oligonucleotides more stable to nucleases. Typical oligonucleotide modifications can include one or more of: (i) alteration, e.g., replacement, of one or both of the non-linking phosphate oxygens and/or of one or more of the linking phosphate oxygens in the phosphodiester intersugar linkage; (ii) alteration, e.g., replacement, of a constituent of the ribose sugar, e.g., of the modification or replacement of the 2' hydroxyl on the ribose sugar; (iii) wholesale replacement of the phosphate moiety; (iv) modification or replacement of a naturally occurring base with a non-natural base; (v) replacement or modification of the ribose-phosphate backbone, e.g. with peptide nucleic acid (PNA); (vi) modification of the 3' end or 5' end of the oligonucleotide; and (vii) modification of the sugar, e.g., six membered rings.

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule. As described below, modifications, e.g., those described herein, can be provided as asymmetrical modifications.

The phosphate group in the intersugar linkage can be modified by replacing one of the oxygens with a different substituent. One result of this modification to RNA phosphate intersugar linkages can be increased resistance of the oligonucleotide to nucleolytic breakdown. Examples of modified phosphate groups include phosphorothioate, phosphoroselenates, borano phosphates, borano phosphate esters, hydrogen phosphonates, phosphoroamidates, alkyl or aryl phosphonates and phosphotriesters. In some embodiments, one of the non-bridging phosphate oxygen atoms in the intersugar linkage can be replaced by a sulfur atom, e.g. phosphorothioates and phosphorodithioates. Phosphorodithioates have both non-bridging oxygens replaced by sulfur. The phosphorus center in the phosphorodithioates is achiral which precludes the formation of oligonucleotides diastereomers.

The phosphate linker can also be modified by replacement of bridging oxygen, (i.e. oxygen that links the phosphate to the nucleoside), with nitrogen (bridged phosphoroamidates), sulfur (bridged phosphorothioates), and carbon (bridged methylenephosphonates). The replacement can occur at the either one of the linking oxygens or at both linking oxygens. When the bridging oxygen is the 3'-oxygen of a nucleoside, replacement with carbon is preferred. When the bridging oxygen is the 5'-oxygen of a nucleoside, replacement with nitrogen is preferred.

Modified phosphate linkages where at least one of the oxygen linked to the phosphate has been replaced or the phosphate group has been replaced by a non-phosphorous group, are also referred to as "non-phosphodiester intersugar linkage" or "non-phosphodiester linker."

The phosphate group can be replaced by non-phosphorus containing connectors, e.g. dephospho linkers. Dephospho linkers are also referred to as non-phosphodiester linkers herein. Examples of moieties which can replace the phosphate group include, but are not limited to, amides, hydroxylamino, siloxanes, carboxamide, formacetal, methylenemethylimino (MMI). Further examples of dephospho linkers are described, for example in, Carbohydrate Modifications in Antisense Research; Y. S. Sanghvi and P. D. Cook Eds. ACS Symposium Series 580; Chapters 3 and 4, (pp. 40-65), content of which is herein incorporated by reference.

The canonical 3'-5' intersugar linkage can be replaced with a 5'-5', 3'-3', 3'-2', 2'-5', 2'-3' or 2'-2' intersugar linkage.

An oligonucleotide can include modification of all or some of the sugar groups of the nucleic acid. For example, the 2'-position of the ribose sugar can be modified, e.g., the 2'-hydroxyl group (OH) can be modified or replaced with a number of different substituents. While not being bound by theory, enhanced stability is expected since the hydroxyl can no longer be deprotonated to form a 2'-alkoxide ion. The 2'-alkoxide can catalyze degradation by intramolecular nucleophilic attack on the linker phosphorus atom. Again, while not wishing to be bound by theory, it can be desirable to some embodiments to introduce alterations in which alkoxide formation at the 2'-position is not possible. Exemplary modifications at the 2'-position include, but are not limited to, 2'-O-Me (2'-O-methyl), 2'-O-MOE (2'-O-methoxyethyl), 2'-halo (e.g., 2'-F), 2'-O-[2-(methylamino)-2-oxoethyl] (2'-O-NMA), 2'-S-methyl, 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), 2'-CN, 2'-NH$_2$, 2'-SH, and "locked" nucleic acids (LNA), in which the oxygen at the 2' position is connected by (CH$_2$)$_n$, wherein n=1-4, to the 4' carbon of the same ribose sugar, preferably n is 1 (LNA) or 2 (ENA).

Oligonucleotides can also include abasic sugars, which lack a nucleobase at C-1' or has other chemical groups in place of a nucleobase at C1'. See for example U.S. Pat. No. 5,998,203, content of which is herein incorporated in its entirety by reference. Oligonucleotides can also contain one or more sugars that are the L isomer, e.g. L-nucleosides. Modification to the sugar group can also include replacement of the 4'-O with a sulfur, optionally substituted nitrogen or CH$_2$ group.

Oligonucleotide modifications can also include acyclic nucleotides, wherein a C—C bonds between ribose carbons (e.g., C1'-C2', C2'-C3', C3'-C4', C4'-O4', C1'-O4') is absent and/or at least one of ribose carbons or oxygen (e.g., C1', C2', C3', C4' or O4') are independently or in combination absent from the nucleotide.

The 3' and 5' ends of an oligonucleotide can be modified. Such modifications can be at the 3' end, 5' end or both ends of the molecule. For example, the 3' and/or 5' ends of an oligonucleotide can be conjugated to other functional molecular entities such as labeling m An oligonucleotide can also include nucleobase (often referred to in the art simply as "base") modifications or substitutions. When a natural base is replaced by a non-natural and/or universal base, the nucleotide is said to comprise a modified nucleobase and/or a nucleobase modification herein. As used herein, "unmodified" or "natural" nucleobases include the purine bases adenine (A) and guanine (G), and the pyrimidine bases thymine (T), cytosine (C) and uracil (U). Modified nucleobases include, but are not limited to, those described in U.S. Pat. No. 3,687,808; those disclosed in the Concise Encyclopedia Of Polymer Science And Engineering, pages 858-859, Kroschwitz, J. I., ed. John Wiley & Sons, 1990; those disclosed by English et al., Angewandte Chemie, International Edition, 1991, 30, 613; those disclosed in Modified Nucleosides in Biochemistry, Biotechnology and Medicine, Herdewijin, P. Ed. Wiley-VCH, 2008; and those disclosed by Sanghvi, Y. S., Chapter 15, dsRNA Research and Applications, pages 289-302, Crooke, S. T. and Lebleu, B., Eds., CRC Press, 1993. Contents of all of the above are herein incorporated by reference. As used herein, a universal nucleobase is any modified or nucleobase that can base pair with all of the four naturally occurring nucleobases without substantially affecting the melting behavior, recognition by intracellular enzymes or activity of the oligonucleotide duplex. Some exemplary universal nucleobases include, but are not limited to, 2,4-difluorotoluene, nitropyrrolyl, nitroindolyl, 8-aza-7-deazaadenine, and structural derivatives thereof. See for example, Loakes, 2001, *Nucleic Acids Research*, 29, 2437-2447, content of which is herein incorporated by reference.

In vivo applications of oligonucleotides is limited due to presence of nucleases in the serum and/or blood. Thus in certain instances it is preferable to modify the 3', 5' or both ends of an oligonucleotide to make the oligonucleotide resistant against exonucleases. In some embodiments, the oligonucleotide comprises a cap structure at 3' (3'-cap), 5' (5'-cap) or both ends. In some embodiments, oligonucleotide comprises a 3'-cap. In another embodiment, oligonucleotide comprises a 5'-cap. In yet another embodiment, oligonucleotide comprises both a 3' cap and a 5' cap. It is to be understood that when an oligonucleotide comprises both a 3' cap and a 5' cap, such caps can be same or they can be different. As used herein, "cap structure" refers to chemical modifications, which have been incorporated at either terminus of oligonucleotide. See for example U.S. Pat. No. 5,998,203 and International Patent Publication WO03/70918, contents of which are herein incorporated in their entireties.

Exemplary 5'-caps include, but are not limited to, 5'-5'-inverted nucleotide, 5'-5'-inverted abasic nucleotide residue, and 2'-5' linkage. Exemplary 3'-caps include, but are not limited to, ligands, 3'-3'-inverted nucleotide, 3'-3'-inverted abasic nucleotide residue, 3'-2'-inverted nucleotide moiety, 3'-2'-inverted abasic moiety, and 2'-5'-linkage. For more details see Beaucage and Iyer, 1993, *Tetrahedron* 49, 1925, incorporated by reference herein.

The oligonucleotides used in accordance with this invention can be synthesized with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3, 2'-0-Methyloligoribonucleotides: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., *Helv. Chim. Acta*, 1995, 78, 486-504; Beaucage, S. L. and Iyer, R. P., *Tetrahedron*, 1992, 48, 2223-2311 and Beaucage, S. L. and Iyer, R. P., *Tetrahedron*, 1993, 49, 6123-6194, or references referred to therein. Modification described in WO 00/44895, WO01/75164, or WO02/44321 can be used herein. The disclosure of all publications, patents, and published patent applications listed herein are hereby incorporated by reference.

The preparation of phosphinate oligonucleotides is described in U.S. Pat. No. 5,508,270. The preparation of alkyl phosphonate oligonucleotides is described in U.S. Pat. No. 4,469,863. The preparation of phosphoramidite oligonucleotides is described in U.S. Pat. No. 5,256,775 or U.S. Pat. No. 5,366,878. The preparation of phosphotriester oligonucleotides is described in U.S. Pat. No. 5,023,243. The preparation of boranophosphate oligonucleotide is described in U.S. Pat. Nos. 5,130,302 and 5,177,198. The preparation of 3'-Deoxy-3'-amino phosphoramidate oligonucleotides is described in U.S. Pat. No. 5,476,925. 3'-Deoxy-3'-methylenephosphonate oligonucleotides is described in An, H, et al. *J. Org. Chem.* 2001, 66, 2789-2801. Preparation of sulfur bridged nucleotides is described in Sproat et al. *Nucleosides Nucleotides* 1988, 7,651 and Crosstick et al. *Tetrahedron Lett.* 1989, 30, 4693.

Modifications to the 2' modifications can be found in Verma, S. et al. *Annu. Rev. Biochem.* 1998, 67, 99-134 and all references therein. Specific modifications to the ribose can be found in the following references: 2'-fluoro (Kawasaki et. al., *J. Med. Chem.,* 1993, 36, 831-841), 2'-MOE (Martin, P. *Helv. Chim. Acta* 1996, 79, 1930-1938), "LNA" (Wengel, J. *Acc. Chem. Res.* 1999, 32, 301-310).

Methylenemethylimino linked oligonucleosides, also identified herein as MMI linked oligonucleosides, methylenedimethylhydrazo linked oligonucleosides, also identified herein as MDH linked oligonucleosides, and methylenecarbonylamino linked oligonucleosides, also identified herein as amide-3 linked oligonucleosides, and methyleneaminocarbonyl linked oligonucleosides, also identified herein as amide-4 linked oligonucleosides as well as mixed intersugar linkage compounds having, as for instance, alternating MMI and PO or PS linkages can be prepared as is described in U.S. Pat. Nos. 5,378,825, 5,386,023, 5,489,677 and in International Application Nos. PCT/US92/04294 and PCT/US92/04305. Formacetal and thioformacetal linked oligonucleosides can be prepared as is described in U.S. Pat. Nos. 5,264,562 and 5,264,564. Ethylene oxide linked oligonucleosides can be prepared as is described in U.S. Pat. No. 5,223,618. Siloxane replacements are described in Cormier, J. F. et al. *Nucleic Acids Res.* 1988, 16, 4583. Carbonate replacements are described in Tittensor, J. R. *J. Chem. Soc. C* 1971, 1933. Carboxymethyl replacements are described in Edge, M. D. et al. *J. Chem. Soc. Perkin Trans.* 1 1972, 1991. Carbamate replacements are described in Stirchak, E. P. Nucleic Acids Res. 1989, 17, 6129.

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They can also be prepared in accordance with U.S. Pat. No. 5,539,083.

Terminal modifications are described in Manoharan, M. et al. *Antisense and Nucleic Acid Drug Development* 12, 103-128 (2002) and references therein, content of which is herein incorporated by reference in its entirety.

Representative U.S. patents that teach the preparation of certain modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,457,191; 5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, content of each of which is herein incorporated by reference in its entirety.

A wide variety of entities, e.g., ligands, can be coupled to the oligonucleotides described herein. Ligands can include naturally occurring molecules, or recombinant or synthetic molecules. Exemplary ligands include, but are not limited to, peptides, peptidomimetics, polylysine (PLL), polyethylene glycol (PEG), mPEG, cationic groups, spermine, spermidine, polyamine, thyrotropin, melanotropin, lectin, glycoprotein, surfactant protein A, mucin, glycosylated polyaminoacids, transferrin, aptamer, immunoglobulins (e.g., antibodies), insulin, transferrin, albumin, sugar, lipophilic molecules (e.g, steroids, bile acids, cholesterol, cholic acid, and fatty acids), vitamin A, vitamin E, vitamin K, vitamin B, folic acid, B12, riboflavin, biotin, pyridoxal, vitamin cofactors, lipopolysaccharide, hormones and hormone receptors, lectins, carbohydrates, multivalent carbohydrates, radiolabeled markers, fluorescent dyes, and derivatives thereof. Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,149,782; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,672,662; 5,688,941; 5,714,166; 6,153,737; 6,172,208; 6,300,319; 6,335,434; 6,335,437; 6,395,437; 6,444,806; 6,486,308; 6,525,031; 6,528,631; 6,559,279; contents which are herein incorporated in their entireties by reference.

In general, any method of delivering a nucleic acid molecule can be adapted for use with the nucleic acid agents described herein (see e.g., Akhtar S, and Julian R L., 1992, Trends Cell. Biol. 2 (5):139-144 and WO94/02595, which are incorporated herein by reference in their entireties). However, there are three factors that are important to consider in order to successfully delivering a nucleic acid agent in vivo: (a) biological stability of the delivered molecule, (2) preventing non-specific effects, and (3) accumulation of the delivered molecule in the target tissue. The non-specific effects of a nucleic acid agent can be minimized by local administration, for example by direct injection or implantation into a tissue (as a non-limiting example, a tumor) or topically administering the preparation. Local administration to a treatment site maximizes local concentration of the agent, limits the exposure of the agent to systemic tissues that may otherwise be harmed by the agent or that can degrade the agent, and permits a lower total dose of the agent to be administered. Several studies have shown successful knockdown of gene products when an iRNA agent is administered locally. For example, intraocular delivery of a VEGF dsRNA by intravitreal injection in cynomolgus monkeys (Tolentino, M J., et al (2004) Retina 24:132-138) and subretinal injections in mice (Reich, S J., et al (2003) Mol. Vis. 9:210-216) were both shown to prevent neovascularization in an experimental model of age-related macular degeneration. In addition, direct intratumoral injection of a dsRNA in mice reduces tumor volume (Pille, J., et al (2005) Mol. Ther. 11:267-274) and can prolong survival of tumor-bearing mice (Kim, W J., et al (2006) Mol. Ther. 14:343-350; Li, S., et al (2007) Mol. Ther. 15:515-523). RNA interference has also shown success with local delivery to the CNS by direct injection (Dorn, G., et al. (2004) Nucleic Acids 32:e49; Tan, P H., et al (2005) Gene Ther. 12:59-66; Makimura, H., et al (2002) BMC Neurosci. 3:18; Shishkina, G T., et al (2004) Neuroscience 129:521-528; Thakker, E R., et al (2004) Proc. Natl. Acad. Sci. U.S.A. 101:17270-17275; Akaneya, Y., et al (2005) J. Neurophysiol. 93:594-602) and to the lungs by intranasal administration (Howard, K A., et al (2006) Mol. Ther. 14:476-484; Zhang, X., et al (2004) J. Biol. Chem. 279:10677-10684; Bitko, V., et al (2005) Nat. Med. 11:50-55). For administering a nucleic acid agent systemically for the treatment of a disease, the nucleic acid agent can be modified or alternatively delivered using a drug delivery system; both methods act to prevent the rapid degradation of the nucleic acid agent by endo- and exonucleases in vivo. In an alternative embodiment, the nucleic acid agent can be delivered using drug delivery systems such as a nanoparticle, a dendrimer, a polymer, liposomes, or a cationic delivery system. Positively charged cationic delivery systems facilitate binding of a nucleic acid molecule (negatively charged) and also enhance interactions at the negatively charged cell membrane to permit efficient uptake of the nucleic acid agent by the cell. Cationic lipids, dendrimers, or polymers can either be bound to a nucleic acid agent, or induced to form a vesicle or micelle (see e.g., Kim S H., et al (2008) Journal of Controlled Release 129 (2): 107-116) that encases a nucleic acid agent. The formation of vesicles or micelles further prevents degradation of the nucleic acid agent when administered systemically. Methods for making and administering cationic-nucleic acid complexes are well within the abilities of one skilled in the art (see e.g., Sorensen, D R., et al (2003) J. Mol. Biol. 327: 761-766; Verma, U N., et al (2003) Clin. Cancer Res. 9:1291-1300; Arnold, A S et al (2007) J. Hypertens. 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) Nature 441:111-114), cardiolipin (Chien, P Y., et al (2005) Cancer Gene Ther. 12:321-328; Pal, A., et al (2005) Int J. Oncol. 26:1087-1091), polyethyleneimine (Bonnet M E., et al (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al (2007) Biochem. Soc. Trans. 35:61-67; Yoo, H., et al (1999) Pharm. Res. 16:1799-1804). In some embodiments, an iRNA forms a complex with cyclodextrin for systemic administration. Methods for administration and pharmaceutical compositions of nucleic acids and cyclodextrins can be found in U.S. Pat. No. 7,427,605, which is herein incorporated by reference in its entirety.

In another aspect, a nucleic acid agent that inhibits the expression or activity of CD33 can be expressed from transcription units inserted into DNA or RNA vectors (see, e.g., Couture, A, et al., *TIG.*, 1996, 12:5-10; Skillern, A., et al., International PCT Publication No. WO 00/22113, Conrad, PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA*, 1995, 92:1292).

The individual strand or strands of a dsRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

RNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell. Vectors are described below in more detail.

In some embodiments, the agent that inhibits the expression or activity of CD33 is a small molecule. For example, irreversible or reversible inhibitors of CD33 can be used in the methods disclosed herein. As used herein, the term "small molecule" refers to natural or synthetic molecules having a molecular weight less than about 10,000 grams per mole, organic or inorganic compounds having a molecular weight less than about 5,000 grams per mole, than about 1,000 grams per mole, or less than about 500 grams per mole.

In some embodiments, the agent that inhibits the expression or activity of CD33 is a sialic acid analogue or a sialic acid derivative.

In some embodiments, the agent that inhibits the expression or activity of can be an antibody molecule or the epitope-binding moiety of an antibody molecule. For example the agent can be selected from monoclonal, chimeric, humanized, and recombinant antibodies and antigen-binding fragments thereof. In some embodiments, neutralizing antibodies can be used as inhibitors of CD33. Antibodies are readily raised in animals such as rabbits or mice by immunization with the antigen. Immunized mice are particularly useful for providing sources of B cells for the manufacture of hybridomas, which in turn are cultured to produce large quantities of monoclonal antibodies.

Antibodies provide high binding avidity and unique specificity to a wide range of target antigens and haptens. Monoclonal antibodies useful in the practice of the methods disclosed herein include whole antibody and fragments thereof and are generated in accordance with conventional techniques, such as hybridoma synthesis, recombinant DNA techniques and protein synthesis.

Useful monoclonal antibodies and fragments can be derived from any species (including humans) or can be formed as chimeric proteins which employ sequences from more than one species. Human monoclonal antibodies or "humanized" murine antibody are also used in accordance with the present invention. For example, murine monoclonal antibody can be "humanized" by genetically recombining the nucleotide sequence encoding the murine Fv region (i.e., containing the antigen binding sites) or the complementarily determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction the possibly of adverse immune reactions in a manner similar to that disclosed in European Patent Application No. 0,411,893 A2. The murine monoclonal antibodies should preferably be employed in humanized form. Antigen binding activity is determined by the sequences and conformation of the amino acids of the six complementarily determining regions (CDRs) that are located (three each) on the light and heavy chains of the variable portion (Fv) of the antibody. The 25-kDa single-chain Fv (scFv) molecule, composed of a variable region (VL) of the light chain and a variable region (VH) of the heavy chain joined via a short peptide spacer sequence, is the smallest antibody fragment developed to date. Techniques have been developed to display scFv molecules on the surface of filamentous phage that contain the gene for the scFv. scFv molecules with a broad range of antigenic-specificities can be present in a single large pool of scFv-phage library. Some examples of high affinity monoclonal antibodies and chimeric derivatives thereof, useful in the methods of the present invention, are described in the European Patent Application EP 186,833; PCT Patent Application WO 92/16553; and U.S. Pat. No. 6,090,923.

Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined.

One limitation of scFv molecules is their monovalent interaction with target antigen. One of the easiest methods of improving the binding of a scFv to its target antigen is to increase its functional affinity through the creation of a multimer. Association of identical scFv molecules to form diabodies, triabodies and tetrabodies can comprise a number of identical Fv modules. These reagents are therefore multivalent, but monospecific. The association of two different scFv molecules, each comprising a VH and VL domain derived from different parent Ig will form a fully functional bispecific diabody. A unique application of bispecific scFvs is to bind two sites simultaneously on the same target molecule via two (adjacent) surface epitopes. These reagents gain a significant avidity advantage over a single scFv or Fab fragments. A number of multivalent scFv-based structures has been engineered, including for example, miniantibodies, dimeric miniantibodies, minibodies, (scFv)$_2$, diabodies and triabodies. These molecules span a range of valence (two to four binding sites), size (50 to 120 kDa), flexibility and ease of production. Single chain Fv antibody fragments (scFvs) are predominantly monomeric when the VH and VL domains are joined by, polypeptide linkers of at least 12 residues. The monomer scFv is thermodynamically stable with linkers of 12 and 25 amino acids length under all conditions. The noncovalent diabody and triabody molecules are easy to engineer and are produced by shortening the peptide linker that connects the variable heavy and variable light chains of a single scFv molecule. The scFv dimers are joined by amphipathic helices that offer a high degree of flexibility and the miniantibody structure can be modified to create a dimeric bispecific (DiBi) miniantibody that contains two miniantibodies (four scFv molecules) connected via a double helix. Gene-fused or disulfide bonded scFv dimers provide an intermediate degree of flexibility and are generated by straightforward cloning techniques adding a C-terminal Gly4Cys sequence. scFv-CH3 minibodies are comprised of two scFv molecules joined to an IgG CH3 domain either directly (LD minibody) or via a very flexible hinge region (Flex minibody). With a molecular weight of approximately 80 kDa, these divalent constructs are capable of significant binding to antigens. The Flex minibody exhibits impressive tumor localization in mice. Bi- and tri-specific multimers can be formed by association of different scFv molecules. Increase in functional affinity can be reached when Fab or single chain Fv antibody fragments (scFv) fragments are complexed into dimers, trimers or larger aggregates. The most important advantage of multivalent scFvs over monovalent scFv and Fab fragments is the gain in functional binding affinity (avidity) to target antigens. High avidity requires that scFv multimers are capable of binding simultaneously to separate target antigens. The gain in functional affinity for scFv diabodies compared to scFv monomers is significant and is seen primarily in reduced off-rates, which result from multiple binding to two or more target antigens and to rebinding when one Fv dissociates. When such scFv molecules associate into multimers, they can be designed with either high avidity to a single target antigen or with multiple specificities to different target antigens. Multiple binding to antigens is dependent on correct alignment and orientation in the Fv modules. For full avidity in multivalent scFvs target, the antigen binding sites must point towards the same direction. If multiple binding is not sterically possible then apparent gains in functional affinity are likely to be due the effect of increased rebinding, which is dependent on diffusion rates and antigen concentration. Antibodies conjugated with moieties that improve their properties are also contemplated for the instant invention. For example, antibody conjugates with PEG that increases their half-life in vivo can be used for the present invention. Immune libraries are prepared by subjecting the genes encoding variable antibody fragments from the B lymphocytes of naive or immunized animals or patients to PCR amplification. Combinations of oligonucleotides which are specific for immunoglobulin genes or for the immunoglobulin gene families are used. Immunoglobulin germ line genes can be used to prepare semisynthetic antibody repertoires, with the complementarity-determining region of the variable fragments being amplified by PCR using degenerate primers. These single-pot libraries have the advantage that antibody fragments against a large number of antigens can be isolated from one single library. The phage-display technique can be used to increase the affinity of antibody fragments, with new libraries being prepared from already existing antibody fragments by random, codon-based or site-directed mutagenesis, by shuffling the chains of individual domains with those of fragments from naive repertoires or by using bacterial mutator strains.

Alternatively, a SCID-hu mouse, for example the model developed by Genpharm, can be used to produce antibodies, or fragments thereof. In one embodiment, a new type of high avidity binding molecule, termed peptabody, created by harnessing the effect of multivalent interaction is contemplated. A short peptide ligand was fused via a semirigid hinge region with the coiled-coil assembly domain of the cartilage oligomeric matrix protein, resulting in a pentameric multivalent binding molecule. In preferred embodiment of this invention, ligands and/or chimeric inhibitors can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. Alternatively, two or more active agents and or inhibitors attached to targeting moieties can be administered, wherein each conjugate includes a targeting moiety, for example, a different antibody. Each antibody is reactive with a different target site epitope (associated with the same or a different target site antigen). The different antibodies with the agents attached accumulate additively at the desired target site. Antibody-based or non-antibody-based targeting moieties can be employed to deliver a ligand or the inhibitor to a target site. Preferably, a natural binding agent for an unregulated or disease associated antigen is used for this purpose.

In some embodiments, the antibody comprises the amino acid sequence SEQ ID NO: 1.

In some embodiments, the methods disclosed herein comprise administering a CD33 protein lacking the sialic acid binding domain (i.e., a non-sialic CD33 protein) to the subject. The Ig-V typically mediates sialic acid binding in CD33. Thus, the IG-V domain in the non-sialic CD polypeptide is altered or modified such that the non-sialic CD33 protein does not bind sialic acid or the binding is decreased or reduced relative to the full length CD33 protein. The Ig-V domain can be completely absent in the non-sialic CD33 protein or comprises one or more mutations and/or deletions such that its (Ig-V domain) ability to bind sialic acid is decreased, reduced or abolished.

Peptide modifications are well known in the art. Thus, a non-sialic CD33 protein disclosed herein can comprise one or more peptide modifications known in the art. Exemplary peptide modifications for modifying the non-sialic CD33 protein include, but are not limited to, D amino acids, α amino acids, β amino acids, non-amide or modified amide linkages, chemically modified amino acids, naturally occurring non-proteogenic amino acids, rare amino acids, chemically synthesized compounds that have properties known in the art to be characteristic of an amino acid, and the like. In some embodiments the non-sialic CD33 protein comprises at least one (e.g. two, three, four, five, six, seven, eight, nine, ten or more) peptide modifications.

In some embodiments, the non-sialic CD33 protein comprises at least one (e.g., 1, 2, 3, 4, 5, 6, 7, 8, 9, 10 or more) amino acid selected from the group consisting of homocysteine, phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine (3-mercapto-D-valine), ornithine, citruline, alpha-methyl-alanine, para-benzoylphenylalanine, para-amino phenylalanine, p-fluorophenylalanine, phenylglycine, propargylglycine, sarcosine, and tert-butylglycine), diaminobutyric acid, 7-hydroxy-tetrahydroisoquinoline carboxylic acid, naphthylalanine, biphenylalanine, cyclohexylalanine, amino-isobutyric acid, norvaline, norleucine, tert-leucine, tetrahydroisoquinoline carboxylic acid, pipecolic acid, phenylglycine, homophenylalanine, cyclohexylglycine, dehydroleucine, 2,2-diethylglycine, 1-amino-1-cyclopentanecarboxylic acid, 1-amino-1-cyclohexanecarboxylic acid, amino-benzoic acid, amino-naphthoic acid, gamma-aminobutyric acid, difluorophenylalanine, nipecotic acid, alpha-amino butyric acid, thienyl-alanine, t-butylglycine, and derivatives thereof.

In some embodiments, the non-sialic CD33 protein comprises at least one (e.g., 1, 2, 3, 4, 5, 6, 7, 8, 9, 10 or more) D-amino acid. When more than one D-amino acid is present in the non-sialic CD33 protein, they can be positioned next to or not next to each other.

The non-sialic CD33 protein can also comprise one or more (e.g., 1, 2, 3, 4, 5, 6, 7, 8, 9, 10 or more) of beta-amino acids. When more than one beta-amino acid is present in the non-sialic CD33 protein, they can be positioned next to each other or next to another amino acid.

In some embodiments, the non-sialic CD33 protein comprises at least one (e.g., 1, 2, 3, 4, 5, 6, 7, 8, 9, 10 or more) peptide bond replacement to make a more stable protein. Exemplary peptide bond replacements include, but are not limited to, urea, thiourea, carbamate, sulfonyl urea, trifluoroethylamine, ortho-(aminoalkyl)-phenylacetic acid, para-(aminoalkyl)-phenylacetic acid, meta-(aminoalkyl)-phenylacetic acid, thioamide, tetrazole, boronic ester, and olefinic group. One or more of the peptide bonds of in the non-sialic CD33 protein can be replaced with a peptide bond replacement. The peptide bond can also be replaced by a linker. When more than one peptide bond replacement is present in the non-sialic CD33 protein, they can be positioned next to each other or next to unmodified peptide bond.

The choice of including a modification in the non-sialic CD33 protein depends, in part, on the desired characteristics of the non-sialic CD33 protein. For example, the incorporation of one or more (D)-amino acids can confer increasing stability on the non-sialic CD33 protein in vitro or in vivo, thus affecting shelf-life, serum half-life or bioavailability. The incorporation of one or more (D)-amino acids also can increase or decrease the binding activity of the non-sialic CD33 protein as determined, for example, using the binding assays by methods well known in the art. In some cases it is desirable to design a non-sialic CD33 protein which retains activity for a longer period of time, for example, when designing a peptide to administer to a subject. In these cases, the incorporation of one or more (D)-amino acids or replacement of amide backbone linkages in the non-sialic CD33 protein can stabilize the non-sialic CD33 protein against endogenous peptidases in vivo, thereby prolonging the subject's exposure to the non-sialic CD33 protein.

The non-sialic CD33 proteins of the present invention can be synthesized by using well known methods including recombinant methods and chemical synthesis. Recombinant methods of producing a peptide through the introduction of a vector including nucleic acid encoding the peptide into a suitable host cell is well known in the art, such as is described in Sambrook et al., Molecular Cloning: A Laboratory Manual, 4$^{th}$ Ed, Vols 1 to 3, Cold Spring Harbor, N.Y. (2012); M. W. Pennington and B. M. Dunn, Methods in Molecular Biology: Peptide Synthesis Protocols, Vol 35, Humana Press, Totawa, N.J. (1994), contents of both of which are herein incorporated by reference. Peptides can also be chemically synthesized using methods well known in the art. See for example, Merrifield et al., J. Am. Chem. Soc. 85:2149 (1964); Bodanszky, M., Principles of Peptide Synthesis, Springer-Verlag, New York, N.Y. (1984); Kimmerlin, T. and Seebach, D. J. Pept. Res. 65:229-260 (2005); Nilsson et al., Annu Rev. Biophys. Biomol. Struct. (2005) 34:91-118; W. C. Chan and P. D. White (Eds.) Fmoc Solid Phase Peptide Synthesis: A Practical Approach, Oxford University Press, Cary, N.C. (2000); N. L. Benoiton, Chemistry of Peptide Synthesis, CRC Press, Boca Raton, Fla. (2005); J. Jones, Amino Acid and Peptide Synthesis, 2$^{nd}$ Ed, Oxford University Press, Cary, N.C. (2002); and P. Lloyd-Williams, F. Albericio, and E. Giralt, Chemical Approaches to the synthesis of peptides and proteins, CRC Press, Boca Raton, Fla. (1997), contents of all of which are herein incorporated by reference. Peptide derivatives can also be prepared as described in U.S. Pat. Nos. 4,612,302; 4,853,371; and 4,684, 620, and U.S. Pat. App. Pub. No. 2009/0263843, contents of all which are herein incorporated by reference.

Newly synthesized the non-sialic CD33 proteins can be purified, for example, by high performance liquid chromatography (HPLC), and can be characterized using, for example, mass spectrometry or amino acid sequence analysis.

In some embodiments, the non-sialic CD33 protein comprises the amino acid sequence: mpllllpll wadlthrpki lipgtlepgh sknitcsysw aceqgtppif swlsaaptsl gprtthssvl iitprpqdhg tnitcqvkfa gagvtterti qlnvtyvpqn pttgifpgdg sgkqetragv vhgaiggagv tallalcicl iffivkthrr kaartavgrn dthpttgsas pkhqkksklh gptetsscsg aaptvemdee lhyaslnfhg mnpskdtste ysevrtq (SEQ ID NO: 8).

In one embodiment, the non-sialic CD33 protein comprises an amino acid sequence SEQ ID NO: 2, wherein at least one amino acid is deleted, modified, or replaced by a different amino acid, such that binding of sialic acid to the non-sialic CD33 protein is decreased, reduced or abolished.

In some embodiments, the non-sialic CD33 protein can be administered to the subject by administering a nucleic acid encoding or expressing the non-sialic CD33 protein to the subject. In one embodiment, the nucleic acid encoding the non-sialic CD33 protein comprises the nucleotide sequence:

(SEQ ID NO: 9)

```
CAGACATGCCGCTGCTGCTACTGCTGCCCCTGCTGTGGGCAGACTTGACC

CACAGGCCCAAAATCCTCATCCCTGGCACTCTAGAACCCGGCCACTCCAA

AAACCTGACCTGCTCTGTGTCCTGGGCCTGTGAGCAGGGAACACCCCCGA

TCTTCTCCTGGTTGTCAGCTGCCCCCACCTCCCTGGGCCCCAGGACTACT

CACTCCTCGGTGCTCATAATCACCCCACGGCCCCAGGACCACGGCACCAA

CCTGACCTGTCAGGTGAAGTTCGCTGGAGCTGGTGTGACTACGGAGAGAA

CCATCCAGCTCAACGTCACCTATGTTCCACAGAACCCAACAACTGGTATC

TTTCCAGGAGATGGCTCAGGGAAACAAGAGACCAGAGCAGGAGTGGTTCA

TGGGGCCATTGGAGGAGCTGGTGTTACAGCCCTGCTCGCTCTTTGTCTCT

GCCTCATCTTCTTCATAGTGAAGACCCACAGGAGGAAAGCAGCCAGGACA

GCAGTGGGCAGGAATGACACCCACCCTACCACAGGGTCAGCCTCCCCGAA

ACACCAGAAGAAGTCCAAGTTACATGGCCCCACTGAAACCTCAAGCTGTT

CAGGTGCCGCCCCTACTGTGGAGATGGATGAGGAGCTGCATTATGCTTCC

CTCAACTTTCATGGGATGAATCCTTCCAAGGACACCTCCACCGAATACTC

AGAGGTCAGGACCCAGTGAGGAACCCACAAGAGCATCAGGCTCAGCTAGA

AGATCCACATCCTCTACAGGTCGGGGACCAAAGGCTGATTCTTGGAGATT

TAACACCCCACAGGCAATGGGTTTATAGACATTATGTGAGTTTCCTGCTA

TATTAACATCATCTTAGACTTTGCAAGCAGAGAGTCGTGGAATCAAATCT

GTGCTCTTTCATTTGCTAAGTGTATGATGTCACACAAGCTCCTTAACCTT

CCATGTCTCCATTTTCTTCTCTGTGAAGTAGGTATAAGAAGTCCTATCTC

ATAGGGATGCTGTGAGCATTAAATAAAGGTACACATGGAAAACAAAAAAA

AAAAAAAAAAAAAAAAAAAAAAAAAAAAAAAAAAAAAAAAAAAAAAAAAA

AAAAAAAAAAAAAAAAAAAAAAAAAAA.
```

In some embodiments, the nucleic acid encoding the non-sialic CD33 protein is a modified RNA. It has been demonstrated that modified RNA can be used for rapid and efficient protein expression endogenously. In addition, modified RNA is advantageous in that it can result in a reduced innate immune response relative to a similar RNA without the modifications. Technologies for modified RNA are disclosed in WO2012138453 and US20120322865, the content of each of which is incorporated herein in its entirety.

In some embodiments, the nucleic acid encoding the non-sialic CD33 protein is a vector that encodes and directs the expression of the non-sialic CD33 protein.

As used herein, the term "vector" refers to a polynucleotide sequence suitable for transferring transgenes into a host cell. The term "vector" includes plasmids, mini-chromosomes, phage, naked DNA and the like. See, for example, U.S. Pat. Nos. 4,980,285; 5,631,150; 5,707,828; 5,759,828; 5,888,783 and, 5,919,670, and, Sambrook et al, *Molecular Cloning: A Laboratory Manual,* 2nd Ed., Cold Spring Harbor Press (1989). One type of vector is a "plasmid," which refers to a circular double stranded DNA loop into which additional DNA segments are ligated. Another type of vector is a viral vector, wherein additional DNA segments are ligated into the viral genome. Certain vectors are capable of autonomous replication in a host cell into which they are introduced (e.g., bacterial vectors having a bacterial origin of replication and episomal mammalian vectors). Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" is used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A cloning vector is one which is able to replicate autonomously or integrated in the genome in a host cell, and which is further characterized by one or more endonuclease restriction sites at which the vector may be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host cell such as a host bacterium or just a single time per host before the host reproduces by mitosis. In the case of phage, replication can occur actively during a lytic phase or passively during a lysogenic phase.

An expression vector is one into which a desired DNA sequence can be inserted by restriction and ligation such that it is operably joined to regulatory sequences and can be expressed as an RNA transcript. Vectors can further contain one or more marker sequences suitable for use in the identification of cells which have or have not been transformed or transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). In certain embodiments, the vectors used herein are capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. A variety of conditional promoters also can be used, such as promoters controlled by the presence or absence of a molecule.

The precise nature of the regulatory sequences needed for gene expression can vary between species or cell types, but in general can include, as necessary, 5'-non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences can also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., Molecular Cloning: A Laboratory Manual, $4^{th}$ Ed, Vols 1 to 3, Cold Spring Harbor, N.Y. (2012).

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g EPV and EBV vectors. Constructs for the recombinant expression of an iRNA will generally require regulatory elements, e.g., promoters, enhancers, etc., to ensure the expression of CD33 protein in target cells. Other aspects to consider for vectors and constructs are further described below.

Vectors useful for the delivery of the non-sialic CD33 protein or the nucleic acid agent will include regulatory elements (promoter, enhancer, etc.) sufficient for expression of the CD33 protein or the nucleic acid agent in the desired target cell or tissue. The regulatory elements can be chosen to provide either constitutive or regulated/inducible expression.

Expression of the non-sialic CD33 protein or the nucleic acid can be precisely regulated, for example, by using an inducible regulatory sequence that is sensitive to certain physiological regulators, e.g., circulating glucose levels, or hormones (Docherty et al., 1994, FASEB J. 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

In a specific embodiment, viral vectors that contain nucleic acid sequences encoding the non-sialic CD33 protein or the nucleic acid agent can be used. For example, a retroviral vector can be used. These retroviral vectors contain the components necessary for the correct packaging of the viral genome and integration into the host cell DNA. More detail about retroviral vectors can be found, for example, in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of non-sialic CD33 proteins or the nucleic acid agents. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995).

Use of Adeno-associated virus (AAV) vectors is also contemplated (Walsh et al., Proc. Soc. Exp. Biol. Med. 204:289-300 (1993); U.S. Pat. No. 5,436,146). In one embodiment, the CD33 protein can be expressed from a recombinant AAV vector having, for example, either the U6 or H1 RNA promoters, or the cytomegalovirus (CMV) promoter. Suitable AAV vectors for expressing the CD33 protein, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat.

No. 5,252,479; U.S. Pat. No. 5,139,941; International Patent Application No. WO 94/13788; and International Patent Application No. WO 93/24641, the entire disclosures of which are herein incorporated by reference.

Another preferred viral vector is a pox virus such as a vaccinia virus, for example an attenuated vaccinia such as Modified Virus Ankara (MVA) or NYVAC, an avipox such as fowl pox or canary pox.

The agents that inhibits the expression or activity of CD33 or expression vectors can be provided in pharmaceutically acceptable compositions. These pharmaceutically acceptable compositions comprise a therapeutically-effective amount of the agent formulated together with one or more pharmaceutically acceptable carriers (additives) and/or diluents. As described in detail below, the pharmaceutical compositions of can be pecially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, agents can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. For example, an amount of a compound administered to a subject that is sufficient to produce a statistically significant, measurable change in at least one symptom of cancer or metastasis.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices are preferred. As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized.

The therapeutically effective dose can be estimated initially from cell culture assays. A dose can be formulated in animal models to achieve a circulating plasma concentration range that includes the 1050 (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay.

The dosage can be determined by a physician and adjusted, as necessary, to suit observed effects of the treatment. Generally, the compositions are administered so that the agent is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 tmg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that the agent has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In some embodiments, the agent (e.g., a nucleic acid agent or an expression vector) can be formulated as a liposome. There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to traverse intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent can act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE).

Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. S.T.P.Pharma. Sci., 1994, 4(6):466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside $G_{M1}$, galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside GM1 or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{1215G}$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534, 899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describes PEG-containing liposomes that can be further derivatized with functional moieties on their surfaces.

A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes can include a dsRNA. U.S. Pat. No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

In some embodiments, the agent (e.g., a nucleic acid agent or an expression vector) can be fully encapsulated in the lipid formulation, e.g., to form a SPLP, pSPLP, SNALP, or other nucleic acid-lipid particle. As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

In one embodiment, the lipid to drug ratio (mass/mass ratio) (e.g., lipid to nucleic acid) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1.

The cationic lipid can be, for example, N,N-dioleyl-N,N-dimethylammonium chloride (DODAC), N,N-distearyl-N,N-dimethylammonium bromide (DDAB), N-(1-(2,3-dioleoyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.C1), 1,2-Dilinoleoyl-3-trimethylaminopropane chloride salt (DLin-TAP.C1), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech Gi), or a mixture thereof. The cationic lipid can comprise from about 20 mol % to about 50 mol % or about 40 mol % of the total lipid present in the particle.

The non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($Ci_2$), a PEG-dimyristyloxypropyl ($Ci_4$), a PEG-dipalmityloxypropyl ($C_{16}$), or a PEG-distearyloxypropyl ($C_{18}$). The conjugated lipid that prevents aggregation of particles can be from 0 mol % to about 20 mol % or about 2 mol % of the total lipid present in the particle.

In some embodiments, the agents (e.g. nucleic acid agents or expression vectors) can be prepared and formulated as emulsions. Emulsions are typically heterogeneous systems of one liquid dispersed in another in the form of droplets usually exceeding 0.1 µm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials is also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment the agents can be formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191, 105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection. In some embodiments, the compound is administered directly into the central nervous system.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, at least one symptom of a disease or disorder is alleviated by at least 5%, at least 10%, at least 20%, at least 30%, at least 40%, or at least 50%.

The term "treatment", with respect to treatment of Alzheimer's disease or a disease associated with Aβ accumulation or aggregation refers to, inter alia, preventing the development of the disease, or altering the course of the disease (for example, but not limited to, slowing the progression of the disease), or reversing a symptom of the disease or reducing one or more symptoms and/or one or more biochemical markers in a subject, preventing one or more symptoms from worsening or progressing, promoting recovery or improving prognosis, and/or preventing disease in a subject who is free therefrom as well as slowing or reducing progression of existing disease. For a given subject, improvement in a symptom, its worsening, regression, or progression can be determined by an objective or subjective measure. Modification of one or more biochemical markers or presence of beta amyloid in the CSF for example can be measured. For example, but not limited to, a reduction in a biochemical marker of Alzheimer's disease, for example a reduction in amyloid plaque deposition by 10%, or a reduction in the activation of glial cells, for example a reduction in cells expressing GFAP by 10%, would be considered effective treatments by the methods as disclosed herein. As alternative examples, a reduction in a symptom, for example, a slowing of the rate of memory loss by 10% or a cessation of the rate memory decline, or a reduction in memory loss by 10% or an improvement in memory by 10% would also be considered as affective treatments by the methods as disclosed herein.

Further, as used herein, the terms "treat" or "treatment" refer to both therapeutic treatment and prophylactic or preventative measures, wherein the object is to prevent or slow down (lessen) an undesired physiological change or disorder, such as the progression of Alzheimer's disease. Beneficial or desired clinical results can include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Any particular treatment regimen can provide one or more such clinical results in one or more patients, and need not provide all such clinical results. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of neuro-inflammatory disorders.

In addition, the methods described herein can be used to treat domesticated animals and/or pets. A subject can be male or female. A subject can be one who has been previously diagnosed with or identified as suffering from or having neuro-inflammatory disease or disorder, but need not have already undergone treatment.

Alzheimer's Disease

Alzheimer's disease (AD) is a progressive disease resulting in senile dementia. See generally Selkoe, TINS 16, 403-409 (1993); Hardy et al., WO 92/13069; Selkoe, J. Neuropathol. Exp. Neurol. 53, 438-447 (1994); Duff et al., Nature 373, 476-477 (1995); Games et al., Nature 373, 523 (1995). Broadly speaking the disease falls into two categories: late onset, which occurs in old age (65+ years) and early onset, which develops well before the senile period, i.e, between 35 and 60 years. In both types of disease, the pathology is the same but the β abnormalities tend to be more severe and widespread in cases beginning at an earlier age. The disease is characterized at the macroscopic level by significant brain shrinkage away from the cranial vault as seen in MRI images as a direct result of neuronal loss and by two types of macroscopic lesions in the brain, senile plaques and neurofibrillary tangles. Senile plaques are areas comprising disorganized neuronal processes up to 150 µm across and extracellular amyloid deposits, which are typically concentrated at the center and visible by microscopic analysis of sections of brain tissue. Neurofibrillary tangles are intracellular deposits of tau protein consisting of two filaments twisted about each other in pairs.

The principal constituent of the plaques is a peptide termed Aβ or β-amyloid peptide. Aβ peptide is an internal fragment of 39-43 amino acids of a precursor protein termed amyloid precursor protein (APP). Several mutations within the APP protein have been correlated with the presence of Alzheimer's disease. See, e.g., Goate et al., Nature 349, 704) (1991) (valine$^{717}$ to isoleucine); Chartier Harlan et al. Nature 353, 844 (1991)) (valine$^{717}$ to glycine); Murrell et al., Science 254, 97 (1991) (valine$^{717}$ to phenylalanine); Mullan et al., glycine); Murrell et al., Science 254, 97 (1991) (valine$^{717}$ to phenylalanine); Mullan et al., Nature Genet. 1, 345 (1992) (a double mutation changing lysine$^{595}$-methionine$^{596}$ to asparagine$^{595}$-leucine$^{596}$). Such mutations are thought to cause Alzheimer's disease by increased or altered processing of APP to Aβ, particularly processing of APP to increased amounts of the long form of Aβ (i.e., Aβ1-42 and Aβ1-43). Mutations in other genes, such as the presenilin genes, PS1 and PS2, are thought indirectly to affect processing of APP to generate increased amounts of long form Aβ (see Hardy, TINS 20, 154 (1997)). These observations indicate that Aβ, and particularly its long form, is a causative element in Alzheimer's disease.

Aβ, also known as β-amyloid peptide, or A4 peptide (see U.S. Pat. No. 4,666,829; Glenner & Wong, Biochem. Biophys. Res. Commun. 120, 1131 (1984)), is a peptide of 39-43 amino acids, is the principal component of characteristic plaques of Alzheimer's disease. Aβ is generated by processing of a larger protein APP by two enzymes, termed β and γ secretases (see Hardy, TINS 20, 154 (1997)). Known mutations in APP associated with Alzheimer's disease occur proximate to the site of β or γ-secretase, or within Aβ. For example, position 717 is proximate to the site of γ-secretase cleavage of APP in its processing to Aβ, and positions 670/671 are proximate to the site of β-secretase cleavage. It is believed that the mutations cause AD disease by interacting with the cleavage reactions by which Aβ is formed so as to increase the amount of the 42/43 amino acid form of Aβ generated.

Aβ has the unusual property that it can fix and activate both classical and alternate complement cascades. In particular, it binds to C1q and ultimately to C3bi. This association facilitates binding to macrophages leading to activation of B cells. In addition, C3bi breaks down further and then binds to CR2 on B cells in a T cell dependent manner leading to a 10,000 increase in activation of these cells. This mechanism causes Aβ to generate an immune response in excess of that of other antigens.

Most therapeutic strategies for Alzheimer's disease are aimed at reducing or eliminating the deposition of Aβ42 in the brain, typically via reduction in the generation of Aβ42 from APP and/or some means of lowering existing Aβ42 levels from sources that directly contribute to the deposition of this peptide in the brain (De Felice and Ferreira, 2002). A partial list of aging-associated causative factors in the development of sporadic Alzheimer's disease includes a shift in the balance between Aβ peptide production and its clearance from neurons that favors intracellular accumulation, increased secretion of Aβ peptides by neurons into the surrounding extracellular space, increased levels of oxidative damage to these cells, and global brain hypoperfusion and the associated compensatory metabolic shifts in affected.

The Aβ42 that deposits within neurons and plaques could also originate from outside of the neurons (exogenous Aβ42) during Alzheimer's disease pathogenesis. Levels of soluble Aβ peptides in the blood are known to be much higher than in the interstitial space and CSF in the brains of healthy individuals with blood as a source of exogenous Aβ peptides that eventually deposit in the Alzheimer's disease brain. However, except for trace amounts of Aβ that are actively transported across endothelial cells, it is well-known that access of blood-borne Aβ peptides to brain tissue in normal healthy individuals is effectively blocked by the integrity of the blood-brain barrier (BBB).

Genetic markers of risk toward Alzheimer's disease include mutations in the APP gene, particularly mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of Alzheimer's disease, hypercholesterolemia or atherosclerosis. Subjects presently suffering from Alzheimer's disease can be recognized from characteristic dementia, as well as the presence of risk factors described above. In addition, a number of diagnostic tests are available for identifying subjects who have Alzheimer's disease. These include measurement of CSF tau and Aβ42 levels. Elevated tau and increased Aβ42 levels signify the presence of Alzheimer's disease. Individuals suffering from Alzheimer's disease can also be diagnosed by MMSE or ADRDA criteria. The tissue sample for analysis is typically blood, plasma, serum, mucus or cerebral spinal fluid from the patient. The sample is analyzed for indicia of an immune response to any forms of Aβ peptide, typically Aβ42. The immune response can be determined from the presence of, e.g., antibodies or T-cells that specifically bind to Aβ peptide. ELISA methods of detecting antibodies specific to Aβ are described in the Examples section.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time.

Methods to Identify Subjects for Risk of or Having Alzheimer's Disease.

Subjects amenable to treatment using the methods as disclosed herein include subjects at risk of a neurodegenerative disease, for example Alzheimer's Disease but not showing symptoms, as well as subjects showing symptoms of the neurodegenerative disease, for example subjects with symptoms of Alzheimer's Disease. Subjects can be screened for their likelihood of having or developing Alzheimer's Disease based on a number of biochemical and genetic markers.

One can also diagnose a subject with increased risk of developing Alzheimer's Disease using genetic markers for Alzheimer's Disease. Genetic abnormality in a few families has been traced to chromosome 21 (St. George-Hyslop et al., Science 235:885-890, 1987). One genetic marker is, for example mutations in the APP gene, particularly mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of Alzheimer's Disease, hypercholesterolemia or atherosclerosis. Subjects with APP, PS1 or PS2 mutations are highly likely to develop Alzheimer's disease. ApoE is a susceptibility gene, and subjects with the e4 isoform of ApoE (ApoE4 isoform) have an increased risk of developing Alzheimer's disease. Test for subjects with ApoE4 isoform are disclosed in U.S. Pat. No. 6,027,896, which is incorporated in its entirety herein by reference. Other genetic links have been associated with increased risk of Alzheimer's disease, for example variances in the neuronal sortilinrelated receptor SORL1 may have increased likelihood of developing late-onset Alzheimer's disease (Rogaeva at al., Nat Genet. 2007 February; 39(2):168-77). Other potential Alzheimer disease susceptibility genes, include, for example ACE, CHRNB2, CST3, ESR1, GAPDHS, IDE, MTHFR, NCSTN, PRNP, PSEN1, TF, TFAM and TNF and be used to identify subjects with increased risk of developing Alzheimer's disease (Bertram et al, Nat Genet. 2007 January; 39(1): 17-23), as well as variances in the alpha-T catenin (VR22) gene (Bertram et al, J Med Genet. 2007 January; 44(1):e63) and Insulin-degrading enzyme (IDE) and Kim et al, J Biol Chem. 2007; 282:7825-32). As disclosed in the present disclosure, CD33 protein or gene encoding the same is also associated with Alzheimer's disease.

One can also diagnose a subject with increased risk of developing Alzheimer's disease on the basis of a simple eye test, where the presence of cataracts and/or Abeta in the lens identifies a subject with increased risk of developing Alzheimer's Disease. Methods to detect Alzheimer's disease include using a quasi-elastic light scattering device (Goldstein et al., Lancet. 2003; 12; 361:1258-65) from Neuroptix, using Quasi-Elastic Light Scattering (QLS) and Fluorescent Ligand Scanning (FLS) and a Neuroptix™ QEL scanning device, to enable non-invasive quantitative measurements of amyloid aggregates in the eye, to examine and measure deposits in specific areas of the lens as an early diagnostic for Alzheimer's disease. Method to diagnose a subject at risk of developing Alzheimer's disease using such a method of non-invasive eye test are disclosed in U.S. Pat. No. 7,107,092, which is incorporated in its entirety herein by reference.

Individuals presently suffering from Alzheimer's disease can be recognized from characteristic dementia, as well as the presence of risk factors described above. In addition, a number of diagnostic tests are available for identifying individuals who have AD. These include measurement of CSF tau and Ax3b242 levels. Elevated tau and decreased Ax3b242 levels signify the presence of Alzheimer's Disease.

There are two alternative "criteria" which are utilized to clinically diagnose Alzheimer's Disease: the DSM-IIIR criteria and the NINCDS-ADRDA criteria (which is an acronym for National Institute of Neurological and Communicative Disorders and Stroke (NINCDS) and the Alzheimer's Disease and Related Disorders Association (ADRDA); see McKhann et al., Neurology 34:939-944, 1984). Briefly, the criteria for diagnosis of Alzheimer's Disease under DSM-IIIR include (1) dementia, (2) insidious onset with a generally progressive deteriorating course, and (3) exclusion of all other specific causes of dementia by history, physical examination, and laboratory tests. Within the context of the DSM-IIIR criteria, dementia is understood to involve "a multifaceted loss of intellectual abilities, such as memory, judgement, abstract thought, and other higher cortical functions, and changes in personality and behaviour." (DSM-1IR, 1987).

In contrast, the NINCDS-ADRDA criteria sets forth three categories of Alzheimer's Disease, including "probable," "possible," and "definite" Alzheimer's Disease. Clinical diagnosis of "possible" Alzheimer's Disease may be made on the basis of a dementia syndrome, in the absence of other neurologic, psychiatric or systemic disorders sufficient to cause dementia. Criteria for the clinical diagnosis of "probable" Alzheimer's Disease include (a) dementia established by clinical examination and documented by a test such as the Mini-Mental test (Foldstein et al., J. Psych. Res. 12:189-198, 1975); (b) deficits in two or more areas of cognition; (c) progressive worsening of memory and other cognitive functions; (d) no disturbance of consciousness; (e) onset between ages 40 and 90, most often after age 65; and (f) absence of systemic orders or other brain diseases that could account for the dementia. The criteria for definite diagnosis of Alzheimer's Disease include histopathologic evidence obtained from a biopsy, or after autopsy. Since confirmation of definite Alzheimer's Disease requires histological examination from a brain biopsy specimen (which is often difficult to obtain), it is rarely used for early diagnosis of Alzheimer's Disease.

One can also use neuropathologic diagnosis of Alzheimer's Disease, where the numbers of plaques and tangles in the neurocortex (frontal, temporal, and parietal lobes), hippocampus and amygdala are analyzed (Khachaturian, Arch. Neurol. 42:1097-1105; Esiri, "Anatomical Criteria for the Biopsy diagnosis of Alzheimer's Disease," Alzheimer's Disease, Current Research in Early Diagnosis, Becker and Giacobini (eds.), pp. 239-252, 1990).

One can also use quantitative electroencephalographic analysis (EEG) to diagnose Alzheimer's Disease. This method employs Fourier analysis of the beta, alpha, theta, and delta bands (Riekkinen et al., "EEG in the Diagnosis of Early Alzheimer's Disease," Alzheimer's Disease, Current Research in Early Diagnosis, Becker and Giacobini (eds.), pp. 159-167, 1990) for diagnosis of Alzheimer's Disease.

One can also diagnose Alzheimer's Disease by quantifying the degree of neural atrophy, since such atrophy is generally accepted as a consequence of Alzheimer's Disease. Examples of these methods include computed tomographic scanning (CT), and magnetic resonance imaging (MRI) (Leedom and Miller, "CT, MRI, and NMR Spectroscopy in Alzheimer's Disease," Alzheimer's Disease, Current Research in Early Diagnosis, Becker and Giacobini (eds.), pp. 297-313, 1990).

One can also diagnose Alzheimer's Disease by assessing decreased cerebral blood flow or metabolism in the posterior temporoparietal cerebral cortex by measuring decreased blood flow or metabolism by positron emission tomography (PET) (Parks and Becker, "Positron Emission Tomography and Neuropsychological Studies in Dementia," Alzheimer's Disease's, Current Research in Early Diagnosis, Becker and Giacobini (eds.), pp. 315-327, 1990), single photon emission computed tomography (SPECT) (Mena et al., "SPECT Studies in Alzheimer's Type Dementia Patients," Alzheimer's Disease, Current Research in Early Diagnosis, Becker and Giacobini (eds.), pp. 339-355, 1990), and xenon inhalation methods (Jagust et al., Neurology 38:909-912; Prohovnik et al., Neurology 38:931-937; and Waldemar et al., Senile Dementias: II International Symposium, pp. 399407, 1988).

One can also immunologically diagnose Alzheimer's disease (Wolozin, "Immunochemical Approaches to the Diagnosis of Alzheimer's Disease," Alzheimer's Disease, Current Research in Early Diagnosis, Becker and Giacobini (eds.), pp. 217-235, 1990). Wolozin and coworkers (Wolozin et al., Science 232:648-650, 1986) produced a monoclonal antibody "Alz50," that reacts with a 68-kDa protein "A68," which is expressed in the plaques and neuron tangles of patients with Alzheimer's disease. Using the antibody Alz50 and Western blot analysis, A68 was detected in the cerebral spinal fluid (CSF) of some Alzheimer's patients and not in the CSF of normal elderly patients (Wolozin and Davies, Ann. Neurol. 22:521-526, 1987).

One can also diagnose Alzheimer's disease using neurochemical markers of Alzheimer's disease. Neurochemical markers which have been associated with Alzheimer's Disease include reduced levels of acetylcholinesterase (Giacobini and Sugaya, "Markers of Cholinergic Dysfunction in Alzheimer's Disease," Alzheimer's Disease, Current Research in Early Diagnosis, Becker and Giacobini (eds.), pp. 137-156, 1990), reduced somatostatin (Tamminga et al., Neurology 37:161-165, 1987), a negative relation between serotonin and 5-hydroxyindoleacetic acid (Volicer et al., Arch Neurol. 42:127-129, 1985), greater probenecid-induced rise in homovanyllic acid (Gibson et al., Arch. Neurol. 42:489-492, 1985) and reduced neuron-specific enolase (Cutler et al., Arch. Neurol. 43:153-154, 1986).

Other methods to diagnose a patient at risk of or having a neurodegenerative disease or disorder, such as Alzheimer's Disease includes measurement of CD33 activity and/or expression using the methods as disclosed herein, for example using quantitative RT-PCR as described in the examples section.

Embodiments of the various aspects disclosed herein can be described by one or more of the following numbered paragraphs:

1. A method of treating a neuro-inflammation disorder in a subject, the method comprising administering to a subject in need thereof an effective amount of an agent that inhibits or reduces the expression or activity of CD33 protein.
2. The method of paragraph 1, wherein said agent is selected from the group consisting of small or large organic or inorganic molecules, nucleic acids, nucleic acid analogs and derivatives, peptides, peptidomimetics, proteins, antibodies and antigen binding fragments thereof, monosaccharides, disaccharides, trisaccharides, oligosaccharides, polysaccharides, lipids, glycosaminoglycans, an extract made from biological materials, and any combinations thereof
3. The method of paragraph 1 or 2, wherein the agent is a nucleic acid selected from the group consisting of siRNA, shRNA, miRNA, anti-microRNA, antisense RNA or oligonucleotide, aptamer, ribozyme, and any combinations thereof.
4. The method of any of paragraphs 1-3, wherein the agent is an RNAi agent.
5. The method of any of paragraphs 1-4, wherein the agent is a nucleic acid and the method comprises administering a vector encoding/expressing the agent to the subject.
6. The method of paragraph 5, wherein the vector is a viral vector
7. The method of paragraph 6, wherein the viral vector is an adeno-associated virus (AAV) vector.
8. The method of paragraph 1 or 2, wherein the agent is a small molecule selected from the group consisting of sialic acid analogues and derivatives.
9. The method of paragraph 1 or 2, wherein the agent is a monoclonal antibody.
10. The method of paragraph 1, 2 or 9, wherein the agent is a humanized antibody.
11. The method of paragraph 1, 2, 9, or 10, wherein the agent is an anti-CD33 antibody or an antigen binding fragment thereof.
12. The method of any of paragraphs 1-11, wherein the agent crosses or is formulated to cross the blood-brain barrier.
13. A method of treating a neuro-inflammation disorder in a subject, the method comprising administering to a subject in need thereof a nucleic acid encoding a CD33 protein, wherein the CD33 protein lacks sialic acid binding domain.
14. The method of paragraph 13, wherein the CD33 protein comprises an amino acid sequence SEQ ID NO: 8.
15. The method of paragraph 13 or 14, wherein the nucleic acid is a vector.
16. The method of paragraph 15, wherein the vector is a viral vector
17. The method of paragraph 16, wherein the viral vector is an AAV vector.
18. The method of paragraph 13 or 14, wherein the nucleic acid is modified RNA.
19. The method of any of paragraphs 1-18, wherein the neuro-inflammation disorder is a neurodegenerative disease or disorder.
20. The method of paragraph 19, wherein the neurodegenerative disease or disorder is selected from the group consisting of Alzheimer's disease (AD), Parkinson's disease (PD), Huntington's Disease, Amyotrophic Lateral Sclerosis (ALS, also termed Lou Gehrig's disease) and Multiple Sclerosis (MS).
21. The method of paragraph 20, wherein the neurodegenerative disease or disorder is Alzheimer's Disease.
22. The method of any of paragraphs 1-21, wherein the subject is mammalian.
23. The method of any of paragraph 22, wherein the subject is human.
24. The method of any of paragraphs 1-23, wherein the agent decreases beta amyloid accumulation in the brain of the subject.
25. The method of paragraph 24, wherein the beta amyloid is Aβ-42
26. A method of decreasing beta amyloid accumulation in the brain of a subject, the method comprising administering to a subject in need thereof an effective amount of an agent that inhibits or reduces the expression or activity of CD33 protein.
27. The method of paragraph 26, wherein said agent is selected from the group consisting of small or large organic or inorganic molecules, nucleic acids, nucleic acid analogs and derivatives, peptides, peptidomimetics, proteins, antibodies and antigen binding fragments thereof, monosaccharides, disaccharides, trisaccharides, oligosaccharides, polysaccharides, lipids, glycosaminoglycans, an extract made from biological materials, and any combinations thereof
28. The method of paragraph 26 or 27, wherein the agent is a nucleic acid selected from the group consisting of siRNA, shRNA, miRNA, anti-microRNA, antisense RNA, aptamer, ribozyme, and any combinations thereof
29. The method of any of paragraphs 26-28, wherein the agent is an RNAi agent.
30. The method of any of paragraphs 26-29, wherein the agent is a nucleic acid and the method comprises administering a vector encoding/expressing the agent to the subject.
31. The method of paragraph 30, wherein the vector is a viral vector
32. The method of paragraph 31, wherein the viral vector is an adeno-associated virus (AAV) vector.
33. The method of paragraph 26 or 27, wherein the agent is a small molecule selected from the group consisting of sialic acid analogues and derivatives.
34. The method of paragraph 26 or 27, wherein the agent is a monoclonal antibody.
35. The method of paragraph 26, 37 or 34, wherein the agent is a humanized antibody.

36. The method of paragraph 26, 27, 34, or 35, wherein the agent is an anti-CD33 antibody or an antigen binding fragment thereof.
37. The method of any of paragraphs 26-36, wherein the agent crosses the blood-brain barrier.
38. A method of decreasing beta amyloid accumulation in the brain of a subject, the method comprising administering to a subject in need thereof a vector expressing administering to a subject in need thereof a nucleic acid encoding a CD33 protein, wherein the CD33 protein lacks sialic acid binding domain.
39. The method of paragraph 38, wherein the CD33 protein comprises an amino acid sequence SEQ ID NO: 8.
40. The method of paragraph 38 or 39, wherein the nucleic acid is a vector.
41. The method of paragraph 40, wherein the vector is a viral vector
42. The method of paragraph 41, wherein the viral vector is an adenovirus vector.
43. The method of paragraph 38 or 39, wherein the nucleic acid is modified RNA.
44. The method of any of paragraphs 26-43, wherein the subject is in need for treating a neuro-inflammation disorder.
45. The method of paragraph 44, wherein the neuro-inflammation disorder is a neurodegenerative disease or disorder.
46. The method of paragraph 45, wherein the neurodegenerative disease or disorder is selected from the group consisting of Alzheimer's disease (AD), Parkinson's disease (PD), Huntington's Disease, Amyotrophic Lateral Sclerosis (ALS, also termed Lou Gehrig's disease) and Multiple Sclerosis (MS).
47. The method of paragraph 46, wherein the neurodegenerative disease or disorder is Alzheimer's Disease.
48. The method of any of paragraphs 26-47, wherein the subject is mammalian.
49. The method of any of paragraph 48, wherein the subject is human.
50. The method of any of paragraphs 26-49, wherein the beta amyloid is Aβ-42.
51. The use of an agent which inhibits or reduces the expression or activity of CD33 protein for the preparation of a medicament for treatment or prevention of a neuro-inflammatory disorder.
52. The use of a vector which expresses a CD33 protein lacking sialic acid binding domain for the preparation of a medicament for treatment or prevention of a neuro-inflammatory disorder.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "decrease", "reduced", "reduction", "decrease" or "inhibit" used herein in context of CD33 expression and/or activity means that the expression or activity of CD33 protein or variants or homologues thereof is reduced to an extent, and/or for a time, sufficient to produce the desired effect.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

The term "disease" or "disorder" is used interchangeably herein, and refers to any alteration in state of the body or of some of the organs, interrupting or disturbing the performance of the functions and/or causing symptoms such as discomfort, dysfunction, distress, or even death to the person afflicted or those in contact with a person. A disease or disorder can also relate to a distemper, ailing, ailment, malady, disorder, sickness, illness, complaint, inderdisposion or affectation.

As used herein, "gene silencing" or "gene silenced" in reference to an activity of n RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

The term "analog" as used herein refers to a compound that results from substitution, replacement or deletion of various organic groups or hydrogen atoms from a parent compound. An analog is structurally similar to the parent compound, but can differ by even a single element of the same valence and group of the periodic table as the element it replaces.

The term "derivative" as used herein refers to a chemical substance related structurally to another, i.e., an "original" substance, which can be referred to as a "parent" compound. A "derivative" can be made from the structurally-related parent compound in one or more steps. The phrase "closely related derivative" means a derivative whose molecular weight does not exceed the weight of the parent compound by more than 50%. The general physical and chemical properties of a closely related derivative are also similar to the parent compound.

To the extent not already indicated, it will be understood by those of ordinary skill in the art that any one of the various embodiments herein described and illustrated can be further modified to incorporate features shown in any of the other embodiments disclosed herein.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Example 1: Alzheimer's Disease Risk Gene CD33 Inhibits Microglial Uptake of Amyloid Beta The transmembrane protein CD33 is a sialic acid-binding immunoglobulin-like lectin that regulates innate immunity but has no known functions in the brain. It was previously shown that the CD33 gene is a risk factor for Alzheimer's disease (AD). Here, increased expression of CD33 in microglial cells in AD brain was observed. The minor allele of the CD33 single nucleotide polymorphism rs3865444, which confers protection against AD, was associated with reductions in both CD33 expression and insoluble amyloid beta 42 (Aβ42) levels in AD brain. Furthermore, the numbers of CD33-immunoreactive microglia were positively correlated with insoluble Aβ42 levels and plaque burden in AD brain. CD33 inhibited uptake and clearance of Aβ42 in microglial cell cultures. Finally, brain levels of insoluble Aβ42 as well as amyloid plaque burden were markedly reduced in $APP_{Swe}/PS1_{\Delta E9}/CD33^{-/-}$ mice. Therefore, CD33 inactivation mitigates Aβ pathology and CD33 inhibition represents a novel therapy for AD.

Here, CD33 is shown to be expressed in microglial cells in the human brain. CD33 protein levels as well as the number of CD33-positive microglia are increased in AD brains relative to age-matched controls. Conversely, it is shown that the minor allele of the CD33 SNP rs3865444, which protects against AD, leads to reductions in both CD33 microglial expression and levels of insoluble Aβ42 in AD brain. Furthermore, the numbers of CD33-immunoreactive microglia positively correlate with insoluble Aβ42 levels and the amyloid plaque burden in AD cases. Using cultured primary and BV2 microglial cells, CD33 is shown to be both required and sufficient to inhibit the microglial uptake of Aβ42, thus impairing Aβ42 clearance. Finally, $APP_{Swe}/PS1_{\Delta E9}$ transgenic mice in which the CD33 gene was knocked out exhibited a marked reduction of insoluble Aβ42 levels and Aβ plaque burden, indicating that CD33 promotes the Aβ42 pathology in vivo. Collectively, these results suggest that CD33 activity in microglia promotes Aβ42 pathology in AD. They also raise the possibility that the loss of microglial degradative capacity of Aβ in AD could be reversed therapeutically by inhibition of CD33 activity.

Increased CD33 Expression in AD.

To assess the role of CD33 in AD pathology, the expression of CD33 was initially assessed in post-mortem brain samples from 25 AD patients and 15 age-matched non-demented controls (cohort characteristics in Table 1). To investigate the relationship between CD33 mRNA levels and AD, quantitative RT-PCR was performed on total mRNA extracted from frozen cortical samples. This revealed a five-fold increase in CD33 mRNA levels in AD cases relative to controls (FIG. 1A, p<0.01, student's t-test). Normalization of CD33 mRNA levels using GAPDH and β-Actin mRNAs led to similar results (FIG. 1A). Next, it was assessed whether CD33 protein levels are increased in the frontal cortex in AD. Western blotting using a CD33-specific antibody (Hoyer et al., 2008; Rollins-Raval and Roth, 2012) revealed a two-fold increase in CD33 protein levels in AD samples relative to controls (FIGS. 1B and 1C, p<0.01, student's t-test). This significant increase was also observed when normalizing CD33 levels to the levels of the microglial marker Iba1 (FIG. 1C, p<0.05, student's t-test), indicating that this difference is not explained by an increased number of microglia in AD. Using stereology-based quantitative methods, it was previously observed that the total number of Iba1-positive microglia is not significantly different between AD and non-demented subjects (unpublished data). Thus, CD33 mRNA and protein levels are increased in AD brain.

TABLE 1

Characteristics of AD cases and controls used in the study

| Characteristics | Controls (n = 15) | AD (n = 25) |
| --- | --- | --- |
| Age at death (years) | 79.9 ± 11.2 | 79.2 ± 8.3 |
| Disease duration (years) | NA | 10.96 |
| Males/Females | 40%/60% | 28%/72% |
| APOEε4 carriers | 5 (33.33%) | 18 (72%) |
| APOEε4 homozygous carriers | 0 | 8 (32%) |
| Post-mortem interval (hours) | 29 ± 9 | 17 ± 12 |

Figures 7A, 7B, 7C, 7D, 7E, 7F:
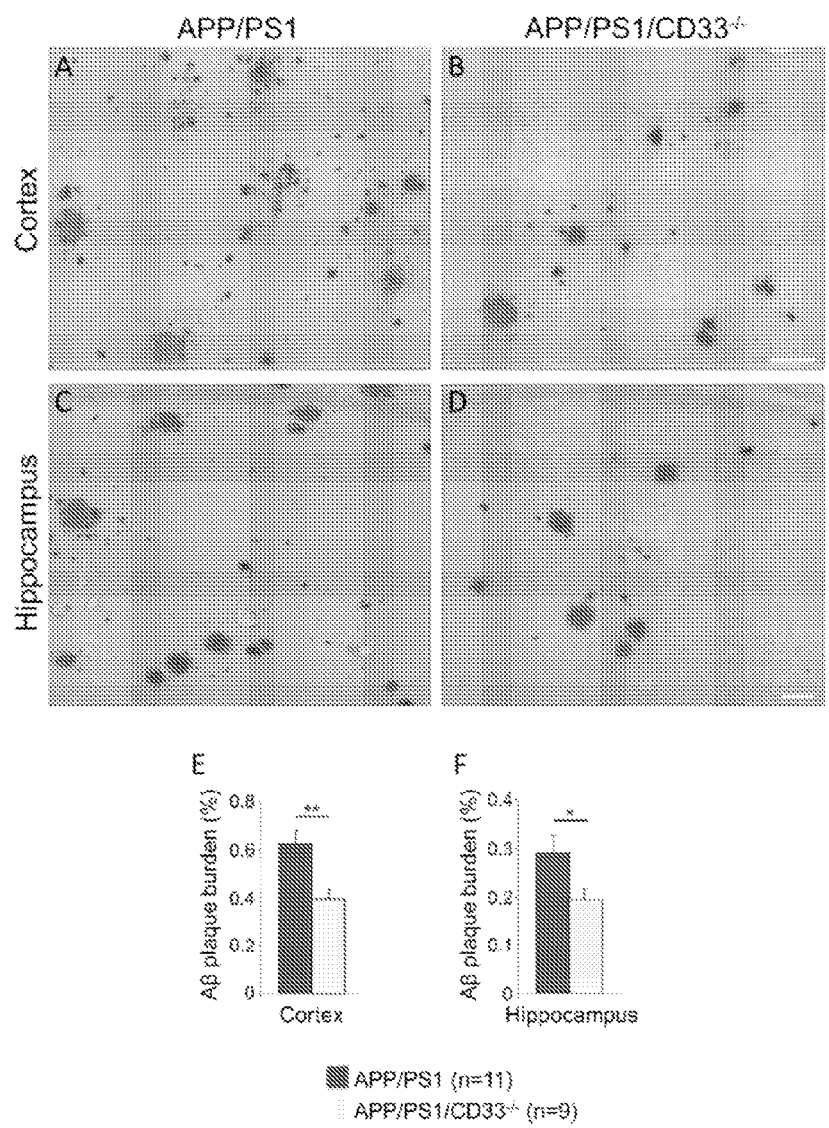
FIGS. 7A-7F shows that CD33 deletion mitigates Aβ plaque pathology in APP/PS1 mice.

The rs3865444 SNP in the CD33 gene was previously reported to confer protection against AD (Hollingworth et al., 2011; Naj et al., 2011). Thus, it was investigated whether CD33 expression differed in carriers of the major (G) allele, relative to the carriers of the minor protective (T) allele. All subjects were genotyped by the Taqman assay using sequence-specific primers, to differentiate between the alleles (Shen et al., 2009). It was found that the minor protective (T) allele is not associated with changes in CD33 mRNA levels (FIG. 1E; p>0.05, general linear regression model). Different sets of primers were used to amplify different regions of the CD33 mRNA, with similar results (FIGS. 7A and 7B). However, remarkably, carriers of the minor (T) allele had significantly reduced CD33 protein levels (normalized to GAPDH or Iba1 protein levels), in both AD and control groups (FIG. 1D; p<0.05, student's t-test and FIG. 7C). It was also found that the protective (T) allele is associated with decreased CD33 protein levels (normalized to GAPDH or Iba1 protein levels) in both control and AD groups (FIG. 1E, p<0.05, general linear regression model). Thus, although the rs3865444 SNP is located on chromosome 19 at the 51,727,962 base pair (bp) position, upstream of the 5' untranslated region of the CD33 gene (51,728,335-51,743,274 bps, forward strand) (Hollingworth et al., 2011; Naj et al., 2011), it does not affect CD33 mRNA stability but somehow influences mRNA translation or protein stability. One possibility is that the rs3865444 SNP is in linkage disequilibrium with another functional variant(s) located in the coding region. The observations of increased CD33 expression in the AD brain and the decreased CD33 protein levels in the carriers of the protective allele of the CD33 SNP rs3865444 strongly suggest a role for CD33 in AD pathogenesis.

Microglial Localization of CD33 and Relationship to AD.

Figures 2A, 2B, 2C, 2D, 2E, 2F, 2G, 2H, 2I, 2J, 2K, 2L, 2M:
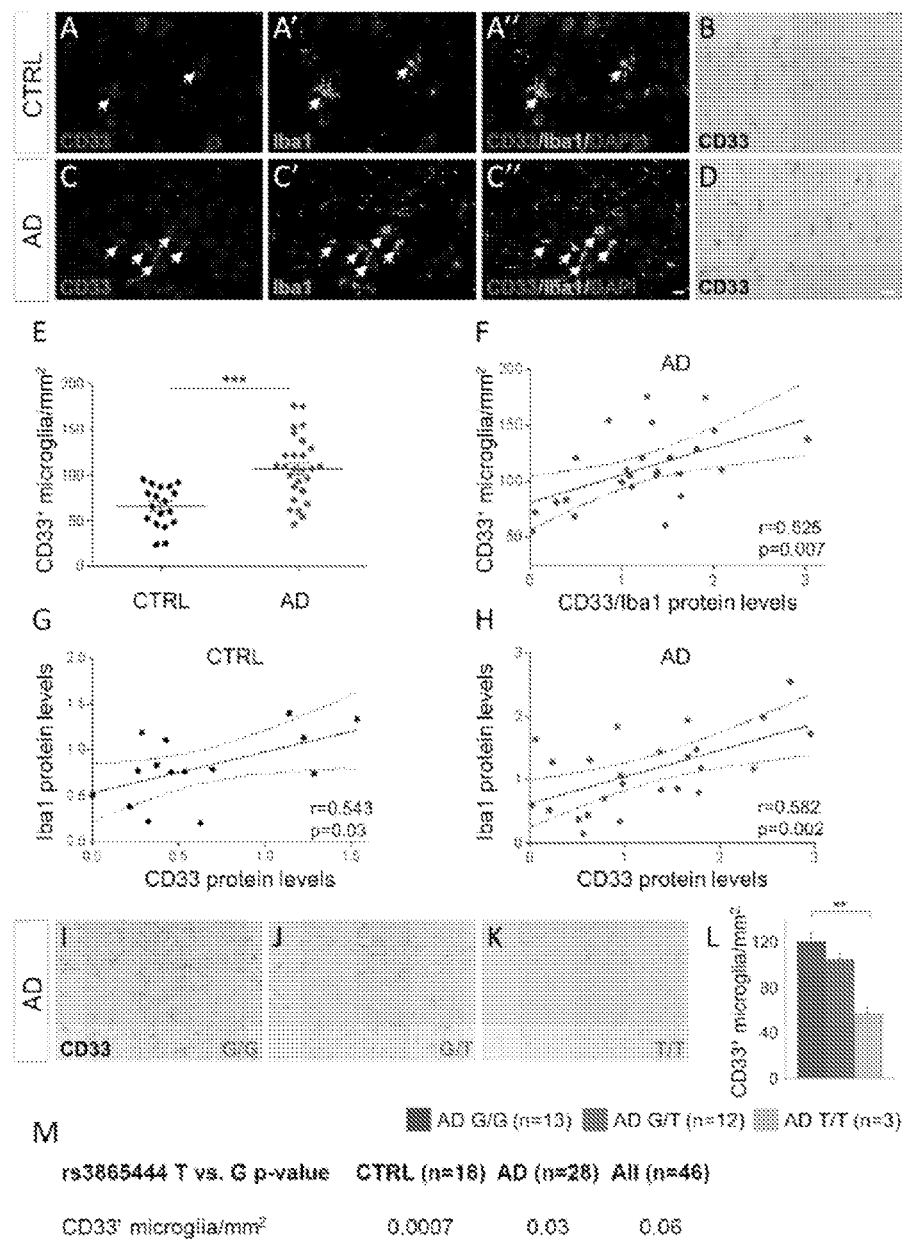
FIGS. 2A-2M show increased number of CD33-immunoreactive microglia in AD.

CD33 has previously been shown to be expressed in cells of the immune and hematopoietic cell systems (Crocker et al., 2007). Microglial cells are responsible for the immune surveillance of the brain and regulate critical processes relevant to AD pathology, including the uptake and clearance of Aβ (Aguzzi et al., 2013; Prinz et al., 2011). Thus, it was investigated whether CD33 is expressed in microglial cells. Immunolabeling of control and AD frontal cortex sections, using a CD33-specific antibody (Hoyer et al., 2008; Rollins-Raval and Roth, 2012) and the microglial marker Iba1 revealed a good co-localization between the two proteins (FIGS. 2A and 2C). CD33 was also expressed in neurons (FIGS. 8D and 8E), but not in astrocytes, oligodendrocytes or endothelial cells (FIGS. 8G-8I).

Figures 8A, 8B, 8C:
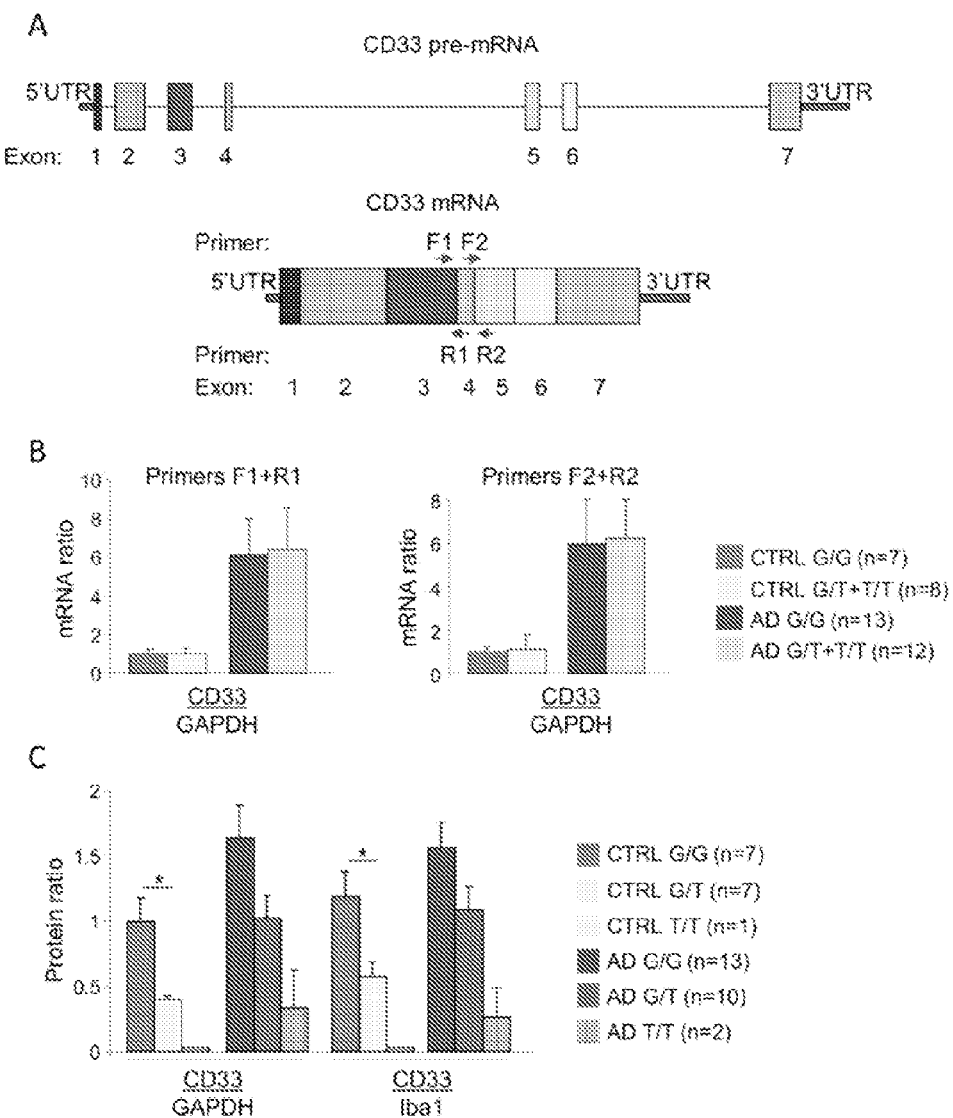
FIGS. 8A-8C show decreased levels of CD33 protein in carriers of the rs3865444 minor (T) allele.

Next, it was investigated whether the number of CD33-immunoreactive cells differed between AD and control brains. Sections immunolabeled for CD33 and stained with diaminobenzidine (DAB) were subjected to stereology-based quantifications, using previously described protocols (Serrano-Pozo et al., 2011). The total numbers of CD33-positive cells increased by 48.9% in the AD frontal cortex relative to age-matched controls (FIG. 8A, n=28 AD cases and 18 controls, p<0.001, student's t-test). The CD33-positive microglia was identified using morphological criteria (FIGS. 2B and 2D). Stereology-based quantification of the numbers of CD33-immunoreactive microglia revealed a marked increase in the AD frontal cortex relative to age-matched controls (FIG. 2E, n=28 AD cases and 18 controls, p<0.001, student's t-test). It was also investigated whether the number of CD33-positive neurons differed between AD and control subjects. No significant difference was found between the numbers of CD33-positive neurons in AD and controls (FIGS. 8B and 8C). The levels of CD33 protein normalized to Iba1 protein levels positively correlated with the numbers of CD33-immunoreactive microglial cells, as expected (FIG. 2F, p=0.007, Pearson's correlation test). To validate these findings, the relationship between the levels of CD33 protein and those of the microglial marker Iba1 was assessed, using western blotting and frontal cortex protein extracts. A positive correlation between CD33 and Iba1 levels was found, both in control (FIG. 2G, p=0.03, Pearson's correlation test) and AD cases (FIG. 2H, p=0.002, Pearson's correlation test).

It was investigated if the minor (T) allele of the CD33 SNP rs3865444 is associated with changes in the number of CD33-positive microglia. Carriers of the protective (T) allele were found to have lower numbers of CD33-positive microglial cells (FIGS. 2I-2K); this effect was dose-dependent, i.e. carriers of two (T) alleles exhibited a dramatic reduction of CD33-positive microglia numbers relative to carriers of one (T) allele or carriers of the major (G) allele (FIG. 2L, p<0.01 T/T versus G/G carriers, one-way Kruskal-Wallis ANOVA, Dunn's test). It was found that the minor protective (T) allele is associated with decreased CD33-immunoreactive microglia numbers in both the control and AD groups (FIG. 2M, p<0.001 and p<0.05 respectively, general linear regression model). Therefore, the numbers of CD33-positive microglia are increased in AD cases and are reduced in carriers of two protective (T) alleles, suggesting that CD33 activity in microglia might impact the etiology and/or pathogenesis of AD.

CD33 Microglial Expression Correlates with Amyloid Beta Pathology in AD.

Increased production and deposition of aggregation-prone Aβ species are hallmarks of AD pathology (Selkoe, 2012; Tanzi and Bertram, 2005). It was investigated whether Aβ levels were different in carriers of the major (G) allele of the CD33 SNP rs3865444 in comparison to the carriers of the protective (T) allele. Tris-buffered saline (TBS)-soluble and formic acid (FA)-soluble fractions were generated from the frontal cortex tissue of controls and AD cases (Wang et al., 2011) and these fractions were used for Aβ ELISA experiments. Remarkably, the carriers of the minor (T) allele were found to have significantly reduced FA-soluble Aβ42 levels but not FA-soluble Aβ40 in comparison to the carriers of the major (G) allele in AD (FIG. 3A, p<0.01, student's t-test). The minor protective (T) allele was also observed to be associated with decreased levels of both TBS-soluble Aβ40 and FA-soluble Aβ42 in AD cases (FIG. 3B, p<0.05 and p<0.01 respectively, general linear regression model).

Microglial cells regulate Aβ levels in the brain by a process of uptake and degradation, which plays a key role in AD pathogenesis (Aguzzi et al., 2013; Prinz et al., 2011). To explore the relationship between CD33 microglial expression and amyloid pathology, the AD frontal cortex was labeled with Thioflavin S (to detect amyloid plaques) and antibodies directed against CD33 and the microglial marker Iba1. This revealed a broad distribution of CD33-positive microglia throughout the AD cortex together with an enrichment of CD33-positive microglia around amyloid plaques (FIGS. 9A-9I). It was then explored the possibility that increased CD33 microglial expression in the aging brain promotes Aβ pathology by preventing the efficient Aβ clearance. The numbers of CD33-immunoreactive microglia were found to be positively correlated with the levels of FA-soluble Aβ42 in AD brain (FIG. 3C, p=0.02, Spearman's correlation test). It was investigated whether Aβ plaque burden in AD cases correlates with the numbers of CD33-positive microglia. The Aβ plaque burden in the frontal cortex of AD subjects was estimated as the proportion of area of full-width cortex occupied by Aβ-immunoreactive deposits in sections immunostained with an antibody directed against Aβ (residues 3-7, 10D5) (Serrano-Pozo et al., 2011). Remarkably, a positive correlation between amyloid plaque burden and numbers of CD33-immunoreactive microglial cells in AD cases was found (FIG. 3D, p=0.017, Spearman's correlation test). These results suggest that increased microglial expression of CD33 prevents Aβ clearance and strongly implicate microglial CD33 function in Aβ pathology in AD brain.

CD33 Inactivation Promotes the Uptake of Amyloid Beta by Microglia.

Figures 10A, 10B, 10C:
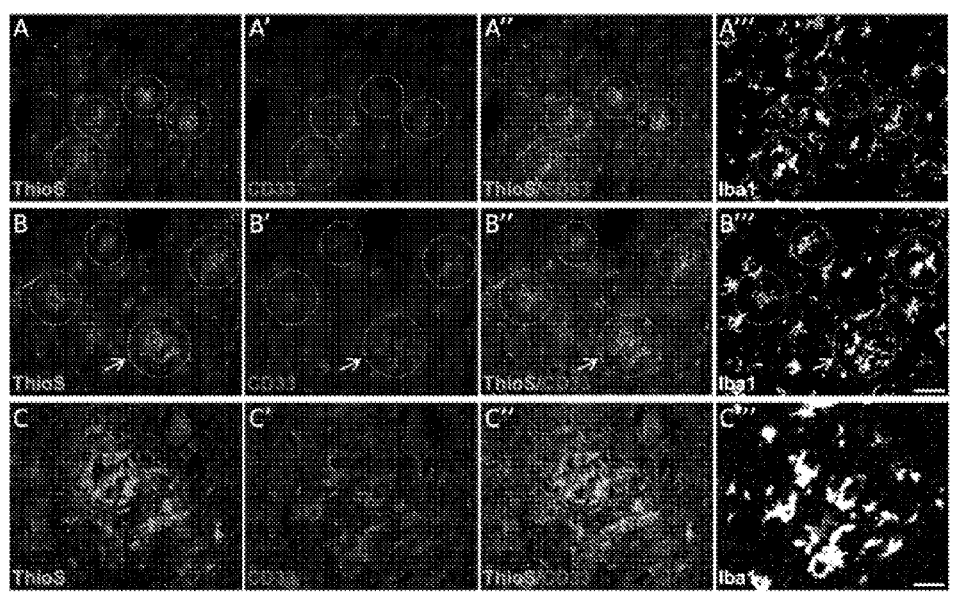
FIGS. 10A-10C''' show localization of CD33 and relationship to amyloid plaques.

The genetic, biochemical, and histopathological data strongly suggest that the activity of CD33 in microglia impacts the accumulation of Aβ in the brain. To test for a causal relationship between CD33 activity and Aβ pathology in AD, an in vitro assay of Aβ uptake and clearance was employed, using primary microglia isolated from mice with a constitutive inactivation of the CD33 gene and littermate wild-type (WT) controls. CD33 inactivation in mice does not lead to obvious developmental, histological and behavioral abnormalities, and CD33$^{-/-}$ mice breed normally (Brinkman-Van der Linden et al., 2003). A mixed glial (microglia/astrocyte) primary culture was established using the forebrain of WT and CD33$^{-/-}$ postnatal day 1 (P1) pups as source of cells, and subsequently enriched for microglial cells (Choi et al., 2008; Gorlovoy et al., 2009); the microglial cultures contained more than 93% microglial (Iba1-positive) cells. No differences in proliferation, growth and morphological parameters between WT and CD33$^{-/-}$ microglia (data not shown). These cells were stained with a CD33 antibody (FIGS. 10A-10C).

Figures 4A, 4B, 4C, 4D, 4E:
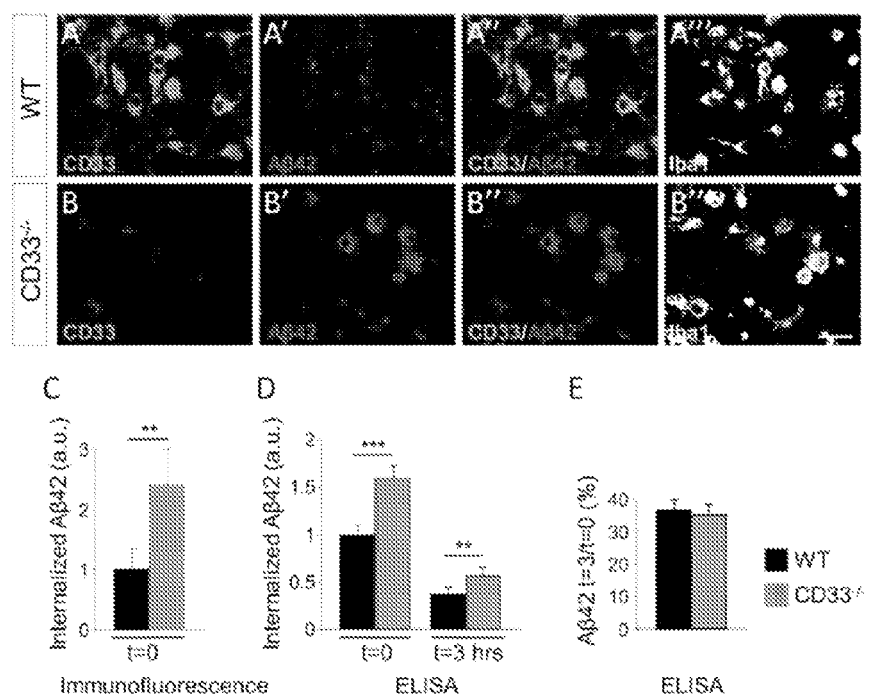
FIGS. 4A-4E show that CD33 inactivation leads to increased microglial uptake of Aβ42.

Microglia derived from CD33$^{-/-}$ mice were not immunoreactive to the CD33 antibody, as expected (FIGS. 4A and 4B). The enriched microglial cultures were incubated with Aβ42 for 3 hours, which allows efficient Aβ42 uptake. Subsequently, the Aβ42 was washed out and the cells were incubated for an additional 3 hours, to allow for Aβ42 degradation (Jiang et al., 2008; Mandrekar et al., 2009). To visualize the process of Aβ42 uptake, fluorescently labeled Aβ42 was used (Lee et al., 2012). Visually, there was a strong increase in Aβ42 levels in CD33$^{-/-}$ microglia relative to WT microglia (FIGS. 4A' and 4B'). Quantification of the fluorescent Aβ42 signal revealed a significant increase in Aβ42 uptake in CD33$^{-/-}$ relative to WT cells (FIG. 4C, p<0.01, student's t-test). The process of Aβ42 degradation cannot be assessed by imaging with fluorescently labeled Aβ42, because microglial cells degrade Aβ42 but they do not completely degrade the attached fluorophore (Mandrekar et al., 2009). To validate the Aβ42 uptake findings, and investigate whether CD33 inactivation impacts Aβ42 degradation as well, Aβ42 levels were measured by ELISA on extracts prepared from cultures incubated with unlabeled Aβ42 (FIGS. 4D and 4E). It was found that CD33-/- microglia contained increased Aβ42 levels after 3 hours of incubation (FIG. 4D), confirming the imaging findings. However, after three hours of Aβ42 washout, similar rates of Aβ42 degradation in both CD33$^{-/-}$ and WT microglia were found (FIG. 4E). Together, these results suggest that CD33 directly impacts Aβ42 uptake, but not Aβ42 degradation, in microglial cells.

Increased CD33 Levels Inhibit Microglial Uptake of Amyloid Beta.

Figures 5A, 5B, 5C, 5D, 5E, 5F, 5G:
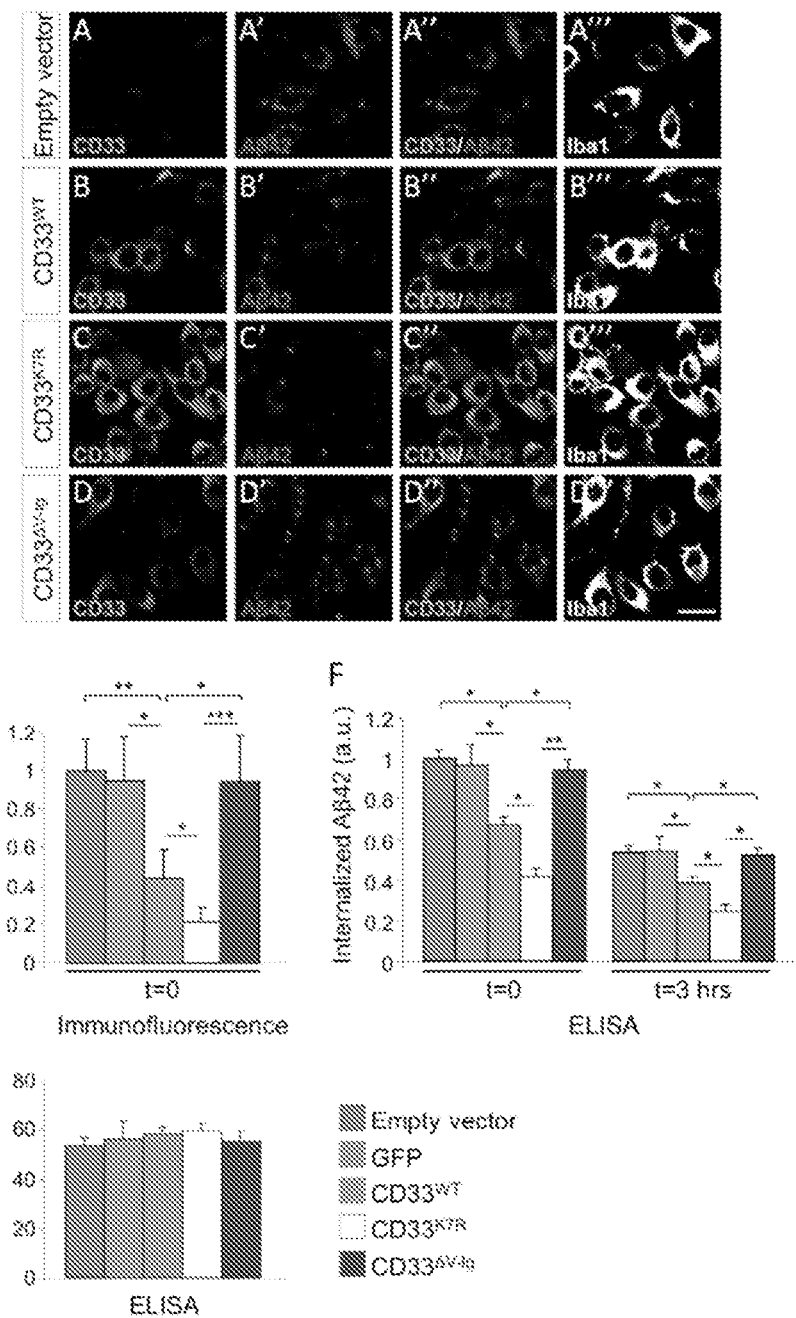
FIGS. 5A-5G shows that CD33 inhibits microglial uptake of Aβ42.

It was next assessed whether increasing CD33 levels impairs Aβ42 uptake by microglial cells. For this purpose, the BV2 microglial cell line was employed, which was previously found to efficiently take-up and degrade exogenously added Aβ42 (Jiang et al., 2008; Mandrekar et al., 2009). Cells transfected with a WT-CD33 construct displayed a decreased uptake of fluorescently-labeled Aβ42 relative to cells transfected with an empty construct (FIGS. 5A' and 5B' and 5E, p<0.01, one-way ANOVA, Tukey's test). These results were confirmed by ELISA quantifications (FIG. 5F, p<0.05, one-way ANOVA, Tukey's test). Furthermore, ELISA also revealed that Aβ42 was degraded at similar rates by cells transfected with WT-CD33 or an empty vector (FIG. 5G). Similar differences were observed when a construct expressing GFP was used as a control (FIGS. 5E-5G). Thus, increasing CD33 levels is sufficient to inhibit Aβ42 uptake, but not degradation, by microglial cells.

Cells were next transfected with a mutant version of CD33 in which seven lysine residues from the intracellular C-terminal domain were mutated to arginine (CD33$^{K7R}$). This prevents CD33 ubiquitylation and subsequent internalization from the plasma membrane (Walter et al., 2008). It was confirmed that the CD33$^{K7R}$ protein displayed enhanced cell surface expression of CD33 (FIG. 5C) in comparison to the CD33$^{WT}$ protein (FIG. 5B). Expression of the CD33$^{K7R}$ protein led to a further inhibition of Aβ42 uptake (FIGS. 5C' and 5E, p<0.05 CD33$^{K7R}$ versus CD33, one-way ANOVA, Tukey's test and FIG. 5F), but did not impair subsequent Aβ42 degradation (FIG. 5G), further indicating that CD33 inhibits Aβ42 uptake by microglial cells.

CD33 and the related Siglecs perform their biological functions by interacting with sialic acids, which are attached to the outer membrane of cells, and can mediate cis- or trans-cellular interactions (Paulson et al., 2012). To determine whether the interaction between CD33 and sialic acids is involved in Aβ42 uptake, a CD33 mutant construct was employed in which the sialic acid-binding V-type Immunoglobulin-like (V-Ig) domain was deleted (Perez-Oliva et al., 2011). The mutant CD33ΔV-Ig protein is present at the plasma membrane in BV2 cells, and is expressed at levels similar to CD33WT (FIGS. 5B and 5D and (Perez-Oliva et al., 2011)). Remarkably, inhibition of Aβ42 uptake by CD33 was completely abolished in cells expressing the CD33ΔV-Ig protein; Aβ42 levels were similar to those in cells expressing empty vector or GFP (FIGS. 5E and 5F), indicating that sialic acid binding is required for CD33 to mediate Aβ42 uptake. Collectively, these experiments indicate that CD33 modulates microglial uptake of Aβ42. Specifically, lower levels of cell surface CD33 enhance Aβ42 internalization, while higher levels impair this process. Moreover, interaction of CD33 with sialic acids is necessary to mediate these effects.

CD33 Activity Promotes Amyloid Beta Pathology in Vivo.

Figures 6A, 6B, 6C, 6D, 6E, 6F:
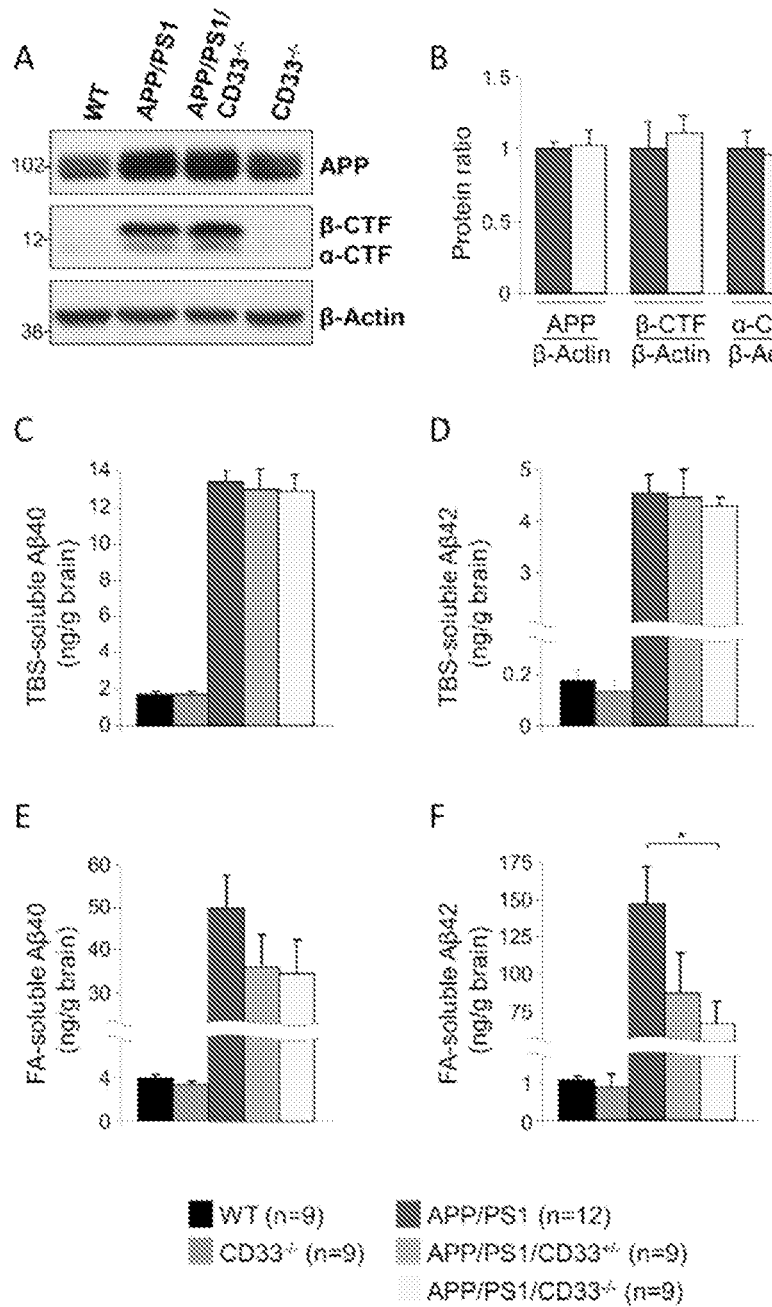
FIGS. 6A-6F shows that CD33 deletion decreases formic acid-soluble Aβ42 levels in APP/PS1 mice.

The above in vitro experiments, together with the genetic, biochemical and histopathological observations, strongly implicate CD33 activity in Aβ pathology in AD. To provide direct in vivo evidence that CD33 activity potentiates Aβ pathology in vivo, a model of AD, the APP$_{Swe}$/PS1$_{ΔE9}$ mouse (subsequently referred to as APP/PS1) was used in which CD33 function was inactivated. APP/PS1 mice exhibit elevated Aβ (including Aβ42) production and develop amyloid plaques (Jankowsky et al., 2004). APP/PS1 mice lacking CD33 (APP/PS1/CD33$^{-/-}$) were born at Mendelian ratios and exhibited no gross anatomical defects (data not shown). The cortex was isolated from four-month-old APP/PS1 and APP/PS1/CD33–/– mice and their littermate controls and detergent-soluble fractions were derived that were used for subsequent western blotting as well as TBS-soluble and FA-soluble fractions (Wang et al., 2011) that were used for Aβ ELISA experiments. Using western blotting it was found, as expected, increased and similar levels of full-length APP and APP C-terminal fragments (APP-CTF) in both APP/PS1 and APP/PS1/CD33–/– mice as compared to controls (FIGS. 6A and 6B). BACE1 levels also did not differ across genotypes (data not shown).

Figures 11B, 11C:
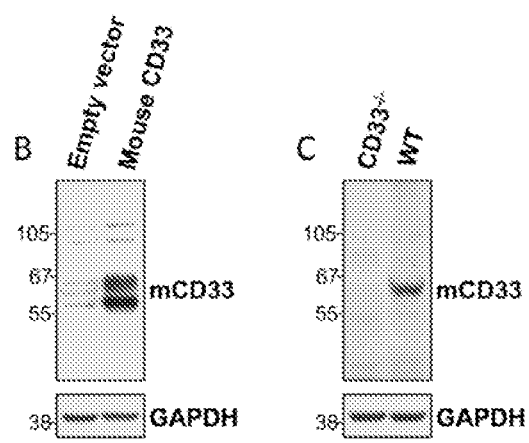
Figures 12A, 12U:
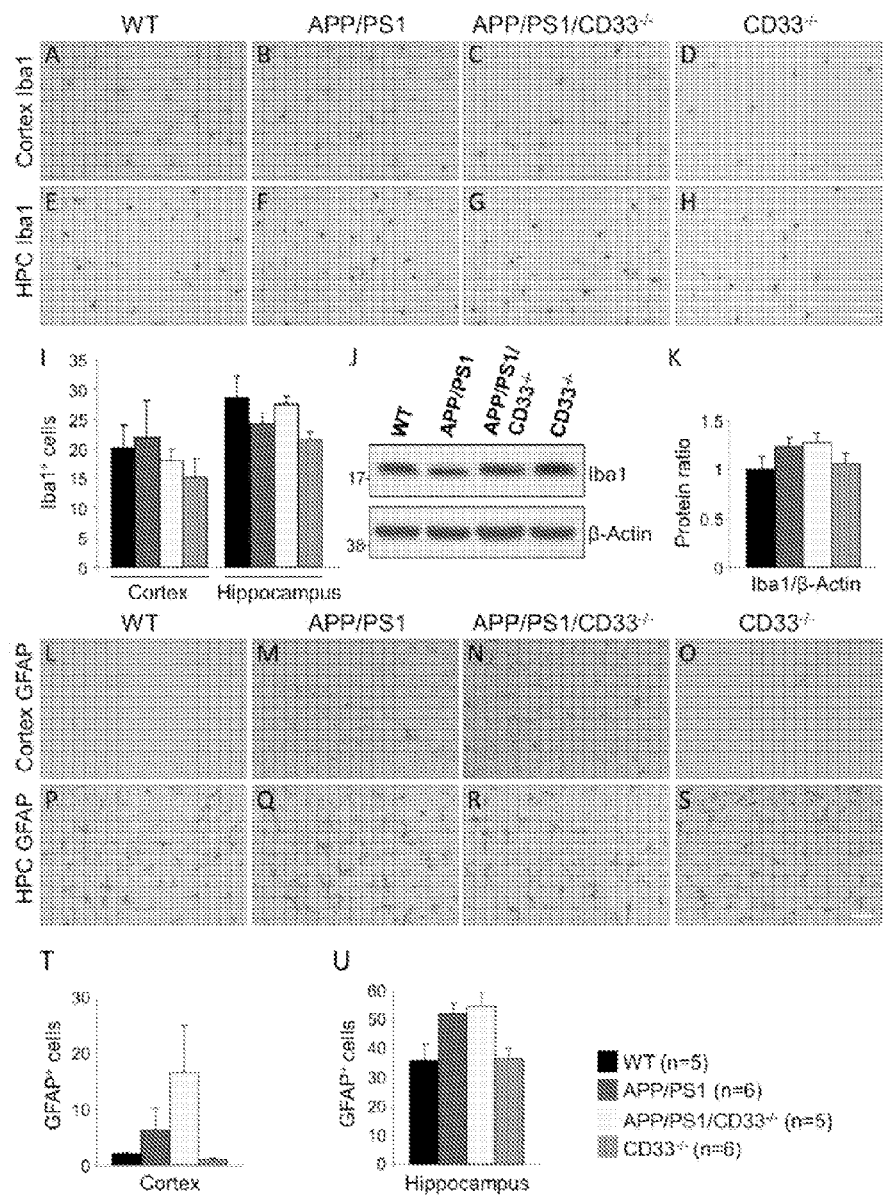
FIGS. 12A-12U show that APP/PS1/CD33$^{-/-}$ mice do not display enhanced microglial recruitment or accelerated astrogliosis in comparison to APP/PS1 mice. Shown are representative microphotographs of cortical (FIGS. 12A-12D, FIGS. 12L-12O) and hippocampal (FIGS. 12E-12H, FIGS. 12P-12S) coronal sections stained for Iba1 (FIGS. 12A-12H) and GFAP (FIGS. 12L-12S).

Next it was investigated whether knockout of CD33 affects Aβ levels in the APP/PS1 mice. As expected, it was found that Aβ40 and Aβ42 levels (measured by ELISA) in the TBS-soluble fraction were markedly increased in APP/PS1 mice relative to WT and CD33$^{-/-}$ mice (FIGS. 6C and 6D). Furthermore, the levels of Aβ40 and Aβ42 in the TBS-soluble fraction were similar in the APP/PS1, APP/PS1/CD33$^{+/-}$ and APP/PS1/CD33$^{-/-}$ mice (FIGS. 6C and 6D). Remarkably, however, the levels of Aβ42, were significantly decreased in the FA-soluble fraction of APP/PS1/CD33$^{-/-}$ mice relative to APP/PS1 mice (FIG. 6F, p<0.05 APP/PS1/CD33–/– versus APP/PS1 mice, one-way Kruskal-Wallis ANOVA, Dunn's test). This effect was not due to increased numbers of microglial cells or astrocytes in APP/PS1/CD33$^{-/-}$ mice (FIGS. 11A-11C) nor alterations in the levels of neither inducible nitric oxide synthase, nor microglia-derived cytokines, e.g. IL-1β and TNFα (data not shown). These data suggest that CD33-deficient microglia possess increased Aβ42 uptake/clearance capacity in vivo and that the CD33-mediated effect on microglial clearance of Aβ42 is cell-autonomous.

Finally, it was investigated whether CD33 deletion impacts the process of Aβ deposition in the APP/PS1 brain. Aβ deposition is obvious by 6 months in APP/PS1 mice when both compact and diffuse Aβ-containing plaques can be observed in the forebrain (Jankowsky et al., 2004). Coronal sections from 6-7 month-old control, CD33$^{-/-}$, APP/PS1 and APP/PS1/CD33$^{-/-}$ mice were stained with an antibody directed against Aβ (residues 1-5, 3D6) that recognizes both compact and diffuse Aβ plaques (Reilly et al., 2003). The 3D6 antibody did not label any plaques in control and CD33$^{-/-}$ brains (data not shown). Analysis of the APP/PS1 brains revealed numerous Aβ plaques, both in the cortex and the hippocampus (FIGS. 7A and 7C). Sections spanning the cortex or the hippocampus were subjected to quantification of amyloid plaque burden. Remarkably, the Aβ plaque burden was robustly decreased in the APP/PS1/CD33$^{-/-}$ brains relative to the APP/PS1 brains (FIGS. 7B and 7D). The quantification revealed a 37.2% and 33.5% reduction of Aβ plaque burden in the APP/PS1/CD33$^{-/-}$ cortex and hippocampus, respectively (FIGS. 7E and 7F; n=9-11 animals/group, p<0.01 and p<0.05, APP/PS1/CD33$^{-/-}$ versus APP/PS1 cortex and hippocampus, respectively, student's t-test). Therefore, CD33 promotes Aβ deposition and plaque formation in vivo.

Discussion

Despite great strides towards the development of an effective therapy, no treatment is currently able to prevent, delay or stop AD progression. This is due in part to our incomplete understanding of AD pathogenesis. While important advances have been made towards a better understanding of FAD, comparatively little is known about LOAD. Great advances in DNA sequencing technologies coupled with the investigation of large human cohorts have provided an unprecedented analytic power and have led to the identification of multiple risk factors for LOAD, thus opening new research avenues that might advance our understanding of this devastating disease.

The CD33 gene has been found to be associated with risk for LOAD (Bertram et al., 2008; Hollingworth et al., 2011; Naj et al., 2011). CD33 is a member of the Siglec family of lectins that bind sialic acid residues leading to cis (same CD33-expressing cell) or trans (adjacent cells) interactions that regulate several aspects of innate immunity (Crocker et al., 2007; Paulson et al., 2012). To date, the role of CD33 in the brain has remained unknown. To bridge this gap, and to understand how CD33 misregulation contributes to LOAD pathogenesis, a comprehensive analysis of CD33 expression and mechanism of action was performed, using a combination of human and mouse genetics, biochemistry, neuropathology and in vitro modeling. Based on these findings, without wishing to be bound by theory, increased CD33 activity in microglial cells inhibits Aβ clearance in LOAD; thus, CD33 inhibition represents a novel means for preventing and treating AD.

CD33 Expression is Increased in AD.

It was found that the levels of CD33 protein are increased in AD. This increase was paralleled by an increase in the number of CD33-immunoreactive microglia. Moreover, the ratio CD33/Iba1 is also increased in AD, suggesting that individual microglia display increased CD33 levels in AD. Thus, AD cases are characterized by both an increase in the number of CD33-immunoreactive microglia and an increase in CD33 levels in these CD33-positive cells. Moreover, the fact that the levels of CD33 mRNA were also strongly increased in AD suggests a potential upregulation of CD33 transcription in microglial cells; alternatively, the CD33 mRNA might exhibit increased stability in microglia in the AD brain. It can be important to determine whether CD33 is part of a broader transcriptional program that operates in microglial cells in the aging brain and to identify the upstream activators of such a program.

To further explore the relationship between CD33 expression and AD, CD33 expression was assessed in carriers of the minor (T) allele of the CD33 SNP rs3865444, which protects against AD. It was found that the minor (T) allele is associated with reduced CD33 protein levels, both in the AD and control subjects (FIG. 1E). Interestingly, the levels of CD33 mRNA were not reduced in the carriers of this allele. The rs3865444 SNP is located upstream of the 5' untranslated region of the CD33 gene (Hollingworth et al., 2011; Naj et al., 2011). One possibility is that the rs3865444 SNP is in linkage disequilibrium with a functional variant(s) located in the coding region. This, in turn, could influence mRNA translation without affecting mRNA stability. Recently, increased CD33 mRNA levels were independently shown to be associated with AD; CD33 mRNA levels correlated with Iba1 mRNA levels and CD33 mRNA expression normalized to Iba1 expression correlated with disease status and Clinical Dementia Rating scores (Karch et al., 2012). The increased CD33 (mRNA and protein) levels in the AD brain and decreased CD33 protein levels in the carriers of the protective allele suggest that increased CD33 expression plays a direct role in the etiology and/or pathogenesis of AD.

CD33 is a Novel Modifier of Amyloid Beta Pathology.

Several genes associated with LOAD have been shown to be critically involved in the control of Aβ homeostasis. ApoE binds Aβ and influences its oligomerization (Hashimoto et al., 2012). It was recently found that lipidated apoE, in particular its pathogenic variant apoE4, increases the oligomerization of Aβ; as a consequence, APOE 84/84 AD brains displayed higher levels of Aβ oligomers relative to APOE 83/83 brains (Hashimoto et al., 2012). The LOAD-associated gene Clusterin (CLU) encodes an extracellular chaperone apolipoprotein J (apoJ) that interacts with Aβ prefibrillar structures and inhibits Aβ aggregation (Yerbury et al., 2007). ApoJ also facilitates the transport of plasma-derived Aβ across the blood brain barrier (BBB) and Aβ42 clearance at the BBB in mice (Bell et al., 2007). Interestingly, apoJ cooperates with apoE to suppress Aβ levels and deposition in vivo (DeMattos et al., 2004).

Besides the control of Aβ self-assembly, LOAD-associated genes are able to control the trafficking of APP and thus influence the formation of Aβ. A genetic screen in yeast revealed that several LOAD genes (including PICALM and BIN1) were modifiers of Aβ toxicity, and suggested that these genes regulate the endocytic trafficking of APP (Treusch et al., 2011). Moreover, PICALM promotes APP internalization, endocytic trafficking and Aβ generation in neurons in vitro (Xiao et al., 2012). The ABCA7 LOAD risk gene also regulates APP trafficking, by stimulating cholesterol efflux, which decreases the levels of APP at the plasma membrane and Aβ generation (Chan et al., 2008). Therefore, targeting the intracellular trafficking of APP in neurons might represent a novel therapeutic approach in AD.

CD33 was identified as a novel modifier of Aβ pathology in vivo. It was observed that an association existed between the protective minor (T) allele of the CD33 SNP rs3865444 and decreased FA-soluble Aβ42 levels in AD as well as a positive correlation between CD33 microglial expression and FA-soluble Aβ42 levels and amyloid plaque burden in the AD cortex (FIG. 3). Moreover, CD33 levels directly impact microglial uptake of Aβ42 (FIGS. 4 and 5) and modulate the accumulation of FA-soluble Aβ42 and Aβ plaque burden in APP/PS1 transgenic mice (FIGS. 6 and 7). Based on these observations, without wishing to be bound by theory, the increased activity of CD33 in microglial cells contributes to the etiology and/or pathogenesis of AD by preventing Aβ uptake and thus potentiating its toxicity.

Taken together, the multiple lines of evidence implicating multiple LOAD risk genes in the control of Aβ production, clearance and deposition provide additional support for the amyloid hypothesis of AD by demonstrating that failure of multiple systems that ensure Aβ homeostasis is associated with an increased risk for developing AD. These findings also indicate immense therapeutic opportunities, since the identification of drug targets that are critically involved in control of Aβ pathogenicity by the novel LOAD risk genes might provide novel strategies targeting the earliest stages of cognitive decline, well before the occurrence of overt neurodegeneration.

CD33 Inhibits the Microglial Uptake of Amyloid Beta.

Based on the finding that CD33 microglial expression is elevated in AD but decreased in carriers of the protective minor (T) allele of the CD33 SNP rs3865444, it was hypothesized that the activity of CD33 in microglia promotes AD pathogenesis. To test this hypothesis and to unravel the molecular underpinnings of CD33 action in microglial cells, it was investigated whether CD33 is involved in the process of Aβ clearance by microglia. Using an assay of microglial uptake and clearance optimized for Aβ42 (Jiang et al., 2008), it was found that mouse primary microglial cells lacking CD33 expression exhibit an increased uptake of Aβ42 relative to WT cells (FIGS. 4A-4D). Interestingly, CD33-deficient and WT cells degraded Aβ42 at a similar rate (FIG. 4E). In CD33-deficient cells, however, Aβ42 clearance was accelerated, due to the increased overall uptake. To further explore the involvement of CD33 in Aβ42 uptake by microglial cells, a well-characterized microglial cell line (BV2) was employed which effectively internalizes and degrades added Aβ42 (Mandrekar et al., 2009). It was found that microglia overexpressing WT CD33 were markedly impaired in their capacity to internalize Aβ42, but degraded the internalized Aβ42 at a similar rate to cells transfected with an empty plasmid or a plasmid encoding GFP (FIGS. 5E-5G). This finding was also validated by the transfection with an ubiquitylation-defective CD33 mutant (CD33$^{K7R}$), which exhibits enhanced cell surface expression of CD33 (FIG. 5C and (Walter et al., 2008)) and further exacerbates the inhibition of Aβ42 uptake (FIGS. 5E and 5F). Thus, CD33 directly modulates uptake, but not degradation, of Aβ42 by microglial cells.

CD33 and the related Siglecs perform their biological functions by interacting with sialic acids, which are attached to the outer membrane of cells, and can mediate cis- or trans-cellular interactions (Crocker et al., 2007). To explore the requirement of sialic acid binding in the process of CD33-mediated microglial uptake of Aβ42, microglial BV2 cells were transfected with a CD33 mutant in which the sialic acid-binding V-type immunoglobulin-like domain was removed. The mutant CD33$^{\Delta V-Ig}$ protein is present at the plasma membrane in BV2 cells, and is expressed at levels similar to CD33$^{WT}$ (FIGS. 5B and 5D and (Perez-Oliva et al., 2011)). Cells expressing the CD33$^{\Delta V-Ig}$ protein were no longer impaired in their capacity to uptake Aβ42, indicating that sialic acid binding is necessary for the ability of CD33 to inhibit Aβ42 uptake. Collectively, these experiments indicate that CD33 directly modulates microglial uptake of Aβ42, via interaction with sialic acids.

Microglial cells have been suggested to play critical roles as mediators of Aβ clearance in the brain. A previous study (Grathwohl et al., 2009) challenged this view by showing that ablation of microglial cells (using drug-induced microglial toxicity) did not alleviate Aβ pathology in two AD mouse models, within a 4 week time-window following the ablation. These results await confirmation in a setting of prolonged microglial ablation (several months to years). It also remains to be determined whether an acute removal of microglial cells has a specific effect on the dynamics of monomeric and oligomeric as opposed to fibrillar Aβ.

Mounting evidence implicates genes associated with risk for LOAD in the process of microglial clearance of Aβ42. For example, apoE promotes the clearance of Aβ in the brain, partly through its capacity to enhance Aβ uptake and degradation by microglia (Jiang et al., 2008; Lee et al., 2012). Interestingly, another LOAD risk gene, ApoJ/Clusterin (CLU) cooperates with APOE to suppress Aβ levels and deposition in PDAPP transgenic mice (DeMattos et al., 2004). A rare variant of the TREM2 gene has been recently shown to confer increased risk for LOAD (Guerreiro et al., 2013; Jonsson et al., 2013). TREM2 is an innate immune receptor, similar to CD33, and is expressed in a subset of myeloid cells including microglia (Klesney-Tait et al., 2006). Remarkably, TREM2 is upregulated in amyloid plaque-associated microglia in aging APP23 transgenic mice (Frank et al., 2008) and in CRND8 transgenic mice (expressing mutant KM670/671NL and V717F APP) (Guerreiro et al., 2013) and promotes the phagocytic clearance of amyloid proteins (Melchior et al., 2010). Interestingly, TREM2 interacts with its ligand TREM2-L, expressed by apoptotic neurons, and mediates removal of dying neuronal cells by microglia (Hsieh et al., 2009).

The results described herein suggest that CD33 represents a novel regulator of microglial clearance of Aβ and a novel target for the treatment and prevention of AD. It is interesting to note that therapies targeting CD33 have already been developed in acute myeloid leukemia (AML), due to its high membrane expression in myeloid cells (Jandus et al., 2011; O'Reilly and Paulson, 2009). Naked humanized anti-CD33 and calicheamicin-conjugated humanized murine anti-CD33 antibodies have been developed and tested in several phase III clinical trials of AML, with mixed results (Jandus et al., 2011; Jurcic, 2012; Ricart, 2011). This suggests that the development of a CD33 antibody that is able to cross the BBB is feasible in principle. A chimeric antibody in which the CD33 antibody is fused to a monoclonal antibody against the human insulin receptor could facilitate the receptor-mediated passage of the chimera across the BBB (O'Reilly and Paulson, 2009). An alternative approach is the development of small compounds, e.g. sialic acid-based antagonists that target CD33 specifically and inhibit its function. Furthermore, a better understanding of CD33 action in microglial cells should lead to the identification of critical cellular targets that link the activity of CD33 in microglia to the process of Aβ recognition and uptake, and can lead to the development of novel therapeutics for the prevention and treatment of AD.

Experimental Procedures

SNP Genotyping.

Genomic DNA was extracted from AD and control frozen brain tissue using the QIAamp DNA Mini Kit (Qiagen). DNA Samples were genotyped for SNPs using the TaqMan SNP genotyping assays (Shen et al., 2009). The genotyping was performed using a custom-designed TaqMan® SNP genotyping assay for the rs3865444 SNP (Life Technologies) on a CFX384 Real-Time PCR System (BioRad) in accordance with the supplier's recommendations. To determine the APOE genotype (alleles: ε2, ε3, ε4), DNA samples were genotyped at two SNPs, rs429358 and rs7412, using a pre-designed Taqman SNP genotyping assay (catalogue no. 4351379) from Life Technologies. The reactions were carried out in 384-well microtiter plates (BioRad) in a total reaction volume of 5 ul, containing 1 μl genomic DNA (5 ng/μl), 2.5 μl of 2× Gene expression master mix (Life Technologies), 0.063 ul of 80× Taqman probes, and 1 ul water. Thermal cycling was performed with 40 cycles of 92° for 15 seconds and 60° for 30 seconds. Data was analyzed using the CFX Manager Software and the allelic discrimination tool.

RNA Extraction and Real Time-PCR.

RNA was extracted from brain tissue with Trizol (Life Technologies) following manufacturer's instructions. The extracted mRNA was dissolved in water and cleaned using the RNAeasy Mini Kit (Qiagen) according to the manufacturer's protocol. Extracted mRNA (2 μg) was reverse-transcribed using the SuperScript III first strand synthesis system (Life Technologies). Gene expression was assessed by performing Taqman real-time PCR assays. Probes targeting the CD33 gene were labeled with FAM (Hs01076280_g1 specific to exons 3-4 and Hs01076281_m1 specific to exons 4-5, Life Technologies). The housekeeping genes GAPDH and β-Actin were used as controls and were labeled with a VIC/MGB probe (Life Technologies, 4326315E for β-Actin and 4326317E for GAPDH). 1:10 diluted cDNAs were mixed with the probes and 2× Gene expression master mix (Life Technologies) and amplified using a CFX384 Real-Time PCR System (BioRad). Results were analyzed by the comparative CT method. Average CT values for each sample were normalized to the average CT values of the housekeeping genes. GAPDH expression was highly correlated with β-Actin expression.

Immunohistochemistry and Stereology.

For immunohistochemistry, mice were deeply anesthetized with isoflurane, then perfused with 0.9% sodium chloride and ice-cold 4% paraformaldehyde (PFA). Subsequently, brains were removed from the skull and post-fixed overnight in 4% PFA. The left hemisphere was dehydrated with ethanol and embedded in paraffin, whereas the right hemisphere was cryoprotected by incubation in 15% and 30% sucrose solutions and embedded in OCT.

Sections (8-μm thick) were deparaffinized and incubated with 3% $H_2O_2$ to quench endogenous peroxidases for DAB staining Antigen retrieval was performed using the Diva Decloaker (Biocare Medical) or citrate buffer (0.01M, pH 6.0, 0.05% Tween-20) in a microwave oven (95° C., 20 minutes). Sections were subsequently blocked using 2% BSA, 0.1% Triton X-100 in phosphate buffered saline (PBS), or alternatively with Antibody diluent (Cell signaling). Primary antibodies were directed against human CD33 (mouse monoclonal, 1:100, clone PWS44, Vector Laboratories) (Hoyer et al., 2008; Rollins-Raval and Roth, 2012); MAP2 (rabbit polyclonal, 1:500, Millipore); Iba1 (rabbit polyclonal, 1:500, Wako); human GFAP (rabbit polyclonal, 1:1,000, Sigma); mouse GFAP (mouse monoclonal, 1:500, clone GA5, Millipore); human von Willebrand factor (rabbit polyclonal, 1:500, Millipore); human myelin basic protein (rabbit polyclonal, 1:300, Millipore). To detect amyloid plaques, sections were labeled with 1% Thioflavin S in water for 8 minutes at room temperature, then incubated in 80% ethanol for 2 minutes and mounted. For the immunostaining with the antibodies targeting human Aβ (mouse monoclonal, clone 10D5 [1:50] or clone 3D6 [1:2000], Elan Pharmaceuticals), antigen retrieval was performed using citrate buffer, in a microwave oven (95° C., 20 minutes) followed by incubation in 90% formic acid for 5 minutes. Biotinylated secondary antibodies were from Vector Laboratories.

For immunofluorescence experiments, Alexa-488/564/647-coupled secondary antibodies and Alexa 568-coupled streptavidin were acquired from Life Technologies. Sections were mounted with aqueous mounting medium containing DAPI and anti-fading reagent (Life Technologies).

For stereology-based quantitative studies, primary antibodies were detected with DAB, using different Vectastain ABC kits (Vector Laboratories) according to the provider's instructions. Sections were dehydrated with increasing concentrations of ethanol, cleared with xylene, and coverslipped with Cytoseal-XYL xylene-based mounting medium (Richard-Allan Scientific).

An unbiased stereology-based quantification method was used to determine the number of CD33-positive microglia and neurons on single immunostained sections from human frontal cortex (Brodmann areas 8, 9) (Serrano-Pozo et al., 2011). Briefly, sections were placed on the motorized stage of an upright Olympus BX51 microscope that is equipped with a DP70 video-camera and controlled by a computer with the image analysis software CAST (Olympus, Tokyo, Japan). The region of interest (full-width) cortex was outlined under the 4× objective and CD33-positive cells were counted under the 40× objective using a 1% meander sampling and a 10% counting frame (3565.2 μm$^2$).

Assessment of Aβ plaque burden was performed in an upright Leica DMRB microscope (Leica, Germany)

equipped with a motorized stage and a CCD camera and coupled with the software BIOQUANT NOVA PRIME, version 6.90.10 (MBSR). Aβ plaque burden was measured as the percentage of total surface stained by the anti-Aβ antibody (clone 10D5) in a full-width strip of cortex (approximately 1-cm long) using the optical threshold application of the software (Serrano-Pozo et al., 2011).

Assessment of Aβ Plaque Burden in Mice.

Coronal sections stained with the anti-Aβ antibody 3D6 (1:2000, Elan Pharmaceuticals) were imaged using an upright Olympus BX51 microscope. Six coronal sections spanning the cortex and four coronal sections spanning the hippocampus (at different depths on the rostro-caudal axis) were imaged for each animal. The amyloid plaque burden (area occupied by all plaques divided by the total area) was estimated in the cortex or hippocampus for each section using ImageJ software. Values from each section were then averaged to derive a mean plaque burden for each animal. 9-11 male mice were analyzed in each group (age 6-7 months).

ELISA.

For ELISA, mice were deeply anesthetized with isoflurane, then perfused with 0.9% sodium chloride. The brains were extracted and cortices and hippocampi were dissected. To assess Aβ levels, mouse cortices or human frozen brain tissue (frontal cortex) were homogenized in 5 volumes of TBS containing 5 mM EDTA, phosphatase inhibitor (ThermoFisher), EDTA-free protease inhibitor cocktail (Roche) and 2 mM 1,10-phenantroline (Sigma), using a Polytron benchtop lab homogenizer (Wheaton) at 4° C. The homogenate was centrifuged at 100,000 g for 1 hour at 4° C. using an Optima TL ultracentrifuge and a TLA 120.2 rotor (Beckman Coulter). Supernatants were collected and used to measure TBS-soluble Aβ. The resulting pellet was homogenized in 70% formic acid (the volume of used formic acid was equal to the volume of TBS homogenate used for centrifugation). Samples were centrifuged at 100,000 g for 1 hour at 4° C. and supernatants were collected. Formic acid-containing supernatants were neutralized with 1M Tris-base, pH 11 (1:20 v:v) and samples were used to measure formic acid-soluble Aβ. Aβ40 and Aβ42 ELISAs were performed using Aβ ELISA kits from Wako.

Western Blot Analysis.

Brain tissue was homogenized in 5 volumes of TBS containing 5 mM EDTA, phosphatase inhibitor (ThermoFisher), EDTA-free protease inhibitor cocktail (Roche) and 2 mM 1,10-phenantroline (Sigma). The homogenate was mixed with an equal volume of 2× radio-immunoprecipitation assay (RIPA) buffer (Millipore) supplemented with all the above-described inhibitors. Samples were incubated on a rotating wheel for 30 minutes at 4° C. and centrifuged at 12,000 g for 15 minutes at 4° C. The supernatant was collected and used for western blot analysis. Lysates were assessed for protein concentration using the BCA kit (Pierce). Samples were boiled in sample buffer containing lithium dodecyl sulfate and β-mercaptoethanol as reducing agent (Life Technologies), and resolved on 4%-12% Bis-Tris polyacrylamide precast gels (NuPAGE system, Life Technologies). Gels were transferred onto PVDF membranes (BioRad) using wet transfer system (BioRad). The primary antibodies were directed against: human CD33 (mouse monoclonal, 1:100, clone PWS44, Vector Laboratories); Iba1 (rabbit polyclonal, 1:500, Wako); GAPDH (mouse monoclonal, 1:10,000, Millipore); β-Actin (mouse monoclonal, 1:5,000, Sigma), APP (rabbit polyclonal, 1:2,000, clone C7 targeting the amino acid residues 732-751 in APP, custom-designed by Open Biosystems) (Podlisny et al., 1991) and mouse CD33 (mCD33, rabbit polyclonal, 1:200, custom-designed by Open Biosystems). Densitometric analyses were performed using Quantity One software (BioRad). Band density values were normalized to GAPDH or 13-Actin levels.

Generation of an Anti-Mouse CD33 Antibody.

mCD33 is a rabbit polyclonal antibody that was generated by Open Biosystems. It was raised against a mouse CD33 epitope that is absent in other mouse CD33-related Siglecs and corresponds to amino acid residues 18-32 (DLEFQLVAPESVTVE). The antibody was characterized by western blot analysis and immunocytochemistry (FIGS. 4 and 10).

Primary Microglia Isolation.

Microglial cells were prepared from WT or CD33$^{-/-}$ brains at postnatal day 1 as previously described (Choi et al., 2008; Gorlovoy et al., 2009). Briefly, meninges and leptomeningeal blood vessels were removed from the cortex. Cells were dissociated by trituration and cultured in DMEM containing 10% heat-inactivated fetal bovine serum, 2 mM L-glutamine and 1% penicillin/streptomycin (Life Technologies) for 14-21 days in poly-D-lysine-coated 75 cm2 flasks (Biocat) to form a confluent glial monolayer. Half of the medium was replaced with fresh cell culture medium every three days. To collect microglial cells, the cultures were shaken on a rotary shaker (placed in a cell culture incubator, 37° C. and 5% CO2) at 250 rpm for 3 hours. The detached microglial cells were collected by centrifugation and the enriched microglial cell suspension was plated onto poly-D-lysine-coated 6-well plates (Biocat) or onto 24-well plates containing poly-D-lysine-coated glass coverslips. After the cells attached, the medium was replaced with fresh cell culture medium. The purity of the isolated microglia was determined by immunostaining with antibodies directed against Iba1. In average, 93% of cultured cells were immunostained with Iba1.

Cell Culture and Transfection.

Two pcDNA3.1 plasmids encoding human wild-type CD33 (CD33WT) and mutant CD33K283/288/309/312/313/315/352R (CD33K7R) were generously provided by Roland B. Walter and were previously described (Walter et al., 2008a). pCMV6-XL5 plasmid encoding CD33 that lacks the sialic acid-binding V-type immunoglobulin-like domain (CD33ΔV-Ig) was acquired from OriGene. CD33ΔV-Ig cDNA was amplified and subcloned into a pcDNA3.1 vector (Life Technologies). All constructs were verified by sequencing. BV2 microglial cell line was kindly provided by Linda Van Eldik (Bachstetter et al., 2011) and was maintained in DMEM containing 5% heat-inactivated fetal bovine serum, 2 mM L-Glutamine and 1% penicillin/streptomycin (Life Technologies). Cells were transiently transfected with CD33 plasmids using Lipofectamine-Plus (Life Technologies) according to the manufacturer's instructions.

Aβ Uptake and Degradation Assays.

Primary mouse microglia or BV2 cells transfected with CD33 plasmids were treated with 2 μg/ml Aβ42 (AnaSpec) in serum-free DMEM medium for 3 hours. Cells were washed with DMEM and maintained for additional 3 hours in serum- and Aβ42-free DMEM. Afterwards, cells were extensively washed with PBS and were lysed in cell lysis buffer (50 mM Tris-HCl, pH 7.4, 150 mM NaCl, 5 mM EDTA, 1% SDS) supplemented with EDTA-free protease inhibitors (Roche) and 2 mM 1,10 phenantroline (Sigma). Lysates were centrifuged at 12,000 g at 4° C. for 15 minutes. Supernatants were collected and further used for ELISAs. Aβ42 levels were measured using Aβ42 ELISA kit (Wako)

and normalized to total protein concentration that was assessed by BCA method (Pierce).

For immunofluorescence experiments, primary mouse microglial or BV2 cells were incubated with 2 µg/ml Alexa 555-labeled Aβ42 (AnaSpec) in serum-free DMEM for 3 hours, washed extensively with PBS and fixed with 4% PFA for 20 minutes. Cells were washed with PBS, blocked with 4% BSA in PBS and incubated with the primary antibodies targeting: mouse CD33 (rabbit polyclonal, 1:200, custom-designed by Open Biosystems), human CD33 (mouse monoclonal, 1:200, clone PWS44, Vector Laboratories) and Iba1 (rabbit polyclonal, 1:500, Wako, or goat polyclonal, 1:500, Abcam). Alexa 488/647 conjugated secondary antibodies were purchased from Life Technologies. Coverslips were mounted with aqueous mounting medium containing DAPI and anti-fading reagent (Life Technologies).

To quantify intracellular Alexa555-labeled Aβ42, pictures displaying the intracellular Aβ42 in transfected BV2 or mouse primary microglial cells were used. The area corresponding to intracellular Aβ42 was carefully delineated and the average intensity of the signal was determined within this area. To correct for differences in background intensity, an area devoid of Aβ42 was used and the average intensity in this area was subtracted from the average intensity of Aβ42 signal. The quantifications were performed using the ImageJ software and the values are represented in arbitrary units. At least 30 cells were analyzed per condition.

Brain Specimens.

Formalin-fixed, paraffin-embedded 8 micron-thick sections, as well as frozen tissue specimens from the frontal cortex of 25 patients with AD and 15 age-matched non-demented control subjects were obtained from the Massachusetts Alzheimer's Disease Research Center Brain Bank. All the study subjects or their next of kin gave written informed consent for the brain donation, and the Massachusetts General Hospital Institutional Review Board approved the study protocol. The demographic characteristics of both groups are shown in Table 1. All patients with AD fulfilled the National Institute of Neurological and Communicative Disorders and Stroke-Alzheimer's Disease and Related Disorders Associations criteria for probable AD and the National Institute on Aging-Reagan Institute criteria for high likelihood of AD.

Animals.

$APP_{Swe}/PS1_{\Delta E9}$ transgenic mice (referred to as APP/PS1) (Jankowsky et al., 2004) and constitutive CD33 knockout mice (Brinkman-Van der Linden et al., 2003) were obtained from The Jackson Laboratory (catalogue no. 005864 and 006942, respectively). Both mouse strains are on the C57Bl/6 background. All mice were housed under standard conditions with free access to food and water. All animal experiments were performed in accordance with national guidelines (National Institutes of Health) and approved by Massachusetts General Hospital and McLaughlin Institute Institutional Animal Care and Use Committees.

Statistical Analysis.

A general linear regression model adjusting for appropriate covariates was used to test for allelic association between the rs3865444 SNP and quantitative traits, as implemented in PLINK v1.07 (http://pngu.mgh.harvard.edu/purcell/plink/) (Purcell et al., 2007). To identify covariates that maximize the regression model's predictive ability and predict the quantitative traits for the human samples, a stepwise regression procedure was performed using age, gender, disease status, post-mortem interval, and presence of APOE ε4 allele. The stepwise regression analysis was performed using the R (v2.10.0) software package (R Development Core Team, 2009). Statistics and correlations of different quantitative traits were performed using the GraphPad Prism software, version 5.0 (GraphPad Inc., La Jolla, Calif.). The normality of quantitative trait data sets was tested with the D'Agostino-Pearson omnibus test. Student's t-test and Pearson's correlation test were performed for normally-distributed data sets, and Mann-Whitney U and Spearman's correlation tests otherwise. Multiple group analyses were performed by one-way analysis of variance (ANOVA) followed by Tukey's post-hoc test or by one-way Kruskal-Wallis ANOVA followed by Dunn's post-hoc test.

REFERENCES FOR EXAMPLE 1

Aguzzi, A., Barres, B. A., and Bennett, M. L. (2013). Microglia: scapegoat, saboteur, or something else? Science 339, 156-161.

Bell, R. D., Sagare, A. P., Friedman, A. E., Bedi, G. S., Holtzman, D. M., Deane, R., and Zlokovic, B. V. (2007). Transport pathways for clearance of human Alzheimer's amyloid beta-peptide and apolipoproteins E and J in the mouse central nervous system. Journal of cerebral blood flow and metabolism: official journal of the International Society of Cerebral Blood Flow and Metabolism 27, 909-918.

Bertram, L., Lange, C., Mullin, K., Parkinson, M., Hsiao, M., Hogan, M. F., Schjeide, B. M., Hooli, B., Divito, J., Ionita, I., et al. (2008). Genome-wide association analysis reveals putative Alzheimer's disease susceptibility loci in addition to APOE. American journal of human genetics 83, 623-632.

Bertram, L., Lill, C. M., and Tanzi, R. E. (2010). The genetics of Alzheimer disease: back to the future. Neuron 68, 270-281.

Brinkman-Van der Linden, E. C., Angata, T., Reynolds, S. A., Powell, L. D., Hedrick, S. M., and Varki, A. (2003). CD33/Siglec-3 binding specificity, expression pattern, and consequences of gene deletion in mice. Molecular and cellular biology 23, 4199-4206.

Chan, S. L., Kim, W. S., Kwok, J. B., Hill, A. F., Cappai, R., Rye, K. A., and Garner, B. (2008). ATP-binding cassette transporter A7 regulates processing of amyloid precursor protein in vitro. Journal of neurochemistry 106, 793-804.

Choi, S. H., Veeraraghavalu, K., Lazarov, O., Marler, S., Ransohoff, R. M., Ramirez, J. M., and Sisodia, S. S. (2008). Non-cell-autonomous effects of presenilin 1 variants on enrichment-mediated hippocampal progenitor cell proliferation and differentiation. Neuron 59, 568-580.

Crocker, P. R., McMillan, S. J., and Richards, H. E. (2012). CD33-related siglecs as potential modulators of inflammatory responses Annals of the New York Academy of Sciences 1253, 102-111.

Crocker, P. R., Paulson, J. C., and Varki, A. (2007). Siglecs and their roles in the immune system. Nature reviews Immunology 7, 255-266.

DeMattos, R. B., Cirrito, J. R., Parsadanian, M., May, P. C., O'Dell, M. A., Taylor, J. W., Harmony, J. A., Aronow, B. J., Bales, K. R., Paul, S. M., et al. (2004). ApoE and clusterin cooperatively suppress Abeta levels and deposition: evidence that ApoE regulates extracellular Abeta metabolism in vivo. Neuron 41, 193-202.

Frank, S., Burbach, G. J., Bonin, M., Walter, M., Streit, W., Bechmann, I., and Deller, T. (2008). TREM2 is upregulated in amyloid plaque-associated microglia in aged APP23 transgenic mice. Glia 56, 1438-1447.

Gorlovoy, P., Larionov, S., Pham, T. T., and Neumann, H. (2009). Accumulation of tau induced in neurites by microglial proinflammatory mediators. FASEB journal: official publication of the Federation of American Societies for Experimental Biology 23, 2502-2513.

Grathwohl, S. A., Kalin, R. E., Bolmont, T., Prokop, S., Winkelmann, G., Kaeser, S. A., Odenthal, J., Radde, R., Eldh, T., Gandy, S., et al. (2009). Formation and maintenance of Alzheimer's disease beta-amyloid plaques in the absence of microglia. Nature neuroscience 12, 1361-1363.

Guerreiro, R., Wojtas, A., Bras, J., Carrasquillo, M., Rogaeva, E., Majounie, E., Cruchaga, C., Sassi, C., Kauwe, J. S., Younkin, S., et al. (2013). TREM2 variants in Alzheimer's disease. The New England journal of medicine 368, 117-127.

Hardy, J., and Selkoe, D. J. (2002). The amyloid hypothesis of Alzheimer's disease: progress and problems on the road to therapeutics. Science 297, 353-356.

Hardy, J. A., and Higgins, G. A. (1992). Alzheimer's disease: the amyloid cascade hypothesis. Science 256, 184-185.

Harold, D., Abraham, R., Hollingworth, P., Sims, R., Gerrish, A., Hamshere, M. L., Pahwa, J. S., Moskvina, V., Dowzell, K., Williams, A., et al. (2009). Genome-wide association study identifies variants at CLU and PICALM associated with Alzheimer's disease. Nature genetics 41, 1088-1093.

Hashimoto, T., Serrano-Pozo, A., Hori, Y., Adams, K. W., Takeda, S., Banerji, A. O., Mitani, A., Joyner, D., Thyssen, D. H., Bacskai, B. J., et al. (2012). Apolipoprotein E, especially apolipoprotein E4, increases the oligomerization of amyloid beta peptide. The Journal of neuroscience: the official journal of the Society for Neuroscience 32, 15181-15192.

Hollingworth, P., Harold, D., Sims, R., Gerrish, A., Lambert, J. C., Carrasquillo, M. M., Abraham, R., Hamshere, M. L., Pahwa, J. S., Moskvina, V., et al. (2011). Common variants at ABCA7, MS4A6A/MS4A4E, EPHA1, CD33 and CD2AP are associated with Alzheimer's disease. Nature genetics 43, 429-435.

Hoyer, J. D., Grogg, K. L., Hanson, C. A., Gamez, J. D., and Dogan, A. (2008). CD33 detection by immunohistochemistry in paraffin-embedded tissues: a new antibody shows excellent specificity and sensitivity for cells of myelomonocytic lineage. American journal of clinical pathology 129, 316-323.

Hsieh, C. L., Koike, M., Spusta, S. C., Niemi, E. C., Yenari, M., Nakamura, M. C., and Seaman, W. E. (2009). A role for TREM2 ligands in the phagocytosis of apoptotic neuronal cells by microglia. Journal of neurochemistry 109, 1144-1156.

Jandus, C., Simon, H. U., and von Gunten, S. (2011). Targeting siglecs—a novel pharmacological strategy for immuno- and glycotherapy. Biochemical pharmacology 82, 323-332.

Jankowsky, J. L., Fadale, D. J., Anderson, J., Xu, G. M., Gonzales, V., Jenkins, N. A., Copeland, N. G., Lee, M. K., Younkin, L. H., Wagner, S. L., et al. (2004). Mutant presenilins specifically elevate the levels of the 42 residue beta-amyloid peptide in vivo: evidence for augmentation of a 42-specific gamma secretase. Human molecular genetics 13, 159-170.

Jiang, Q., Lee, C. Y., Mandrekar, S., Wilkinson, B., Cramer, P., Zelcer, N., Mann, K., Lamb, B., Willson, T. M., Collins, J. L., et al. (2008). ApoE promotes the proteolytic degradation of Abeta. Neuron 58, 681-693.

Jonsson, T., Stefansson, H., Steinberg, S., Jonsdottir, I., Jonsson, P. V., Snaedal, J., Bjornsson, S., Huttenlocher, J., Levey, A. I., Lah, J. J., et al. (2013). Variant of TREM2 associated with the risk of Alzheimer's disease. The New England journal of medicine 368, 107-116.

Jurcic, J. G. (2012). What happened to anti-CD33 therapy for acute myeloid leukemia? Current hematologic malignancy reports 7, 65-73.

Karch, C. M., Jeng, A. T., Nowotny, P., Cady, J., Cruchaga, C., and Goate, A. M. (2012). Expression of novel Alzheimer's disease risk genes in control and Alzheimer's disease brains. PloS one 7, e50976.

Klesney-Tait, J., Turnbull, I. R., and Colonna, M. (2006). The TREM receptor family and signal integration. Nature immunology 7, 1266-1273.

Lambert, J. C., Heath, S., Even, G., Campion, D., Sleegers, K., Hiltunen, M., Combarros, O., Zelenika, D., Bullido, M. J., Tavernier, B., et al. (2009). Genome-wide association study identifies variants at CLU and CR1 associated with Alzheimer's disease. Nature genetics 41, 1094-1099.

Lee, C. Y., Tse, W., Smith, J. D., and Landreth, G. E. (2012). Apolipoprotein E promotes beta-amyloid trafficking and degradation by modulating microglial cholesterol levels. The Journal of biological chemistry 287, 2032-2044.

Liu, C. C., Kanekiyo, T., Xu, H., and Bu, G. (2013). Apolipoprotein E and Alzheimer disease: risk, mechanisms and therapy. Nature reviews Neurology 9, 184.

Mandrekar, S., Jiang, Q., Lee, C. Y., Koenigsknecht-Talboo, J., Holtzman, D. M., and Landreth, G. E. (2009). Microglia mediate the clearance of soluble Abeta through fluid phase macropinocytosis. The Journal of neuroscience: the official journal of the Society for Neuroscience 29, 4252-4262.

Melchior, B., Garcia, A. E., Hsiung, B. K., Lo, K. M., Doose, J. M., Thrash, J. C., Stalder, A. K., Staufenbiel, M., Neumann, H., and Carson, M. J. (2010). Dual induction of TREM2 and tolerance-related transcript, Tmem176b, in amyloid transgenic mice: implications for vaccine-based therapies for Alzheimer's disease. ASN neuro 2, e00037.

Naj, A. C., Jun, G., Beecham, G. W., Wang, L. S., Vardarajan, B. N., Buros, J., Gallins, P. J., Buxbaum, J. D., Jarvik, G. P., Crane, P. K., et al. (2011). Common variants at MS4A4/MS4A6E, CD2AP, CD33 and EPHA1 are associated with late-onset Alzheimer's disease. Nature genetics 43, 436-441.

O'Reilly, M. K., and Paulson, J. C. (2009). Siglecs as targets for therapy in immune-cell-mediated disease. Trends in pharmacological sciences 30, 240-248.

Paulson, J. C., Macauley, M. S., and Kawasaki, N. (2012). Siglecs as sensors of self in innate and adaptive immune responses Annals of the New York Academy of Sciences 1253, 37-48.

Perez-Oliva, A. B., Martinez-Esparza, M., Vicente-Fernandez, J. J., Corral-San Miguel, R., Garcia-Penarrubia, P., and Hernandez-Caselles, T. (2011). Epitope mapping, expression and post-translational modifications of two isoforms of CD33 (CD33M and CD33m) on lymphoid and myeloid human cells. Glycobiology 21, 757-770.

Pillai, S., Netravali, I. A., Cariappa, A., and Mattoo, H. (2012). Siglecs and immune regulation. Annual review of immunology 30, 357-392.

Prinz, M., Priller, J., Sisodia, S. S., and Ransohoff, R. M. (2011). Heterogeneity of CNS myeloid cells and their roles in neurodegeneration. Nature neuroscience 14, 1227-1235.

Purcell, S., Neale, B., Todd-Brown, K., Thomas, L., Ferreira, M. A., Bender, D., Maller, J., Sklar, P., de Bakker, P. I., Daly, M. J., et al. (2007). PLINK: a tool set for whole-genome association and population-based linkage analyses. American journal of human genetics 81, 559-575.

Querfurth, H. W., and LaFerla, F. M. (2010). Alzheimer's disease. The New England journal of medicine 362, 329-344.

Reilly, J. F., Games, D., Rydel, R. E., Freedman, S., Schenk, D., Young, W. G., Morrison, J. H., and Bloom, F. E. (2003). Amyloid deposition in the hippocampus and entorhinal cortex: quantitative analysis of a transgenic mouse model. Proceedings of the National Academy of Sciences of the United States of America 100, 4837-4842.

Ricart, A. D. (2011). Antibody-drug conjugates of calicheamicin derivative: gemtuzumab ozogamicin and inotuzumab ozogamicin. Clinical cancer research: an official journal of the American Association for Cancer Research 17, 6417-6427.

Rollins-Raval, M. A., and Roth, C. G. (2012). The value of immunohistochemistry for CD14, CD123, CD33, myeloperoxidase and CD68R in the diagnosis of acute and chronic myelomonocytic leukaemias. Histopathology 60, 933-942.

Selkoe, D. J. (2012). Preventing Alzheimer's disease. Science 337, 1488-1492.

Serrano-Pozo, A., Mielke, M. L., Gomez-Isla, T., Betensky, R. A., Growdon, J. H., Frosch, M. P., and Hyman, B. T. (2011). Reactive glia not only associates with plaques but also parallels tangles in Alzheimer's disease. The American journal of pathology 179, 1373-1384.

Seshadri, S., Fitzpatrick, A. L., Ikram, M. A., DeStefano, A. L., Gudnason, V., Boada, M., Bis, J. C., Smith, A. V., Carassquillo, M. M., Lambert, J. C., et al. (2010). Genome-wide analysis of genetic loci associated with Alzheimer disease. JAMA: the journal of the American Medical Association 303, 1832-1840.

Shen, G. Q., Abdullah, K. G., and Wang, Q. K. (2009). The TaqMan method for SNP genotyping. Methods Mol Biol 578, 293-306.

Tanzi, R. E. (2012). A Brief History of Alzheimer's Disease Gene Discovery. Journal of Alzheimer's disease: JAD.

Tanzi, R. E., and Bertram, L. (2005). Twenty years of the Alzheimer's disease amyloid hypothesis: a genetic perspective. Cell 120, 545-555.

Treusch, S., Hamamichi, S., Goodman, J. L., Matlack, K. E., Chung, C. Y., Baru, V., Shulman, J. M., Parrado, A., Bevis, B. J., Valastyan, J. S., et al. (2011). Functional links between Abeta toxicity, endocytic trafficking, and Alzheimer's disease risk factors in yeast. Science 334, 1241-1245.

von Gunten, S., and Bochner, B. S. (2008). Basic and clinical immunology of Siglecs. Annals of the New York Academy of Sciences 1143, 61-82.

Walter, R. B., Hausermann, P., Raden, B. W., Teckchandani, A. M., Kamikura, D. M., Bernstein, I. D., and Cooper, J. A. (2008). Phosphorylated ITIMs enable ubiquitylation of an inhibitory cell surface receptor. Traffic 9, 267-279.

Wang, Y. J., Wang, X., Lu, J. J., Li, Q. X., Gao, C. Y., Liu, X. H., Sun, Y., Yang, M., Lim, Y., Evin, G., et al. (2011). p75NTR regulates Abeta deposition by increasing Abeta production but inhibiting Abeta aggregation with its extracellular domain. The Journal of neuroscience: the official journal of the Society for Neuroscience 31, 2292-2304.

Xiao, Q., Gil, S. C., Yan, P., Wang, Y., Han, S., Gonzales, E., Perez, R., Cirrito, J. R., and Lee, J. M. (2012). Role of phosphatidylinositol clathrin assembly lymphoid-myeloid leukemia (PICALM) in intracellular amyloid precursor protein (APP) processing and amyloid plaque pathogenesis. The Journal of biological chemistry 287, 21279-21289.

Yerbury, J. J., Poon, S., Meehan, S., Thompson, B., Kumita, J. R., Dobson, C. M., and Wilson, M. R. (2007). The extracellular chaperone clusterin influences amyloid formation and toxicity by interacting with prefibrillar structures. FASEB journal: official publication of the Federation of American Societies for Experimental Biology 21, 2312-2322.

Bachstetter, A. D., Xing, B., de Almeida, L., Dimayuga, E. R., Watterson, D. M., and Van Eldik, L. J. (2011). Microglial p38alpha MAPK is a key regulator of proinflammatory cytokine up-regulation induced by toll-like receptor (TLR) ligands or beta-amyloid (Abeta). Journal of neuroinflammation 8, 79.

Podlisny, M. B., Tolan, D. R., and Selkoe, D. J. (1991). Homology of the amyloid beta protein precursor in monkey and human supports a primate model for beta amyloidosis in Alzheimer's disease. The American journal of pathology 138, 1423-1435.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A method of treating a neuro-inflammation disorder associated with beta amyloid accumulation in a subject, the method comprising administering to a subject in need thereof an effective amount of an agent that inhibits or reduces the expression or activity of CD33 protein, wherein the agent is a nucleic acid comprising a nucleotide sequence substantially complimentary to at least a part of a nucleic acid encoding the CD33 protein.

2. The method of method of claim 1, wherein the agent is a nucleic acid and the method comprises administering a vector encoding/expressing the agent to the subject.

3. The method of claim 2, wherein the vector is a viral vector.

4. The method of claim 3, wherein the viral vector is an adeno-associated virus (AAV) vector.

5. The method of claim 1, wherein the neuro-inflammation disorder is Alzheimer's disease (AD) or Lewy body dementia.

6. The method of claim 5, wherein the neuro-inflammation disorder is Alzheimer's Disease.

7. The method of claim 1, wherein the agent is siRNA, shRNA, antisense RNA or oligonucleotide, miRNA, anti-microRNA or ribozyme.

8. The method of claim 7, wherein the agent is siRNA, shRNA or antisense oligonucleotide.

9. The method of claim 8, wherein the agent is siRNA.

10. The method of claim 1, wherein the nucleic acid encoding the CD33 protein has a nucleotides sequence of SEQ ID NO: 3, SEQ ID NO: 4, SEQ ID NO: 5, SEQ ID NO: 6 or SEQ ID NO: 7.

11. A method of treating a neuro-inflammation disorder associated with beta amyloid accumulation in a subject, the method comprising administering to a subject in need thereof a nucleic acid encoding a CD33 protein, wherein the CD33 protein lacks a sialic acid binding domain.

12. The method of claim 11, wherein the CD33 protein comprises an amino acid sequence SEQ ID NO: 8.

13. The method of claim 11, wherein the nucleic acid is a vector.

14. The method of claim 13, wherein the vector is a viral vector.

15. The method of claim 14, wherein the viral vector is an AAV vector.

16. The method of claim 11, wherein the nucleic acid is modified RNA.

17. The method of claim 11, wherein the neuro-inflammation disorder is Alzheimer's disease (AD) or Lewy body dementia.

18. The method of claim 17, wherein the neuro-inflammation disorder is Alzheimer's Disease.

* * * * *

SEQUENCE LISTING

```
<160> NUMBER OF SEQ ID NOS: 11

<210> SEQ ID NO 1
<211> LENGTH: 403
<212> TYPE: PRT
<213> ORGANISM: Mus sp.
```

-continued

<400> SEQUENCE: 1

Met Leu Trp Pro Leu Pro Leu Phe Leu Leu Cys Ala Gly Ser Leu Ala
1               5                   10                  15

Gln Asp Leu Glu Phe Gln Leu Val Ala Pro Glu Ser Val Thr Val Glu
            20                  25                  30

Glu Gly Leu Cys Val His Val Pro Cys Ser Val Phe Tyr Pro Ser Ile
        35                  40                  45

Lys Leu Thr Leu Gly Pro Val Thr Gly Ser Trp Leu Arg Lys Gly Val
    50                  55                  60

Ser Leu His Glu Asp Ser Pro Val Ala Thr Ser Asp Pro Arg Gln Leu
65                  70                  75                  80

Val Gln Lys Ala Thr Gln Gly Arg Phe Gln Leu Leu Gly Asp Pro Gln
                85                  90                  95

Lys His Asp Cys Ser Leu Phe Ile Arg Asp Ala Gln Lys Asn Asp Thr
            100                 105                 110

Gly Met Tyr Phe Phe Arg Val Val Arg Glu Pro Phe Val Arg Tyr Ser
        115                 120                 125

Tyr Lys Lys Ser Gln Leu Ser Leu His Val Thr Ser Leu Ser Arg Thr
    130                 135                 140

Pro Asp Ile Ile Ile Pro Gly Thr Leu Glu Ala Gly Tyr Pro Ser Asn
145                 150                 155                 160

Leu Thr Cys Ser Val Pro Trp Ala Cys Glu Gln Gly Thr Pro Pro Thr
                165                 170                 175

Phe Ser Trp Met Ser Thr Ala Leu Thr Ser Leu Ser Ser Arg Thr Thr
            180                 185                 190

Asp Ser Ser Val Leu Thr Phe Thr Pro Gln Pro Gln Asp His Gly Thr
        195                 200                 205

Lys Leu Thr Cys Leu Val Thr Phe Ser Gly Ala Gly Val Thr Val Glu
    210                 215                 220

Arg Thr Ile Gln Leu Asn Val Thr Arg Lys Ser Gly Gln Met Arg Glu
225                 230                 235                 240

Leu Val Leu Val Ala Val Gly Glu Ala Thr Val Lys Leu Leu Ile Leu
                245                 250                 255

Gly Leu Cys Leu Val Phe Leu Ile Val Met Phe Cys Arg Arg Lys Thr
            260                 265                 270

Thr Lys Leu Ser Val His Met Gly Cys Glu Asn Pro Ile Lys Arg Gln
        275                 280                 285

Glu Ala Ile Thr Ser Tyr Asn His Cys Leu Ser Pro Thr Ala Ser Asp
    290                 295                 300

Ala Val Thr Pro Gly Cys Ser Ile His Arg Leu Ile Ser Arg Thr Pro
305                 310                 315                 320

Arg Cys Thr Ala Ile Leu Arg Ile Gln Asp Pro Tyr Arg Arg Thr His
                325                 330                 335

Leu Arg Asn Arg Ala Val Ser Thr Leu Arg Phe Pro Trp Ile Ser Trp
            340                 345                 350

Glu Gly Ser Leu Arg Ser Thr Gln Arg Ser Lys Cys Thr Lys Leu Cys
        355                 360                 365

Ser Pro Val Lys Asn Leu Cys Pro Leu Trp Leu Pro Val Asp Asn Ser
    370                 375                 380

Cys Ile Pro Leu Ile Pro Glu Trp Val Met Leu Leu Cys Val Ser Leu
385                 390                 395                 400

Thr Leu Ser

<210> SEQ ID NO 2
<211> LENGTH: 364
<212> TYPE: PRT
<213> ORGANISM: Homo sapiens

<400> SEQUENCE: 2

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360

<210> SEQ ID NO 3

<211> LENGTH: 1085
<212> TYPE: DNA
<213> ORGANISM: Homo sapiens

<400> SEQUENCE: 3

```
tctgctcaca caggaagccc tggaagctgc ttcctcagac atgccgctgc tgctactgct      60
gcccctgctg tgggcagact tgacccacag gcccaaaatc ctcatccctg cactctaga      120
acccggccac tccaaaaacc tgacctgctc tgtgtcctgg gcctgtgagc agggaacacc     180
cccgatcttc tcctggttgt cagctgcccc cacctccctg gccccagga ctactcactc      240
ctcggtgctc ataatcaccc cacggcccca ggaccacggc accaacctga cctgtcaggt     300
gaagttcgct ggagctggtg tgactacgga gagaaccatc agctcaacg tcacctatgt      360
tccacagaac ccaacaactg gtatctttcc aggagatggc tcagggaaac aagagaccag     420
agcaggagtg gttcatgggg ccattggagg agctggtgtt acagccctgc tcgctctttg     480
tctctgcctc atcttcttca tagtgaagac ccacaggagg aaagcagcca ggacagcagt    540
gggcaggaat gacacccacc ctaccacagg gtcagcctcc ccgaaacacc agaagaagtc     600
caagttacat ggccccactg aaacctcaag ctgttcaggt gccgcccta ctgtggagat      660
ggatgaggag ctgcattatg cttccctcaa cttcatgg g atgaatcctt ccaaggacac      720
ctccaccgaa tactcagagg tcaggaccca gtgaggaacc cacaagagca tcaggctcag    780
ctagaagatc cacatcctct acaggtcggg gaccaaaggc tgattcttgg agatttaaca     840
ccccacaggc aatgggttta tagacattat gtgagtttcc tgctatatta acatcatctt     900
agactttgca agcagagagt cgtggaatca aatctgtgct ctttcatttg ctaagtgtat     960
gatgtcacac aagctcctta accttccatg tctccatttt cttctctgtg aagtaggtat    1020
aagaagtcct atctcatagg gatgctgtga gcattaaata aggtacaca tggaaaacac     1080
cagtc                                                                1085
```

<210> SEQ ID NO 4
<211> LENGTH: 1466
<212> TYPE: DNA
<213> ORGANISM: Homo sapiens

<400> SEQUENCE: 4

```
tctgctcaca caggaagccc tggaagctgc ttcctcagac atgccgctgc tgctactgct      60
gcccctgctg tgggcagggg ccctggctat ggatccaaat ttctggctgc aagtgcagga    120
gtcagtgacg gtacaggagg gtttgtgcgt cctcgtgccc tgcactttct tccatcccat    180
accctactac gacaagaact ccccagttca tggttactgg ttccgggaag gagccattat    240
atccagggac tctccagtgg ccacaaacaa gctagatcaa gaagtacagg aggagactca    300
gggcagattc cgcctccttg gggatcccag taggaacaac tgctccctga gcatcgtaga    360
cgccaggagg agggataatg gttcatactt ctttcggatg gagagaggaa gtaccaaata    420
cagttacaaa tctccccagc tctctgtgca tgtgacagac ttgacccaca ggcccaaaat    480
cctcatccct ggcactctag aacccggcca ctccaaaaac ctgacctgct ctgtgtcctg     540
ggcctgtgag cagggaacac cccgatcttc tcctggttg tcagctgccc ccacctccct     600
gggccccagg actactcact cctcggtgct cataatcacc ccacggcccc aggaccacgg    660
caccaacctg acctgtcagg tgaagttcgc tggagctggt gtgactacgg agagaaccat    720
ccagctcaac gtcacctatg ttccacagaa cccaacaact ggtatctttc caggagatgg    780
ctcagggaaa caagagacca gagcaggagt ggttcatggg gccattggag gagctggtgt    840
```

```
tacagccctg ctcgctcttt gtctctgcct catcttcttc atagtgaaga cccacaggag      900
gaaagcagcc aggacagcag tgggcaggaa tgacacccac cctaccacag ggtcagcctc      960
cccgaaacac cagaagaagt ccaagttaca tggccccact gaaacctcaa gctgttcagg     1020
tgccgcccct actgtggaga tggatgagga gctgcattat gcttccctca actttcatgg     1080
gatgaatcct tccaaggaca cctccaccga atactcagag gtcaggaccc agtgaggaac     1140
ccacaagagc atcaggctca gctagaagat ccacatcctc tacaggtcgg ggaccaaagg     1200
ctgattcttg gagatttaac accccacagg caatgggttt atagacatta tgtgagtttc     1260
ctgctatatt aacatcatct tagactttgc aagcagagag tcgtggaatc aaatctgtgc     1320
tctttcattt gctaagtgta tgatgtcaca caagctcctt aaccttccat gtctccattt     1380
tcttctctgt gaagtaggta taagaagtcc tatctcatag ggatgctgtg agcattaaat     1440
aaaggtacac atggaaaaca ccagtc                                          1466
```

<210> SEQ ID NO 5
<211> LENGTH: 1108
<212> TYPE: DNA
<213> ORGANISM: Homo sapiens

<400> SEQUENCE: 5

```
tctgctcaca caggaagccc tggaagctgc ttcctcagac atgccgctgc tgctactgct       60
gcccctgctg tgggcagggg ccctggctat ggatccaaat ttctggctgc aagtgcagga      120
gtcagtgacg gtacaggagg gtttgtgcgt cctcgtgccc tgcactttct tccatcccat      180
accctactac gacaagaact ccccagttca tggttactgg ttccgggaag gagccattat      240
atccagggac tctccagtgg ccacaaacaa gctagatcaa gaagtacagg aggagactca      300
gggcagattc cgcctccttg gggatcccag taggaacaac tgctccctga gcatcgtaga      360
cgccaggagg agggataatg gttcatactt cttcggatg gagagaggaa gtaccaaata      420
cagttacaaa tctccccagc tctctgtgca tgtgacagac ttgacccaca ggcccaaaat      480
cctcatccct ggcactctag aacccggcca ctccaaaaac ctgacctgct ctgtgtcctg      540
ggcctgtgag cagggaacac cccgatcttc tcctggttg tcagctgccc ccacctccct      600
gggccccagg actactcact cctcggtgct cataatcacc ccacggcccc aggaccacgg      660
caccaacctg acctgtcagg tgaagttcgc tggagctggt gtgactacgg agagaaccat      720
ccagctcaac gtcacctatg ttccacagaa cccaacaact ggtatctttc aggagatgg       780 ctcagggaaa caagagacca gagcaggagt ggttcatggg gccattggag gagctggtgt      840
tacagccctg ctcgctcttt gtctctgcct catcttcttc atagtgaaga cccacaggag      900
gaaagcagcc aggacagcag tgggcaggaa tgacacccac cctaccacag ggtcagcctc      960
cccggtacgt tgaggccaac agatcaggag atgatggcca ttgaaaagat agtttcttgg     1020
ccgggcacag tgtttcacac ctgcaatccc agcacctttg gaggccaagg cgggcggatc     1080
acgaggtcag gagattgaga ctatcctg                                        1108
```

<210> SEQ ID NO 6
<211> LENGTH: 929
<212> TYPE: DNA
<213> ORGANISM: Homo sapiens

<400> SEQUENCE: 6

```
cacacaggaa gccctggaag ctgcttcctc agacatgccg ctgctgctac tgctgcccct       60
```

| | |
|---|---|
| gctgtgggca ggggccctgg ctatggatcc aaatttctgg ctgcaagtgc aggagtcagt | 120 |
| gacggtacag gagggtttgt gcgtcctcgt gccctgcact ttcttccatc ccatacccta | 180 |
| ctacgacaag aactccccag ttcatggtta ctggttccgg gaaggagcca ttatatccag | 240 |
| ggactctcca gtggccacaa acaagctaga tcaagaagta caggaggaga ctcagggcag | 300 |
| attccgcctc cttggggatc ccagtaggaa caactgctcc ctgagcatcg tagacgccag | 360 |
| gaggagggat aatggttcat acttctttcg gatggagaga ggaagtacca aatacagtta | 420 |
| caaatctccc cagctctctg tgcatgtgac agacttgacc cacaggccca aaatcctcat | 480 |
| ccctggcact ctagaacccg gccactccaa aaacctgacc tgctctgtgt cctgggcctg | 540 |
| tgagcaggga acacccccga tcttctcctg gttgtcagct gcccccacct ccctgggccc | 600 |
| caggactact cactcctcgg tgctcataat caccccacgg ccccaggacc acggcaccaa | 660 |
| cctgacctgt caggtgaagt tcgctggagc tggtgtgact acggagagaa ccatccagct | 720 |
| caacgtcacc tatgttccac agaacccaac aactggtatc tttccaggag atggctcagg | 780 |
| gaaacaagag accagagcag gagtggttca tggggccatt ggaggagctg gtgttacagc | 840 |
| cctgctcgct ctttgtctct gcctcatctt cttcattccc tcattccagg ctcataacaa | 900 |
| tggccccaca gcctgagaaa accaggctc | 929 |

<210> SEQ ID NO 7
<211> LENGTH: 1409
<212> TYPE: DNA
<213> ORGANISM: Homo sapiens

<400> SEQUENCE: 7

| | |
|---|---|
| cacacaggaa gccctggaag ctgcttcctc agacatgccg ctgctgctac tgctgcccct | 60 |
| gctgtgggca ggggccctgg ctatggatcc aaatttctgg ctgcaagtgc aggagtcagt | 120 |
| gacggtacag gagggtttgt gcgtcctcgt gccctgcact ttcttccatc ccatacccta | 180 |
| ctacgacaag aactccccag ttcatggtta ctggttccgg gaaggagcca ttatatccag | 240 |
| ggactctcca gtggccacaa acaagctaga tcaagaagta caggaggaga ctcagggcag | 300 |
| attccgcctc cttggggatc ccagtaggaa caactgctcc ctgagcatcg tagacgccag | 360 |
| gaggagggat aatggttcat acttctttcg gatggagaga ggaagtacca aatacagtta | 420 |
| caaatctccc cagctctctg tgcatgtgac agacttgacc cacaggccca aaatcctcat | 480 |
| ccctggcact ctagaacccg gccactccaa aaacctgacc tgctctgtgt cctgggcctg | 540 |
| tgagcaggga acacccccga tcttctcctg gttgtcagct gcccccacct ccctgggccc | 600 |
| caggactact cactcctcgg tgctcataat caccccacgg ccccaggacc acggcaccaa | 660 |
| cctgacctgt caggtgaagt tcgctggagc tggtgtgact acggagagaa ccatccagct | 720 |
| caacgtcacc tggaaacaag agaccagagc aggagtggtt catggggcca ttggaggagc | 780 |
| tggtgttaca gccctgctcg ctctttgtct ctgcctcatc ttcttcatag tgaagaccca | 840 |
| caggaggaaa gcagccagga cagcagtggg caggaatgac acccacccta ccacagggtc | 900 |
| agcctccccg aaacaccaga agaagtccaa gttacatggc cccactgaaa cctcaagctg | 960 |
| ttcaggtgcc gccccactg tggagatgga tgaggagctg cattatgctt ccctcaactt | 1020 |
| tcatgggatg aatccttcca aggacacctc caccgaatac tcagaggtca ggacccagtg | 1080 |
| aggaacccac aagagcatca ggctcagcta aagatccac atcctctaca ggtcggggac | 1140 |
| caaaggctga ttcttggaga tttaacaccc cacaggcaat gggtttatag acattatgtg | 1200 |
| agtttcctgc tatattaaca tcatcttaga ctttgcaagc agagagtcgt ggaatcaaat | 1260 |

```
ctgtgctctt tcatttgcta agtgtatgat gtcacacaag ctccttaacc ttccatgtct    1320
ccattttctt ctctgtgaag taggtataag aagtcctatc tcatagggat gctgtgagca    1380
ttaaataaag gtacacatgg aaaacacca                                      1409
```

<210> SEQ ID NO 8
<211> LENGTH: 237
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Met Pro Leu Leu Leu Leu Pro Leu Leu Trp Ala Asp Leu Thr His
1               5                   10                  15

Arg Pro Lys Ile Leu Ile Pro Gly Thr Leu Glu Pro Gly His Ser Lys
            20                  25                  30

Asn Leu Thr Cys Ser Val Ser Trp Ala Cys Glu Gln Gly Thr Pro Pro
        35                  40                  45

Ile Phe Ser Trp Leu Ser Ala Ala Pro Thr Ser Leu Gly Pro Arg Thr
    50                  55                  60

Thr His Ser Ser Val Leu Ile Ile Thr Pro Arg Pro Gln Asp His Gly
65                  70                  75                  80

Thr Asn Leu Thr Cys Gln Val Lys Phe Ala Gly Ala Gly Val Thr Thr
                85                  90                  95

Glu Arg Thr Ile Gln Leu Asn Val Thr Tyr Val Pro Gly Asn Pro Thr
            100                 105                 110

Thr Gly Ile Phe Pro Gly Asp Gly Ser Gly Lys Gln Glu Thr Arg Ala
        115                 120                 125

Gly Val Val His Gly Ala Ile Gly Gly Ala Gly Val Thr Ala Leu Leu
    130                 135                 140

Ala Leu Cys Leu Cys Leu Ile Phe Phe Ile Val Lys Thr His Arg Arg
145                 150                 155                 160

Lys Ala Ala Arg Thr Ala Val Gly Arg Asn Asp Thr His Pro Thr Thr
                165                 170                 175

Gly Ser Ala Ser Pro Lys His Gln Lys Lys Ser Lys Leu His Gly Pro
            180                 185                 190

Thr Glu Thr Ser Ser Cys Ser Gly Ala Ala Pro Thr Val Glu Met Asp
        195                 200                 205

Glu Glu Leu His Tyr Ala Ser Leu Asn Phe His Gly Met Asn Pro Ser
    210                 215                 220

Lys Asp Thr Ser Thr Glu Tyr Ser Glu Val Arg Thr Gln
225                 230                 235
```

<210> SEQ ID NO 9
<211> LENGTH: 1127
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
cagacatgcc gctgctgcta ctgctgcccc tgctgtgggc agacttgacc cacaggccca      60
aaatcctcat ccctggcact ctagaacccg gccactccaa aaacctgacc tgctctgtgt     120
cctgggcctg tgagcaggga acaccccccga tcttctcctg gttgtcagct gcccccacct    180
```

```
cctgggccc caggactact cactcctcgg tgctcataat cacccacgg ccccaggacc      240 acggcaccaa cctgacctgt caggtgaagt tcgctggagc tggtgtgact acggagagaa      300
ccatccagct caacgtcacc tatgttccac agaacccaac aactggtatc tttccaggag      360
atggctcagg gaaacaagag accagagcag gagtggttca tggggccatt ggaggagctg      420
gtgttacagc cctgctcgct ctttgtctct gcctcatctt cttcatagtg aagacccaca      480
ggaggaaagc agccaggaca gcagtgggca ggaatgacac ccaccctacc acagggtcag      540
cctccccgaa acaccagaag aagtccaagt tacatggccc cactgaaacc tcaagctgtt      600
caggtgccgc ccctactgtg gagatggatg aggagctgca ttatgcttcc ctcaactttc      660
atgggatgaa tccttccaag gacacctcca ccgaatactc agaggtcagg acccagtgag      720
gaacccacaa gagcatcagg ctcagctaga agatccacat cctctacagg tcggggacca      780
aaggctgatt cttggagatt taacacccca caggcaatgg gtttatagac attatgtgag      840
tttcctgcta tattaacatc atcttagact ttgcaagcag agagtcgtgg aatcaaatct      900
gtgctctttc atttgctaag tgtatgatgt cacacaagct ccttaacctt ccatgtctcc      960
attttcttct ctgtgaagta ggtataagaa gtcctatctc atagggatgc tgtgagcatt     1020
aaataaaggt acacatggaa aacaaaaaaa aaaaaaaaa aaaaaaaaaa aaaaaaaaa      1080 aaaaaaaaaa aaaaaaaaaa aaaaaaaaaa aaaaaaaaaa aaaaaaa                  1127

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Gly Cys
1               5

<210> SEQ ID NO 11
<211> LENGTH: 15
<212> TYPE: PRT
<213> ORGANISM: Mus sp.

<400> SEQUENCE: 11

Asp Leu Glu Phe Gln Leu Val Ala Pro Glu Ser Val Thr Val Glu
1               5                   10                  15
```